(12) United States Patent
Lichtenberger

(10) Patent No.: US 9,351,984 B2
(45) Date of Patent: *May 31, 2016

(54) COMPOSITIONS COMPRISING LECITHIN OILS AND NSAIDS FOR PROTECTING THE GASTROINTESTINAL TRACT AND PROVIDING ENHANCED THERAPEUTIC ACTIVITY

(71) Applicant: The Board of Regents of the University of Texas System, Austin, TX (US)

(72) Inventor: Lenard M. Lichtenberger, Houston, TX (US)

(73) Assignee: The Board of Regents of the University of Texas System, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/495,525

(22) Filed: Sep. 24, 2014

(65) Prior Publication Data

US 2015/0011507 A1    Jan. 8, 2015

Related U.S. Application Data

(63) Continuation of application No. 12/883,873, filed on Sep. 16, 2010, now Pat. No. 8,865,187, which is a continuation of application No. 10/433,454, filed as application No. PCT/US01/51605 on Dec. 19, 2001, now abandoned.

(60) Provisional application No. 60/256,711, filed on Dec. 19, 2000.

(51) Int. Cl.
A61K 9/06      (2006.01)
A61K 31/616    (2006.01)

(Continued)

(52) U.S. Cl.
CPC .............. *A61K 31/685* (2013.01); *A61K 9/107* (2013.01); *A61K 9/1075* (2013.01);

(Continued)

(58) Field of Classification Search
CPC ... A61K 31/616; A61K 9/107; A61K 9/1075; A61K 31/192; A61K 31/195; A61K 31/405; A61K 31/4152
See application file for complete search history.

(56) References Cited

U.S. PATENT DOCUMENTS 4,309,420 A   1/1982   Ghyczy et al.
4,332,795 A   6/1982   Ghyczy et al.

(Continued)

FOREIGN PATENT DOCUMENTS

EP    0 051 833 A1   5/1982
JP    5589225        7/1980

(Continued)

OTHER PUBLICATIONS

Canadian Patent Office, Response to Official Action, S/N 2,431,606, Sep. 21, 2010, B pages.

(Continued)

*Primary Examiner* — Gollamudi Kishore
(74) *Attorney, Agent, or Firm* — Foley & Lardner LLP

(57) ABSTRACT

A novel pharmaceutical composition is provided by which nonsteroidal anti-inflammatory drugs (NSAIDs) are added directly to phospholipid-containing oil such as lecithin oils or to a bio-compatible oil to which an phospholipid has been added to make a NSAID-containing formulation that possess low gastrointestinal (GI) toxicity and enhanced therapeutic activity to treat or prevent inflammation, pain, fever, platelet aggregation, tissue ulcerations and/or other tissue disorders. The composition of the invention are in the form of a non-aqueous solution, paste, suspension, dispersion, colloidal suspension or in the form of an aqueous emulsion or microemulsion for internal, oral, direct or topical administration.

26 Claims, 19 Drawing Sheets

(51) Int. Cl.
| | |
|---|---|
| *A61K 9/107* | (2006.01) |
| *A61K 31/192* | (2006.01) |
| *A61K 31/195* | (2006.01) |
| *A61K 31/685* | (2006.01) |
| *A61K 31/405* | (2006.01) |
| *A61K 31/4152* | (2006.01) |
| *A61K 31/5415* | (2006.01) |
| *A61K 47/24* | (2006.01) |
| *A61K 31/167* | (2006.01) |
| *A61K 47/44* | (2006.01) |
| *A61K 47/48* | (2006.01) |

(52) U.S. Cl.
CPC ............ *A61K 31/167* (2013.01); *A61K 31/192* (2013.01); *A61K 31/195* (2013.01); *A61K 31/405* (2013.01); *A61K 31/4152* (2013.01); *A61K 31/5415* (2013.01); *A61K 31/616* (2013.01); *A61K 47/24* (2013.01); *A61K 47/44* (2013.01); *A61K 47/481* (2013.01)

(56) References Cited

U.S. PATENT DOCUMENTS

| | | | |
|---|---|---|---|
| 4,369,182 | A | 1/1983 | Ghyczy et al. |
| 4,421,747 | A | 12/1983 | Ghyczy et al. |
| 4,687,762 | A | 8/1987 | Fukushima et al. |
| 4,918,063 | A | 4/1990 | Lichtenberoer |
| 4,950,656 | A | 8/1990 | Lichtenberger |
| 5,032,585 | A | 7/1991 | Lichtenberger |
| 5,043,329 | A | 8/1991 | Lichtenberoer |
| 5,091,188 | A | 2/1992 | Haynes |
| 5,154,930 | A | 10/1992 | Popescu et al. |
| 5,213,804 | A | 5/1993 | Martin et al. |
| 5,229,422 | A | 7/1993 | Takahashi et al. |
| 5,314,909 | A | 5/1994 | Dolleruo |
| 5,505,960 | A | 4/1996 | Lucchetti et al. |
| 5,552,160 | A | 9/1996 | Liversidae et al. |
| 5,763,422 | A | 6/1998 | Lichtenberoer et al. |
| 5,807,541 | A | 9/1998 | Abero et al. |
| 5,916,591 | A | 6/1999 | Bierdel-Willkommen et al. |
| 5,955,451 | A | 9/1999 | Lichtenberger et al. |
| 5,993,846 | A | 11/1999 | Friedman et al. |
| 6,045,821 | A | 4/2000 | Garrity et al. |
| 6,096,336 | A | 8/2000 | Cao et al. |
| 6,120,800 | A | 9/2000 | Forssen et al. |
| 6,287,592 | B1 | 9/2001 | Dickinson |
| 2001/0012849 | A1 | 8/2001 | Wechter |
| 2002/0035264 | A1 | 3/2002 | Kararli et al. |
| 2004/0142880 | A1* | 7/2004 | Barbeau ............... 514/23 |
| 2012/0324784 | A1 | 12/2012 | Franklin et al. |
| 2013/0197250 | A1 | 8/2013 | Rongione et al. |
| 2013/0203773 | A1 | 8/2013 | Messerschmid et al. |
| 2014/0323429 | A1* | 10/2014 | Tei et al. ............... 514/53 |

FOREIGN PATENT DOCUMENTS

| | | |
|---|---|---|
| JP | 57108021 | 7/1982 |
| JP | 3-176425 | 7/1991 |
| JP | 3176425 | 7/1991 |
| WO | WO 96/22780 | 8/1996 |
| WO | WO 98/13073 | 4/1998 |
| WO | WO 00/02554 | 1/2000 |

OTHER PUBLICATIONS

Taiwan Patent Office, Official Action, S/N 98116729, Oct. 11, 2010, 14 pages (with translation).
Butler, B. D., et al. "Distribution of surfactants in the canine gastrointestinal tract and their ability to lubricate," Am. J. Physiol. 244: G645-G651, 1983.
Nasirideen, S., et al. "Naproxen incorporated lipid emulsions, Formulation and Stability Studies," Journal of Clinical Pharmacy and Therapeutics (1998) vol. 23, pp. 57-65.
Australian Patent Office, Official Action, S/N 2001297778, Feb. 16, 2006, 2 pages.
Australian Patent Office, Response to Official Action, S/N 2001297778, Aug. 22, 2006, 15 pages.
Australian Patent Office, Official Action, S/N 2001297778, Oct. 9, 2006, 2 pages.
Australian Patent Office, Response to Official Action, S/N 2001297778, May 4, 2007, 18 pages.
Australian Patent Office, Amendment, S/N 2001297778, Jun. 27, 2007, 15 pages.
Japanese Patent Office, Official Action, S/N 2002-582987, Apr. 15, 2008, 3 pages.
Japanese Patent Office, Response to Official Action (Argument in Japanese and amended claims in English), S/N 2002-582987, Aug. 11, 2008, 5 pages.
Japanese Patent Office, Official Action English translation only, S/N 2002-582987, Jul. 7, 2009, 2 pages.
Japanese Patent Office, Response to Official Action (Claims as amended in English), S/N 2002-582987, Nov. 6, 2009,23 pages.
Decision of Refusal, Japanese Patent Office, Jul. 7, 2009.
Japanese Patent Office, Appeal Brief, S/N 2002-582987, Jan. 12, 2010, 89 pages.
Indian Patent Office, Official Action, S/N 739/KOLNP/2003, Feb. 8, 2006, 12 pages.
Indian Patent Office, Response to Official Action, S/N 739/KOLNP/2003, Oct. 13, 2006, 38 pages.
Chinese Patent Office, Official Action, S/N 018223834, First Office Action, Apr. 1, 2005, 4 pages.
Chinese Patent Office, Response to Official Action (Proposed amended claims in English), S/N 018223834, Aug. 17, 2005, 6 pages.
Chinese Patent Office, Official Action, S/N 018223834, Aug. 18, 2006, 4 pages.
Chinese Patent Office, Response to Official Action (Proposed amennded claims in English), S/N 018223834, Jan. 4, 2007, 5 pages.
Chinese Patent Office, Official Action S/N 018223834 Nov. 9, 2007, 4 pages.
Chinese Patent Office, Response to Official Action (Proposed amended claims in English), S/N 018223834, Feb. 25, 2008, 5 pages.
Taiwan Patent Office, Official Action, S/N 91113158, Oct. 13, 2003, 2 pages.
Taiwan Patent Office, Official Action, S/N 91113158, Dec. 20, 2007, 10 pages.
Taiwan Patent Office, Response to Official Action (Proposed amended claims in English), S/N 91113158, Mar. 21, 2008, 18 pages.
Taiwan Patent Office, Response to Official Action (Proposed amended claims in English), S/N 91113158, May 20, 2009, 4 pages.
Canadian Patent Office, Official Action, S/N 2,143,606, May 17, 2008, 4 pages.
Canadian Patent Office, Response to Official Action, S/N 2,431,606, Nov. 27, 2008, 27 pages.
Canadian Patent Office, Official Action, S/N 2,431,606, May 28, 2009, 2 pages.
Canadian Patent Office, Response to Official Action, S/N 2,431,606, Nov. 27, 2009, 4 pages.
Israeli Patent Office, Official Action, S/N 156361, May 13, 2007, 6 pages.
Israeli Patent Office, Response to Official Action, S/N 156361, Dec. 15, 2007, 6 Pages.
Israeli Patent Office, Official Action, S/N 156361, Mar. 24, 2008, 4 Pages.
Israeli Patent Office, Response to Official Action, S/N 156361, Sep. 21, 2008, 13 Pages.
Israeli Patent Office, Response to Official Action, S/N 156361, Oct. 11, 2009, 59 Pages.
International Preliminary Examining Authority, Written Opinion, S/N PCT/US01/51605, Feb. 13, 2004, 5 pages.
Korean Patent Office, Official Action, S/N 10-2003-7008167, Nov. 2, 2007, 7 pages.
Korean Patent Office, Response to Official Action, S/N 10-2003-7008167, Mar. 3, 2008, 44 pages.
Korean Patent Office, Official Action, S/N 10-2003-7008167, May 23, 2008, 2 pages.

(56) References Cited

OTHER PUBLICATIONS

Korean Patent Office, Response to Official Action, S/N 10-2003-7008167, Sep. 23, 2008, 3 pages.
Singapore Patent Office, Amendment, S/N 200303264-6, Sep. 19, 2005, 4 pages.
European Patent Office, Official Communication, S/N 01273758.1, Aug. 24, 2004, 6 pages.
European Patent Office, Response to Official Communication, S/N 01273758. 1, Jan. 20, 2005, 16 pages.
European Patent Office, Official Action, S/N 01273758. 1, Aug. 17, 2005, 4 pages.
European Patent Office, Official Action, S/N 01273758.1, Apr. 18, 2006, 3 pages.
European Patent Office, Official Action, S/N 01273758. 1, Sep. 18, 2007, 7 pages.
European Patent Office, Response to Official Action, S/N 01273758. 1, Mar. 14, 2008, 15 pages.
European Patent Office, Response to Official Action, S/N 01273758. 1, Apr. 4, 2008, 79 pages.
United States Patent and Trademark Office, Office Action, U.S. Appl. No. 10/433,454, Mar. 16, 2010, 11 pages.
United States Patent and Trademark Office, Office Action, U.S. Appl. No. 10/433,454, Aug. 25, 2009, 9 pages.
United States Patent and Trademark Office, Office Action, U.S. Appl. No. 10/433,454, Mar. 5, 2009, 7 pages.
United States Patent and Trademark Office, Office Action, U.S. Appl. No. 10/433,454, Sep. 24, 2008, 6 pages.
United States Patent and Trademark Office, Office Action, U.S. Appl. No. 10/433,454, Mar. 26, 2008, 12 pages.
United States Patent and Trademark Office, Office Action, U.S. Appl. No. 10/433,454, Feb. 9, 2007, 9 pages.
Anand B.S., et al "Phospholipid Association Reduces the Gastric Mucosal Toxicity of Asprin in Human Subjects", The American Journal of Gastroenterology, vol. 94, No. 7, Jul. 1999, pp. 1818-1822.
Katare O.P., et al., "Proliposomes of Indomethacin for Oral Administration", Journal of Microencapsulation, vol. 8, No. 1, 1991, pp. 1-7.
Leyck, S., et al., "Improvement of the Gastric Tolerance of Non-Steroidal Anti-Inflammatory Drugs by Poyene Phosphatidylcholine (Phospholipon 100)", European Journal of Pharmacology, Amsterdam, NL, vol. 117, No. 1, Oct. 1985, pp. 35-42.
Lichtenberger L., et al., "Non-Steroidal Anti-Inflammatory Drugs (NSAIDS) Associate with Zwitterionic Phospholipids", Nature Medicine vol. 1, No. 2, Feb. 1, 1995, pp. 154-158.
Lichtenberger L., et al., "Phosphatidycholine Association Increases the Anti-inflammatory and Analgesic Activity of Ibuprofen in Acute and Chronic Rodent Models of Jount Inflammation" Journal of Pharmacology and Experimental Therapeutics, vol. 298, No. 1, Jul. 2001, pp. 2790287.
Furst DE, Paulus HE, Aspirin and other nonsteroidal anti-inflammatory drugs, In: Arthritis and Allied Conditions (McCarty DJ, Koopman WJ, Eds) Lea & Febiger, Philadelphia, 1993, pp. 567-602.
Pelletier J-P. Pathological pathways of osteoarthritis. In: Non-steroidal Anti-inflammatory Drugs: A Research and Clinical Perspective. Royal Society of Society of medicine Press, London, 1994, 1-14.
Jiang Y, Zhao J, Genant HK, Dequeker J, Geusens P, Bone mineral density and biomechanical properties of spine and femur of ovariectomized rats treated with naproxen. Bone 22: 509-514, 1996.
Walt R., Katschinski B, Logan R, Ashley J, Langman M. Rising frequency of ulcer perforation in elderly people in the United Kingdom. Lancet 489-492, 1986.
Allison MC, Howatson AG, Torrance CJ, Lee FD, Russel RI: Gastrointestinal damage associated with the use of nonsteroidal anti-inflammatory drugs. N. Enal J. Med. 327:749-754, 1992.
Kurata JR, Abbey DE. The effect of chronic aspirin use on duodenal and gastric ulcer hospitalizations. J. Clin. Gastroenterol. 12(3):260-266, 1990.
Svmmons DPM. Mortality in rheumatoid arthritis. Br. J. Rheum. 27 (Suppl 1): 44-54, 1988.

Henry DA, Johnston A, Dobson A, Duggal J. Fatal peptic ulcer complications and the use of non-steroidal anti- inflammatory drugs, aspirin and corticosteroids. Br. Med J. 295:1227-1229, 1987.
Vane JR. Inhibition of prostaglandin synthesis as a mechanism of action of aspirin-like drugs. Nature 231:232-251, 1971.
Ferreira SH Vane JR. New aspects of the mode of action of NSAIDs. Ann Rev Pharmacol 14:57-70, 1974.
Whittle BJR, Higgs GA, Eakin KE, Moncada S, Vane JR. Selective inhibition of prostaglandin production in inflammatory exudates and gastric mucosa. Nature 284:271-273, 1980.
Bergstrom S, Duner H, von Euler US, Pernow B, Sjovall J. Observations on the effects of infusions of prostaglandin E in man. Acta Physiol Scand. 45: 145-152, 1959.
Robert A. Nezamis JE, Lancaster C, Hanchar AJ: Cytoprotection by prostaglandins in rats: prevention of gastric necrosis produced by alcohol, HCL, NaOH, hypertonic, NaCl and thermal injury. Gastroenterology 70: 359-370, 1979.
Mitchell JA, Akarasreenont P, Thiemermann C, Flower RJ, Vane JR. Selectivity of NSAIDs as inhibitors of constitutive and inducible cyclo-oxvaenase. P.N.A.S. 90:11693-11697, 1993.
Masferrer JL, Zioeifel BS, Manning PT, Hauser SD, Leahy KM, Smith WG, Isakson PC, Seibert K. Selective inhibition of inducible cyclo-oxygenase-2 in vivo is anti-inflammatory and non-ulcerogenic. P.N.A.S. 91 :3228- 3232, 1994.
Xie W, Chipman JG, Robertson DL, Erikson RL, Simmons DL. Expression of a mitogen responsive gene encoding prostaqlandin synthesis is regulated by mRNA Splicing. P.N.A.S. 88: 2692-2696, 1991.
O'Banion MK, Sardowski HB, Winn V, Young DA. A serum and gluccorticoid regulated 4-kilobase RNA encodes a cyclooxygenase-related protein. J Biol Chem 266:23261-7, 1991.
Meade EA, Smith WL, Dewitt DL. Differential inhibition of prostaglandin endoperoxide synthase (cyclooxygenase) isozymes by asprin and other nonsteroidal anti-inflammatory drugs. J Biol Chem 268: 6610-6614, 1993.
Masferrer JL, Zioeifel BS, Manning PT, Hauser SD, Leahy KM, Smith WG, Isakson PC, Seibert K. Selective inhibition of inducible cyclo-oxygenase-2 in vivo is anti-inflammatory and non-ulcerogenic. P.N.A.S. 91:3228-3232, 1994. mRNA encodes a cyclooxygenase -related protein. J Biol Chem 1991; 266: 23261-7.
Lipsky PE, Isakson PC. Outcome of specific COX-2 inhibition in rheumatoid arthritis. J Rheumatol 24(Suppl 49): 9-14, 1997.
Bjarnason I, Macpherson A, Rotman H, Schupp, Hayllar J. A Randomized double-blind, cross-over study on the gastroduodenal tolerability of a highly specific cyclo-oxygenase-2 inhibitor, flosulide and naproxen. Scand J Gastroenterol 32: 126-13, 1997.
Simon LS, Lanza FL, Lipsky PE et. al. Preliminary safety and efficacy of SC-58635, a novel COX-2 inhibitor Arthritis Rheum 41: 1591-1602, 1998.
Laine L, Harper S, Simon T, Bath T, Johanson J, Schwartz H, Stem S, Quan H, Bolognese J. A randomized trial comparing the effect of Rofecoxib, a cyclogenase-2 specific inhibitor, with that of ibuprofen on the gastroduodenal mucosa of patients with osteoarthritis. Gastroenterology 117: 776-783, 1999.
Will super aspirin supersede aspirin Modern Drug Discovery May/ Jun. 54-59, 1999.
Ligumsky M, Grossman MI, Kauffman Jr GL. Endogenous gastric mucosal prostaglandins: their role in mucosal integrity. Am. J. Physiol. 242:G337-341, 1982.
Ligumsky M, Golanska EM, Hansen DG, Kauffman Jr GL. Asprin can inhibit gastric mucosal cyclo-oxygenase without causing lesions in the rat. Gastroenterology 84; 756-761, 1983.
Ligumsky M, Sestieri M, karmeli F, Zimmerman J, Okon E, Rachmilewitz D. Rectal administration of nonsteroidal anti-inflammatory drugs. Gastroenterology 98: 1245-1249, 1990.
Whittle BJR. Temporal relationship between cyclooxegenase inhibition, as measured by prostacyclin biosynthesis gastrointestinal damage induced by indomethacin in the rat. Gastroenterology 80:94-98, 1981.
Ivey KK, Paone DB, krause WI. Acute effect of systemic aspirin on gastric mucosa in man. Dig. Dis Sci 25: 97-99, 1980.

(56) References Cited

OTHER PUBLICATIONS

Konturek JW, Dembinski A, Konturek SJ, Stachura J, Domschke W, Infection of Helicobacter pylori in gastric adaptation to continued aspirin administration in human subjects. Gastroenterology 114: 245-255, 1998.
Langerbach R, Morham SG, Tiano HF, Loftin CD et. al. Prostaglandin synthase 1 gene disruption in mice reduces arachidonic acid-induced inflammation and indomethacin-induced gastric ulceration. Cell 83:483-492, 1995.
Morham SG, Langenbach R, Loftin CD et. al. Prostaglandin synthase 2 gene disruption causes severe renal pathology in the mouse. Cell 83: 473-482, 1995.
Mizuno H, Sakamoto C, Matsuda K et. al. Induction of COX-2 in gastric mucosal lesions and its inhibition by the specific antagonist delays healing in mice. Gastroenterology 112: 387-397, 1997.
Reuter BK, Asfaha S, Burel A, Sharkey KA, Wallace JL. Exacerbation of inflammation-associated colonic injury in rat through inhibition of cyclooxygenase-2. J Clin Invest 98: 2076-2085, 1996.
Wallace JL. Nonsteroidal anti-inflammatory drugs and gastroenteropathy: the second hundred years. Gastroenterology 112: 1000-1016, 1997.
Wallace JL, Keenan CM, Granger DN. Gastric ulceration induced by nonsteroidal anti-inflammatory drugs is a neutrophil-dependent process. Am J. Physiol 259: G462-467, 1990.
McCafferty D-M, Granger DN, Wallace JL. Indomethacin-induced gastric injury and leukocyte adherence in arthritic vs healthy rats. Gastroenterology 109; 1173-1180, 1995.
Mahmud T, Rati, SS, Scott, DL, Wrigglesworth JM, Bjarnason I. Nonsteroidal antiinflammatory drugs and uncouplina of mitochondrial oxidative phosphorylation. Arthritis Rheum 39: 1998-2003, 1996.
McCormack K, Brune K. Classical absorption theory and the development of gastric mucosal damage associated with non-steroidal anti-inflammatory drugs. Arch Toxicol 60: 261-269, 1987.
Lichtenberger, LM. The hydrophobic barrier properties of gastrointestinal mucus. Ann. Rev. Physiol. 57: 565- 583, 1995.
Hills BA, Butler BD, Lichtenberger LM. Gastric Mucosal Barrier: The hydrophobic lining to the lumen of the stomach. Am. J. Phvsiol.: Gastrointestinal and Liver Physiology 7:G561-68, 1983.
Lichtenberger LM, Graziani LA, Dial EJ, ButlerBD, Hills BA. Role of surface-active phospholipids in gastric cytoprotection. Science 219:1327-29, 1983.
Spychal RT, Marrero JM, Saverymuttu SH, Northfield TC. Measurement of the surface hydrophobicity of human gastrointestinal mucosa. Gastroenterology 97: 104-11, 1989.
Go MF, Lew GM, Lichtenberger LM, Genta RM, Graham DY. Gastric mucosal hydrophobicity and Helicobacter pylori: response to antimicrobial therapy. Am J Gastroenterology 88: 1362-65, 1993.
Butler BD, Lichtenberger LM, Hills BA. Distribution of surfactants in the canine GI tract and their ability to lubricate. Am. J. Physiol: Gastointestinal and Liver Physiology 7:G645-51, 1983.
Kao Y-CJ, Lichtenberger LM. A method to preserve extracellular surfactant-like phospholipids on the luminal surface of the rodent gastric mucosa. J. Histochem. Cytochem. 38:427-31,1990.
Kao Y-CJ, Lichtenberger LM. Phospholipid- and neutral-lipid-containing organelles of rat gastroduodenal mucous cells. Gastroenterology 101:7-21, 1991.
Goddard PI, Lichtenberger LM. Does aspirin damage the canine gastric mucosa by reducing its surface hydrophobicity? Am. J. Physiology: Gastrointestinal and Liver Physiology 15: G421-30, 1987.
Goddard PJ, Kao Y-CJ, Lichtenberger LM. Luminal surface hydrophobicity of canine gastric mucosa is dependent on a surface mucous gel. Gastroenterology 98:361-70, 1990.
Dial EJ, Lichtenberger LM. A role for milk phospholipids in protection against gastric acid. Gastroenterology 87: 379-385, 1984.
Lichtenberger LM, Romero JJ, Kao Y-C, Dial EJ. Gastric protective activity of mixtures of saturated polar and neutral lipids in rats. Gastroenterology 99;311-326, 1990.
Lichtenberger LM, Wang Z-M, Romero JJ, Ulloa C, Perez JC, Giraud M-N, Barreto JC. Non-steroidal anti-inflammatory drugs (NSAIDs) associate with zwitterionic phospholipids: Insight into the mechanism and reversal of NSAID-induced gastrointestinal injury. Nature Medicine 1: 154-158, 1995.
Anand BS, Romero JI, Sanduja SK, Lichtenberger LM: Phospholipid association reduces the gastric toxicity of aspirin in human subjects. Am J Gastroenterol 94: 1818-1822, 1999.
Lichtenberger LM, Ulloa C, Vanous AL, Romero JJ, Dial EJ, Illich PA, Walters ET. Zwitterionic phospholipids enhance aspirin's therapeutic activity, as demonstrated in rodent model systems. JPET 1996; 277:1221-1227.
Randall LO, Selitto JJ. A method for measurment of analgesic activity of inflamed tissue. Arch. Int. Pharmacodyn. 111: 409-411, 1957.0.
Faden, A.I., Experimental neurobiology of central nervous system trauma. Grit Rev Neurobiol, 1993. 7(3-4): p. 175-86.
Rogers, J., et al., Inflammation and Alzheimer's disease pathogenesis. Neurobiol Aging, 1996.17(5): p. 681-6.
Hains, B.C., J.A. Yucra, and C.E. Hulsebosch, Reduction of pathological and behavioral deficits following spinal cord contusion injury with the selective cyclooxygenase-2 inhibitor NS-398. J Neurotrauma, 2001. 18(4): p. 409-23.
Stewart, W.F., et al., Risk of Alzheimer's disease and duration of NSAID use, Neurology, 1997. 48(3): p. 626-32.
Gabriel, S.E., L. Jaakkimainen, and C. Bombardier, Risk for serious gastrointestinal complications related to use of nonsteroidal anti-inflammatory drugs. A meta-analvsis. Ann Intern Med, 1991. 115(10): o. 787-96.
Lichtenberger, L.M., et al., Non-steroidal anti-inflammatory drugs (NSAIDs) associate with zwitterionic phospholipids: insight into the mechanism and reversal of NSAID-induced gastrointestinal injury. Nat Med, 1995. 1(2): p. 154-8.
Anand, B.S., et al., Phospholipid association reduces the gastric mucosal toxicity of asprin in human subjects, Am J Gastroenterol, 1999. 94(7): p. 1818-22.
Lichtenberger, L.M., et al., Zwitterionic phospholipids enhance aspirin's therapeutic activity, as demonstrated in rodent model systems. J Pharmacol Exp Ther, 1996. 277(3): p. 1221-7.
Lichtenberger, L.M., et al., Phosphatidylcholine association increases the anti-inflammatory and analgesic activity of ibuprofen in acute and chronic rodent models of joint inflammation: relationship to alterations in bioavailability and cyclooxygenase-inhibitory potency. J Pharmacol Exp Ther, 2001. 298(1): p. 279-87.
Clatworthy, A.L., et al., Role of peri-axonal inflammation in the development of thermal hyperalgesia and guarding behavior in a rat model of neuropathic pain. Neurosci Lett, 1995. 184(1): p. 5-8.
Coggeshall, R.E., et al., Is large myelinated fiber loss associated with hyperalgesia in a model of experimental peripheral neuropathy in the rat? Pain, 1993. 52(2): p. 233-42.
Carlson, S.L., et al., Acute inflammatory response in spinal cord following impact injury. Exp Neural, 1998. 15111): pp. 77-88.
Hirst, W.D., et al., Expression of COX-2 by normal and reactive astrocytes in the adult rat central nervous system. Mol Cell Neurosci, 1999. 13(1): pp. 57-68.
Resnick, D.K., et al., Role of cyclooxygenase 2 in acute spinal cord injury. J Neurotrauma, 1998. 15(12): p. 1005-13.
Plunkett, J.A., et al., Effects ofinterleukin-10 (IL-10) on pain behavior and gene expression following excitotoxic soinal cord iniury in the rat. Exp Neural, 2001. 168(1): p. 144-54.
Basso, D.M., M.S. Beattie, and J.C. Bresnahan, A sensitive and reliable locomotor rating scale for open field testina in rats. J Neurotrauma, 1995. 12(1): p. 1-21.
Grill, R., et al., Cellular delivery of neurotrophin-3 promotes corticospinal axonal growth and partial functional recovery after spinal cord injury. J Neurosci, 1997. 17(14): p. 5560-72.
Rabchevsky, A.G., et al., Cyclosporin a treatment following spinal cord injury to the rat: behavioral effects and stereological assessment of tissue sparing. J Neurotrauma, 2001. 1815): p. 513-22.
Hsiao, K., et al., Correlative memory deficits, Abeta elevation, and amyloid plaques in transgenic mice. Science, 1996. 274(5284): pp. 99-102.
Hsiao, K., Transgenic mice expressing Alzheimer amyloid precursor proteins. Exp Gerontol, 1998. 33(7-8): p. 883-9.

(56) References Cited

OTHER PUBLICATIONS

Lim, G.P., et al., Ibuprofen suppresses plaque pathology and inflammation in a mouse model for Alzheimer's disease. J Neurosci, 2000. 20(15): p. 5709-14.
Morris, R., Developments of a water-maze procedure for studying spatial learning in the rat. J Neurosci Met, 1984.1111): p. 47-60.
Lichtenberger, L.M., R Darling, and J.J. Romero, Effect of luminal damaging agents on the gastric mucosal barrier and prostaglandin metabolism in cyclooxygenase (COX) knockout mice. Gastroenterology, 2001. 120: p. A-143.
Wu KK. Thrombogenesis, Atherogenesis and Hypercoagulability in "Thromboembolic Disorders" edited by Wu KK. PSG Publisher, Littleton, Mass, 1984, pp. 5-18.
Schafer AI, Handin RI. The role of platelets in thrombotic and vascular disease. Progr Cardiovasc Dis 22:31, 1979.
Fuster V, Chesbro JH. Platelet inhibitor drugs in management of arterial thromboembolic and atherosclerotic disease. Mavo Clinic Proc. 56:265, 1981.
Fields WS, Lemak: NA, Frankowsk RF, Hardy RJ. Controlled trial of aspirin in cerebral ischemia Stroke 8:301-314, 1977.
Canadian Cooperative Study Group. A randomized trial of aspirin and sulfide pyrazone in threatened stroke, New Eno J Med 299:53-59, 1978.
Lewis HD Jr, Davis JW, Arclirbald DO, et al. Protective effects of aspirin against acute myocardial infarction and death in man with unstable anginas. Results of a VA cooperative study. N Eng J Med 313: 396, 1983.
The Steering Committee of the Physicians Health Study Research Group Preliminary Report: Findings from the aspirin component of the ongoing physicians health study. N Eng. J Med 318:362, 1988.
Cryer B, Feldman M. Effects of very low dose daily, long term asprin therapyon gastric, duodenal, and rectal prostaglandin levels and on mucosa! injury. Gastroenterology 117: 17-25, 1999.
Vane J. Towards a better aspirin. Nature 367:215-216, 1994.
Triplett DA, Harms CS, Newhouse P, Clark C. Platelet Function: Laboratory evaluation and clinical application. Edited by Triolett DA. American Society of Clinical Pathologists, Chicago, 1978.
Sanduja SK, Mehta K, Xu X-M, Sanduja R and Wu KK. Differentiation associated expression of prostaglandin H and thromboxane A synthases in monocytoid cell lines. Blood 78:3178-3185, 1991.
Sanduja SK, Tsai AL, Aleksic NM, Wu, K.K. Kinetic of Prostacyclin Synthesis in PGHS-1 Overexpressed Endothelial cells. Am.J. Physiol. 267: C1459-1466, 1994.
Gambino MC, Cerletti C, Marchi S, Garattini S, Gaetano GD. How intravenous administration of low dose aspirin inhibits both vascular and platelet cyclooxygenase activity: an experimental study in the rats. Expt Bio Med 182:287, 1986.
Pierangeli SS, Barker JH, Stikovac D, Ackerman D, Anderson G, Barquinero J, Acland R, Harris EN. Effect of human IgG antiphospholipid antibodies on an in vivo thrombosis model in mice. Thromb Haemost 71: 670-674, 1994.
Edwards:MH, Pierangeli S, Liu X, Barker JH, Anderson G, Harris EN. Hydroxychloroquine reverses thrombogenic antibodies in mice. Circulation 96: 4380-4384, 1997.
Pierangeli SS, Liu X, Antonov IT, Sparrow IT, Harris EN, Myones BL. Induction of pathogenic anticardiolipin antibodies in a murine model. Arthritis Rheum 41: S135, 1998.
Myones BL, Antonov IV, Fedorova U, Volgin AY, Liu X, Espinola R, Harris EN, Pierangeli SS. Complexes of protein and saturated cardiolipin are capable of binding antiphospholipid antibodies and inducing thrombogenic antiphospholipid antibodies in a murine model, Arthritis Rheum 42: S369, 1999.
Smith WL, DeWitt DL. Biochemistry of prostaglandin endoperoxide H synthase-1 and synthase-2 and their differential susceptibility to non-steroidal anti-inflammatory drugs. seminars in Nephro. 15:179, 1995.
Rome LH, Lands WEM. Structure requirements for time dependent inhibition of prostaglandin biosynthesis by anti-inflammatory drugs. Proc Natl Acad Sci USA 72:4863-4865, 1975.
Laneuville 0, Breuer DK, DeWitt DL et. ale Differential inhibition of human prostaglandin endoperxide H synthase-1 and -2 by non-steroidal anti-inflammatory drugs. J Pharm Exp Ther 271 :927-934, 1994.
Vane JR. Inhibition of prostaglandin synthesis as a mechanism of action of aspirin-like drugs. Nature 231 :232, 1971.
Roth GI, Majerus PW. The mechanism of the effect of aspirin on human platelets I. Acetylation of a particular fraction protein. J Clin. Invest 56:624-632, 1975.
Hennekens CH, Buring JE. Aspirin and cardiovascular disease. Bull NY Acad Med 65:57-68, 1989.
Viinikka L. Acetylsalicylic acid and the balance between prostacyclin and thromboxane. Scand J Clin Lab Invest 50(supple 201): 103, 1990.
Lekstrom JA, Bell WR. Aspirin in the prevention of thrombosis. Med 70:161, 1991.
Gabriel SE, Fehring RA. Trends in the utilization of non-steroidal anti-inflammatory drugs in the United States, 1986-1990. J Clin Epidemiol 45: 1041-1044, 1992.
Keifer DM; A century of pain relief. Todays Chemist at Work, Dec. 38-42, 1997.
Gabriel SE, Jaakkimainen R, Bombardier C. Risk for serious gastrointestinal complications related to the use of nonsteroidal anti-inflammatory drugs. Ann Int Med 115: 787-796, 1991.
Lichtenberger LM, Wang ZM, Romero JJ, Ulloa C, Perez J, Giraud M-N, Barreto JC. NSAIDs associate with zwitterionic phospholipids: Insight into the mechanism and reversal of NSAID-induced G.I. injury. Nature Medicine 1:154-158, 1995.
Anand BS, Romero JJ, Sanduja SK, Lichtenberger LM. Evidence that phospholipid reduces the gastric toxicity of aspirin in human subjects. Am J Gastroenterol 94: 1818-1822, 1999.
Lichtenberger LM, Ulloa C, Vanous AL, Romero JJ, Dial EJ, Illich PA, Walters ET. Zwitterionic phospholipids enhance aspirin's therapeutic activity, as demonstrated in rodent model systems. J Pharm Exp Therap 227:1221-1227, 1996.
Benedict CR, Refino CJ, Keyt BA, Pakala R, Paoni NF, Thomas R, Bennett WF. New variant of human tissue plasminigen activator (TPA) with enhanced efficacy and lower incidence of bleeding compared with recombinant human TPA. Circulation 92: 3032-3040, 1995.
Blake PR, Summers MF. NOESY-1-1 Ech spectroscopy with eliminated radiation damping. J Magn. Res 86: 622-625, 1990.
Pinon JF. In vivo study of platelet aggregation in rats. J Pharmaco. Methods 12:79, 1984.
Fernandez, A.G. et al., "Aspirin, Salicylate and Gastrointestinal Injury," Nature Medicine, Vol. 1, No. 7, Jul. 1995, pp. 602-603.
Negative Assessment Appeal filed in Brazilian Patent Application No. PI 0116380-9 dated Mar. 30, 2012, 27 pages.
English translation of the Oct. 31, 2011 Response to an Office Action mailed by the Japanese Patent Office for Japanese Patent Application No. 2002-582987.
Googman & Gillman's Manual of Pharmacology and Therapeutics, 12th Edition, Section IV, Inflammation, Immunomodulation, and Analgesic Agents: Pharmacotherapy of Gout, Nonsteroid-Anti-inflammatory Drugs; Figure 34-1; 1999.
English Translation of a Response as filed with the Brazilian Patent Office on Aug. 8, 2011, 11 pages.
Response as filed with the Brazilian Patent Office on Aug. 8, 2011, 14 pages.
English translation of the Japanese Questioning inJapanese Patene Application No. 2002-682987, dated Aug. 2, 2011.
English Translation of JP 61194015, 14 pages.
English Translation of Brazilian Examination Report, Lenard Lichtenberger, "Method and Compositions Using Lecithin Oil Formulations and Non-Steroidal Anti-Inflammatory Drugs (NSAIDs) to Protect the Gastrointestinal Tract and Provide Greater Therapeutic Activity," Application No. PI 0116380-9, PCT/US01/51605, filing date Dec. 19, 2001, 14 pages.
Byron Cryer, MD, et al., Low-Dose Aspirin-Induced Ulceration is Attenuated by Asprin-Phosphatidylcholine: A Randomized Clinical Trial, The American Journal of Gastroenterology, Nov. 16, 2010, pp. 1-6.

(56) References Cited

OTHER PUBLICATIONS

Response to Office Action including Application for Amendment and Amended Application regarding Taiwan Appln. No. 98116729, filed Apr. 13, 2011.

Observation filed in Response to Notice of Reexamination filed in China on Feb. 28, 11 for Chinese Application 01822383.4 (2011).

Decision of Reexamination from the Chinese Patent Office issued on Mar. 24, 2011 in Chinese Application 01822383.4.

Chinese Patent Office, Notification of Reexamination, S/N 018223834, Nov. 11, 2010, 7 pages.

Decision of Final Rejection issued in related Chinese Patent Application No. 201110165238.6, dated Oct. 9, 2013.

U.S. Appl. No. 12/883,918 Office Action dated Aug. 16, 2013.

U.S. Appl. No. 12/883,918, Office Action dated May 21, 2013.

U.S. Appl. No. 12/883,902, Office Action dated Jan. 1, 2014.

Notice of Allowance issued in related U.S. Appl. No. 12/883,902, dated Apr. 6, 2015.

* cited by examiner

Recovery of Motor Function after Spinal Cord Injury (SCI, assessed by the BBB[a] Test) in Rats Treated with Saline, Ibuprofen and PC-Ibuprofen

[a]Basso, Beattie, Bresnahan

COMPOSITIONS COMPRISING LECITHIN OILS AND NSAIDS FOR PROTECTING THE GASTROINTESTINAL TRACT AND PROVIDING ENHANCED THERAPEUTIC ACTIVITY

CROSS REFERENCE TO RELATED APPLICATIONS

This application is a continuation of U.S. patent application Ser. No. 12/883,873, filed Sep. 16, 2010, which is a continuation of U.S. patent application Ser. No. 10/433,454, having a 35 U.S.C. §371(c) date of Nov. 6, 2003, which is a U.S. National Phase Application of International Patent Application No. PCT/US2001/051605, filed Dec. 19, 2001, which claims the benefit of U.S. Provisional Patent Application No. 60/256,711, filed Dec. 19, 2000. The contents of these applications are incorporated herein by reference in their entireties.

BACKGROUND OF THE INVENTION

1. Field of the Invention

The present invention relates to unique compositions including a bio-compatible oil and a non-steroidal anti-inflammatory drugs (NSAID), where the oil or a constituent thereof is effective in reducing GI toxicity of the NSAID and enhancing the drugs' therapeutic activity to treat inflammation, pain, fever and thrombosis as well as other diseases such as; stroke, traumatic brain injury, spinal chord injury, cardiovascular disease, ovarian cancer, colon cancer, Alzheimer's disease, arthritis, uveitis, and mucositis.

More particularly, the present invention relates to formulations in which a NSAID is admixed as a powder directly into a bio-compatible oil including a phospholipid to form a medication which can be a solution, a paste, a semi-solid, a dispersion, a suspension, a colloidal or mixtures thereof, where the medication can be administered internally, orally and/or topically.

2. Description of the Related Art

NSAIDs constitute a family of compounds, the first of which to be discovered being aspirin, that have the capacity to inhibit a number of biological pathogenic processes including; fever, inflammation, pain, thrombosis and carcinogenesis.[1] As a direct consequence of their great therapeutic potential, NSAIDs are heavily consumed among the world's populace as both over-the-counter and prescription drugs. Because of their great utility, a significant percentage of our populace consume NSAIDs with regularity including: the 30-40 millions Americans who are afflicted with rheumatoid or osteoarthritis; and countless others that take the medication to treat/prevent: inflammation and pain caused by other inflammatory conditions or injury, the pain of dysmenorrhea; fever; the development of thrombosis and related cardiovascular diseases; ovarian cancer, colon cancer and Alzheimer's Disease.[1,2] The problem with the trend of ever-increasing NSAID usage, especially among the elderly, is that these drugs commonly induce gastrointestinal (GI) side-effects.[3-6]

In the stomach and small intestine the drugs cause dyspepsia (gastric distress, heartburn, bloating or nausea), erosions, gastritis/duodenitis and ulcers in some individuals. Gastrointestinal bleeding may also occur in NSAID users that can result in episodes of anemia (of variable severity), or hemorrhage—that may be life-threatening, in the most serious cases.[7,8] One or more of these GI complications have been estimated to occur in 20-40% of regular NSAID users. Given the large NSAID market, even infrequent GI complications send an estimated 76,000 Americans to the hospital and kill estimated 7,600 annually.

One of the major contributions to the understanding of NSAID action came from the pioneering studies of Vane and associates in the early 1970's that reported that chemically dissimilar members of the NSAID family share the ability to inhibit the activity of the enzyme, cyclooxgenase (COX) that catalyzes the conversion of arachidonic acid to prostaglandin $G_2$ and $H_2$ by sequential steps of oxidation and peroxidation.[9-11] Prostaglandin $H_2$ will then be converted to one of several eicosanoids in a target cell by a process catalyzed by specific prostaglandin synthases. Thus, by reversibly or irreversibly inhibiting COX activity, NSAIDs could deplete a particular tissue or cellular fluid of prostaglandins, which has been demonstrated to promote tissue inflammation.[12] Shortly after these revelations, Robert and his associates at the Upjohn Company demonstrated that certain classes of prostaglandins shared the remarkable property of protecting the GI epithelium from a number of ulcerogenic compounds and/or conditions, demonstrating the "cytoprotective" nature of these lipid mediators.[13] Based upon these two major contributions, it was concluded that NSAIDs induce injury and ulceration to the GI epithelium by inhibiting mucosal COX activity and depleting the tissue of "cytoprotective" prostaglandins.

The next and most recent development in our understanding of arachidonic metabolism came in the early 1990's, when a number of investigators[14-18] identified and cloned a second COX isozyme (now called COX-2), that was structurally and functionally related to the originally described enzyme (now called COX-1). In contrast to COX-1, which is constitutively expressed in most tissues including the GI mucosa, COX-2 was demonstrated to be inducible, primarily by cytokines and other mediators of inflammation. Based on these findings, together with evidence that COX-2 is selectively expressed at sites of inflammation, and is expressed at low or undetectable levels in non-inflamed GI mucosa,[19-23] a number of pharmaceutical houses initiated the development of compounds that selectively inhibited COX-2.

This effort culminated in the launching of the first two COX-2 selective inhibitors, Celebrex (Celecoxib) and Vioxx (Rofecoxib). The pre-clinical and clinical data released to date have indicated that these compounds are therapeutically effective and have a low toxicity to the GI mucosa. This news has led to great excitement in both the medical and lay communities, which has translated into record number prescriptions of Celebrex and Vioxx being filled the first two years these drugs were on the market.[24]

A major concern of the inventor and a number of other investigators studying NSAID-induced GI injury, is that the linkage between COX inhibition and GI injury and bleeding is not very strong. For example, Ligumsky and associates in the early 1980's published a series of papers in rats and dogs that appeared to dissociate COX inhibition from mucosal injury.[25-27] Initially they demonstrated that the aspirin and its metabolite, salicylic acid had equivalent ability to induce injury to the canine gastric mucosa, even though aspirin depleted the tissue of "cytoprotective" prostaglandins, whereas salicylic acid displayed no COX inhibitory activity.[25] In subsequent rodent studies, it was demonstrated that mucosal COX activity was inhibited by >90% regardless if aspirin was administered subcutaneously or intragastrically, although ulcerations only formed in the stomachs of rats when the NSAID was administered intragastrically.[26,27] Whittle also reported a dissociation between indomethacin's effect to induce COX inhibition and mucosal injury in the small intestine, as intestinal lesions only begin to develop 48 hrs after NSAID administration, at a time point where COX activity (which is fully inhibited<3 hrs, post-indomethacin) has returned to normal.[28]

It should be pointed out that the evidence suggesting that mucosal COX inhibition may not be directly involved in the pathogenesis of NSAID—induced enteropathy—is also supported by some clinical studies, which have reported that i.v. administration of aspirin did not cause detectable histological injury to the human gastric mucosa, in contrast to oral administration of the NSAID.[29] It was also reported that after 2-4 weeks of NSAID treatment the human gastric mucosa becomes resistant to the injurious actions of oral aspirin or indomethacin, and that this adaptive response is not linked to a recovery of COX activity which remains fully blocked during the study period.[30]

Lastly, the hypothesis that NSAIDs induce GI injury, primarily by inhibiting mucosal COX-1 predicts that mice deficient in the isozyme, due to targeted gene disruption, would be prone to the development of spontaneous mucosal ulcers and be more sensitive to NSAIDs than their wild type littermates. Langenbach and associates[31] have reported that COX-1 null animals have no detectable GI disease and if anything are more resistant to indomethacin—induced ulcer development. To make matters more confusing, Morham et al.[32] have reported in a subsequent study that COX-2 knockout mice are not viable and frequently succumb to peritonitis as well as renal disease. The possibility that COX-2 inhibition may be detrimental, has also been supported by a number of animal studies that indicate that the healing of ulcers in the proximal and distal gut is exacerbated if animals are treated with selective COX-2 blockers.[33, 34] Similar complications in humans have not been reported to date.

Based on the evidence documented above, a compelling case can be made to investigate, other mechanisms by which NSAIDs may induce GI mucosal injury, and how this information can be used in the development of alternative strategies to reduce or prevent the GI toxicity of these compounds. Other potential targets of NSAID—induced gastro-enteropathy—are the ability of these drugs to: reduce mucosal blood flow and induce leukocyte adherence to the vascular wall; uncouple oxidative phosphorylation; induce cellular acidification due to their protonophore characteristics; and to attenuate the hydrophobic, non-wettable characteristics of the mucosa, thereby increasing the tissue's susceptibility to luminal acid.[35-40] It is this latter property which has been the focus of the inventor's laboratory over the past 15-20 years.

In 1983, the inventor's laboratory made the initial observation that canine gastric mucosa had a uniquely hydrophobic surface, as determined by contact angle analysis.[41, 42] Since then his and other laboratories have demonstrated that this non-wettable surface property of the gastric mucosa is found in a number of other species including rodents and man.[40,43,44] Furthermore, both biochemical and morphological techniques were employed to demonstrate that this property may be attributable to an extracellular lining of surfactant-like phospholipid within and coating the mucus gel layer.[45-47] The inventor's laboratory also observed that many agents that damage the gastric mucosa, including NSAIDs, have the capacity to rapidly transform the tissue from a non-wettable (hydrophobic) to a wettable (hydrophilic) state, and that this injurious action could be attenuated by the administration of synthetic or purified phospholipids.[48-51]

In recent years, research has focused on the mechanism of NSAID—phospholipid interaction. In these studies, the inventor's laboratory have obtained compelling evidence that NSAIDs may induce mucosal injury by chemically associating with the zwitterionic phospholipids, such as phosphatidylcholine (PC) within and on the surface of the mucus gel layer, with the site of electrostatic binding being between the positively-charged choline head group of zwitterionic phospholipid, phosphatidylcholine (PC) and the negatively charged (carboxyl or sulfonyl) group of the NSAID.[52] Based upon this information, our group evaluated the GI toxicity of a number of NSAIDs that were chemically pre-associated with synthetic or purified PC, prior to administration, and obtained evidence that these novel drugs were far less injurious, with regards to GI lesion formation and bleeding than the unmodified NSAIDs, in the rat. The applicability of this approach to human disease was recently confirmed when pilot clinical studies revealed that PC—aspirin, employing purified (93% pure) PC, induced significantly fewer gastric lesions in human subjects than unmodified aspirin over a 4 day period, in a pilot double blind, cross-over study.[53]

Interestingly, the inventor's laboratory also determined that PC-NSAIDs have superior therapeutic efficacy and potency to the unmodified drugs in animal models of fever, inflammation/pain, thrombosis and osteoporosis indicating that their lower gastric toxicity could not be simply explained by a reduction in bioavailability.[52,54]

Although the combination of PC (other of similar phospholipids) and NSAIDs result in reduced pathogenic effects of NSAID administration, oral administration of these combinations have been less than adequate because the combination requires a larger volume per effective dose than NSAID alone. Thus, there is a need in the art for a composition of NSAID and carrier that allows for increased NSAID concentration in the composition and where the carrier reduces the pathogenic effects of NSAIDs and is in a form that is amenable to administration orally, internally or topically. Moreover, there is a need in the art for an NSAID composition which has improved self-life, especially for aspirin-containing medicaments.

SUMMARY OF THE INVENTION

General Compositions

The present invention provides a composition including a relatively high concentration of a non-steroidal anti-inflammatory drugs (NSAID) in a non-aqueous, fluid carrier.

The present invention provides a composition of an NSAID in non-aqueous, fluid carrier, where the carrier comprises a bio-compatible oil and a phospholipid.

The present invention provides a composition of an NSAID in non-aqueous, fluid carrier, where the carrier comprises a phospholipid rich bio-compatible oil.

The present invention also provides a composition including a relatively high concentration of an NSAID in a non-aqueous, fluid carrier, where the carrier or constituents thereof act to reduce the pathogenic effects of the NSAID, to increase the bioavailability of the NSAID, and to increase NSAID availability across relatively hydrophobic barriers in an animal including a human.

The present invention also provides a composition including a relatively high concentration of an NSAID, a phospholipid in a non-aqueous, fluid carrier, where the phospholipid is present in an amount sufficient to reduce the pathogenic effects of the NSAID, to increase the bioavailability of the NSAID, and to increase NSAID availability across relatively hydrophobic barriers in an animal including a human.

The present invention provides a composition including a relatively high concentration of an NSAID in a non-aqueous, fluid carrier comprising a phospholipid and a bio-compatible oil, where the phospholipid is present in an amount sufficient to reduce the pathogenic effects of the NSAID, to increase the bioavailability of the NSAID, and to increase NSAID availability across relatively hydrophobic barriers in an animal including a human.

The presence of the phospholipid also reduces general pathogenic and/or toxicity of the NSAID. Thus, the phospholipid reduce and/or prevent liver damage due to the administration of acetaminophen and/or kidney and/or cardiovascular side-effect due to the administration of other NSAIDs such as ibuprofen or the COX-2 inhibitors.

General Methods for Making the General Compositions

The present invention also provides a method of preparing a composition comprising an NSAID in a non-aqueous, fluid carrier comprising the step of combining the NSAID with the carrier to form a solution, a paste, a semi-solid, a dispersion, a suspension, a colloidal suspension or a mixture thereof.

The present invention also provides a method of preparing a composition comprising an NSAID in a non-aqueous, fluid carrier including a phospholipid comprising the step of combining the NSAID with the carrier to form a solution, a paste, a semi-solid, a dispersion, a suspension, colloidal suspension or mixtures thereof comprising phospholipid-NSAID association complex.

The present invention also provides a method of preparing a composition comprising an NSAID in a non-aqueous, fluid carrier including a phosphatidylcholine-containing bio-compatible oil comprising the step of combining the NSAID with the carrier to form a solution, a paste, a semi-solid, a dispersion, a suspension, a colloidal suspension or a mixture thereof comprising phosphatidylcholine-NSAID associated complex.

The present invention also provides a method of preparing a composition comprising an NSAID in a non-aqueous, fluid carrier comprising the step of combining the NSAID with the carrier to form a solution, a paste, a semi-solid, a dispersion, a suspension, a colloidal suspension or a mixture thereof where the carrier comprises a phospholipid-containing bio-compatible oil or a bio-compatible oil and a phospholipid or a mixture thereof.

Emulsified Compositions

The present invention also provides an aqueous emulsion of a composition including a non-aqueous carrier, where the carrier includes a bio-compatible oil, a phospholipid in an amount sufficient to produce a therapeutically beneficial effect and zero to a therapeutically effective amount of an NSAID and when the NSAID is present, the amount of phospholipid is also sufficient to reduce the pathogenic effects of the NSAID. The aqueous emulsion can also include bio-compatible emulsifying agents to maintain the composition in a state of emulsion for extended periods of time. Preferably, a particle size of the emulsified composition is sufficiently small to allow the composition to be taken orally or to be injected into a tissue or organ site without causing adverse effect. For i.v. or i.a. injectable forms, microemulsions are preferred, where the average particle size can be reduced to between 0.5 and about 10 µm, and preferably, between about 1 and 5 µm.

The present invention also provides an aqueous microemulsion of a composition including an non-aqueous carrier, where the carrier includes a bio-compatible oil, a phospholipid in an amount sufficient to produce a therapeutically beneficial effect and zero to a therapeutically effective amount of a NSAID and when the NSAID is present, the amount of phospholipid is also sufficient to reduce the pathogenic effects of the NSAID. The aqueous emulsion can also include bio-compatible emulsifying agents to maintain the composition in a state of emulsion for extended periods of time.

Method for Making Emulsified Compositions

The present invention also provides a method for preparing an aqueous emulsion of this invention including the step of adding a given amount of a desired non-aqueous composition of this invention to an aqueous solution in the absence or presence of an emulsifying agent and mixing the composition and the solution for a time sufficient to form an emulsion, where the emulsifying agent, when present, is present in an amount sufficient to form a stable emulsion.

The present invention also provides a method for preparing an aqueous microemulsion of this invention including the step of adding a given amount of a desired non-aqueous composition of this invention to an aqueous solution in the absence or presence of an emulsifying agent, mixing the composition and solution for a time sufficient to form an emulsion, and shearing the emulsion under microemulsifying conditions to form a microemulsion, where the emulsifying agent, when present, is present in an amount sufficient to form a stable microemulsion.

The reason the emulsifying agent is optional is because the phospholipid themselves have some emulsifying properties.

Compositions for Treating Inflammation

The present invention also provides a composition for reducing tissue inflammation including a non-aqueous carrier including a therapeutically effective amount of an NSAID and a sufficient amount of a phospholipid to reduce the pathogenic effects of the NSAID, where the composition reduces tissue inflammation at an NSAID dose below a dose typically required to illicit the same therapeutic response in the absence of the phospholipid with decreased mucosal toxicity and/or irritation.

The present invention also provides a after surgical treatment for reducing tissue, organ and/or incision inflammation and other consequences thereof, where the composition includes a non-aqueous carrier including a therapeutically effective amount of an NSAID and a sufficient amount of a phospholipid to reduce the pathogenic effects of the NSAID or where the composition includes or an aqueous solution into which the non-aqueous carrier composition is dispersed (e.g., an emulsion or microemulsion), where the composition reduces tissue inflammation at an NSAID dose below a dose typically required to illicit the same therapeutic response in the absence of the phospholipid with decreased mucosal toxicity and/or irritation. Of course, the composition can be an ointment, a spray, coated on a wipe, coated on a biodegradable substrate or the like.

Composition for Treating Platelet Aggregation

The present invention also provides a composition for reducing platelet aggregation including a non-aqueous carrier including a therapeutically effective amount of an NSAID and a sufficient amount of a phospholipid to reduce the pathogenic effects of the NSAID or an aqueous solution into which the non-aqueous carrier composition is dispersed (e.g., an emulsion or microemulsion), where the composition reduces platelet aggregation at an NSAID dose below a dose typically required to illicit the same therapeutic response in the absence of the phospholipid with decreased mucosal toxicity and/or irritation.

Composition for Treating Pyretic Conditions

The present invention also provides a composition for antipyretic activity including a non-aqueous carrier including a therapeutically effective amount of an NSAID and a sufficient amount of a phospholipid to reduce the pathogenic effects of the NSAID or an aqueous solution into which the non-aqueous carrier composition is dispersed (e.g., an emulsion or microemulsion), where the composition has anti-pyretic activity at an NSAID dose below a dose typically required to illicit the same therapeutic response in the absence of the phospholipid with decreased mucosal toxicity and/or irritation.

Composition for Treating Ulcerated Tissues

The present invention provides a composition for treating ulcerated tissues including an aqueous emulsion or microemulsion comprising a phospholipid, a bio-compatible oil and zero to a therapeutically effective amount of an NSAID or a non-aqueous including comprising a phospholipid, a bio-compatible oil and zero to a therapeutically effective amount of an NSAID, where the phospholipid is present in a sufficient amount to reduce tissue ulceration and the NSAID, when present, reduces inflammation of the ulcerated regions of the tissue.

Compositions for Treating Oral Ulcerations

The present invention also provides a mouth wash including an aqueous emulsion or microemulsion comprising a phospholipid, a bio-compatible oil and zero to a therapeutically effective amount of an NSAID, where the phospholipid is present in a sufficient amount to reduce mouth ulceration and the NSAID, when present, reduces inflammation of the ulcerated regions of the mouth and the amount of phospholipid is sufficient not only to reduce mouth ulceration, but is also sufficient to reduce or present NSAID induced tissue damage.

Compositions for Treating Oral, Esophagus and GI Tract Ulcerations

The present invention also provides a drinkable medication including an aqueous emulsion or microemulsion comprising a phospholipid, a bio-compatible oil and zero to a therapeutically effective amount of an NSAID, where the phospholipid is present in a sufficient amount to reduce mouth, esophagus, and/or GI tract ulceration and the NSAID, when present, reduces inflammation of the ulcerated regions of the mouth, esophagus and/or GI tract, and the amount of phospholipid is sufficient not only to reduce mouth, esophagus and/or GI tract ulceration, but is also sufficient to reduce when present NSAID induced tissue damage.

Composition for Treating Eye Inflammation

The present invention also provides eye drops including an aqueous emulsion or microemulsion comprising a phospholipid, a bio-compatible oil and zero to a therapeutically effective amount of an NSAID in an aqueous solution, where the phospholipid is present in a sufficient amount to reduce eye inflammation and/or ulceration or irritation and the NSAID, when present, reduces inflammation of the scleral, uveal, lens or chorio-retinal regions of the eye, and the amount of phospholipid is sufficient not only to reduce eye inflammation, but is also sufficient to reduce or present NSAID induced tissue damage.

Methods for Treating Ulcerated Tissues

The present invention also provides methods for treating inflammation and/or ulceration disorders of the mouth, esophagus, GI tract, and/or eye via the administration of an emulsion or microemulsion of this invention.

Composition for Treating Central and/or Peripheral Nerve System Traumas

The present invention also provides a composition for orally or internally treating spinal cord, stroke and/or traumatic brain injuries, where the composition includes a non-aqueous carrier including a phospholipid and a therapeutically effective amount of an NSAID or a non-aqueous including comprising a phospholipid, a bio-compatible oil and zero to a therapeutically effective amount of an NSAID, where the phospholipid increases transport of the NSAID across the blood-brain barrier or into the central nervous system (CNS) or peripheral nervous system (PNS) allowing more NSAID to get to the trauma site and reduce inflammation, where NSAID reduces inflammation, platelet aggregation, pain (nociceptive) sensation, cell death and/or apoptosis due to inflammation.

Methods for Treating Central and/or Peripheral Nerve System Traumas

The present invention also provides methods for treating spinal cord, stroke and/or traumatic brain injuries by orally administering and/or directly administering via injection a composition of this invention, where the direct administration can be either into a vein (i.v. administration), an artery (i.a. administration) or directly into the trauma site (direct administration), where the phospholipid increases transport of the NSAID across the blood-brain barrier allowing more NSAID to get to the trauma site and reduce inflammation for i.v. and i.a. administration and the phospholipid reduces the pathogenic effects of the NSAID in all administration formats.

The present invention also provides a medication for ameliorating symptoms of spinal chord injury (e.g., chronic pain syndrome), stroke and/or traumatic brain injury, where the medication is an aqueous emulsion or microemulsion including a relatively high concentration of an NSAID in an oil based carrier including a phospholipid, where the NSAID and the phospholipid form an association complex in the medication, where the composition include a sufficient concentration of the NSAID to reduce swelling of the traumatized tissue and a sufficient concentration of the phospholipid to reduce the pathogenic effects of the NSAID on the traumatized tissue.

Composition for Treating Alzheimer's Disease

The present invention also provides a composition for preventing, treating or ameliorating the symptoms associated with Alzheimer's disease including a bio-compatible oil, a phospholipid and a therapeutically effective amount of an NSAID, where the NSAID and the phospholipid act to prevent the onset of the symptoms of Alzheimer's disease or ameliorate the symptoms of Alzheimer's disease.

Methods for Treating Alzheimer's Disease

The present invention also provides a method for preventing, treating or ameliorating the symptoms associated with Alzheimer's disease including the step of orally or internally administering a composition of this invention orally and/or internally according to a treatment protocol.

DESCRIPTION OF THE DRAWINGS

The invention can be better understood with reference to the following detailed description together with the appended illustrative drawings in which like elements are numbered the same.

DEFINITIONS OF TERMS

Figure 1:
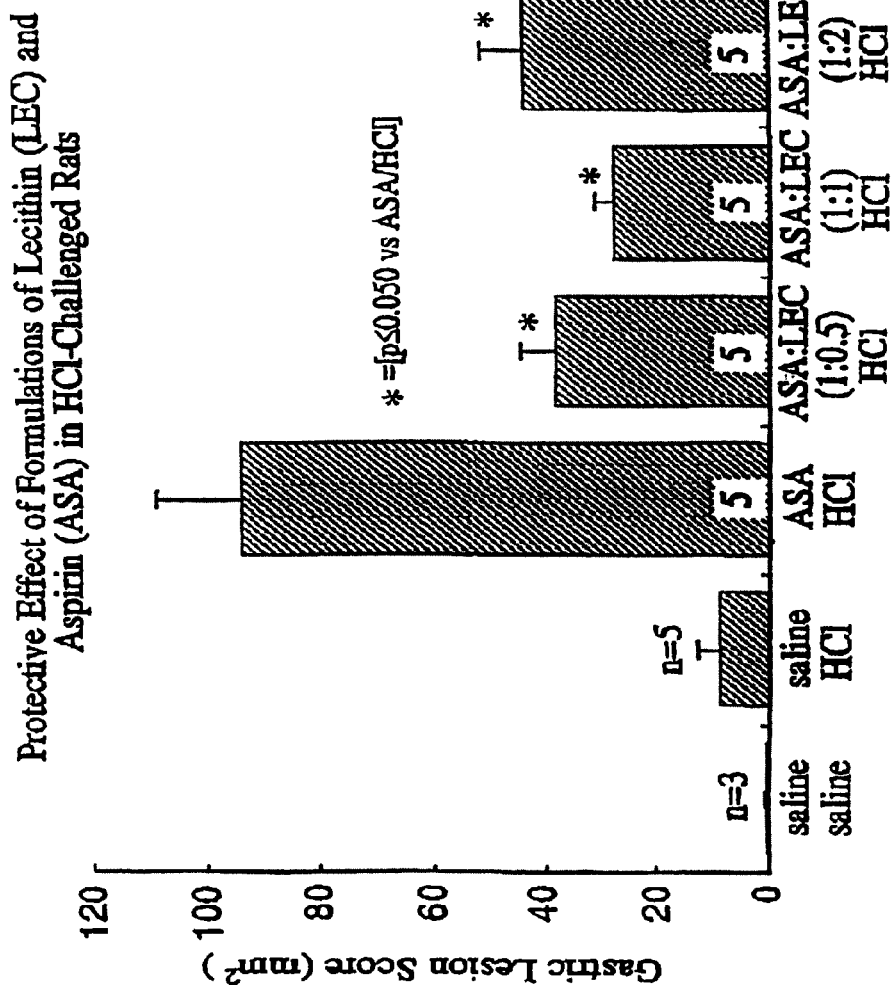
FIG. 1 demonstrates that in contrast to the high number of gastric lesions observed in rats administered aspirin (ASA) alone, rats treated with all three aspirin:lecithin (LEC, using the lecithin oil, Phosal 35 SB) formulations having a ASA: LEC weight ratio of about 1:0.5, 1:1 and about 1:2 had significantly fewer gastric lesions.

The following terms will have the meanings set forth below, which may or may not correspond to their generally accepted meaning:

The term "NSAID" means any variety of drugs generally classified as nonsteroidal anti-inflammatory drugs, including, without limitation, ibuprofen, piroxicam, salicylate, aspirin, naproxen, indomethacin, diclofenac, acetaminophen, COX2 inhibitors or any mixture thereof.

The term "essentially free" means compositions that include a given ingredient in an amount that is biologically inert and/or not an active, preferably, the component is present in an amount less than about 0.10 wt. % of a given ingredient, and particularly in an amount less than about 0.01 wt. % being preferred.

The term "relatively high concentration" means that the weight ratio of NSAID to carrier is from about 10:1 to about 1:10. Preferably, the weight ratio of NSAID to carrier is from about 5:1 to about 1:5, particular, from about 2:1 to 1:2, and especially from about 2:1 to 1:1.

The term zwitterionic phospholipid embraces a wide range of phospholipids, including but not limited to phosphatidylcholine, phosphatidylserine, phosphalidylethanolamine, sphingomyelin and other ceramides, as well as various other zwitterionic phospholipids.

The term "bio-compatible oil" means any oil that has been approved for human consumption by the FDA or animal consumption.

The term "internal administration" or "internally administered" means administration via any technique that present a composition directly into the blood stream, a tissue site, an organ or the like without first passing through the digestive tract.

The term "oral administration" or "oral administered" means administration via mouth.

The term "topical administration" or "topically administered" means administration onto a surface such as the skin, a mucosal gel layer, the eye, a tissue and/or organ exposed during a surgical procedure, or any other exposed bodily tissue.

The term "association complex" means a non-covalent chemical and/or physical interaction between an NSAID and a phospholipid such as the interaction between an NSAID and a zwitterionic phospholipid.

The term "zwitterionic" means that a molecule includes both a positively charged and a negatively charged functional group at biological pHs.

The term "anionic phospholipid" means a phospholipid which has an overall negative charge at biological pHs.

The term "neutral lipid" means a non-charged lipid.

The term "emulsion" means the suspension of one immiscible phase in another immiscible phase in the form of small droplets of the first phase in the second phase. As used herein, the term emulsion includes suspension that separate quickly or not at all, and, therefore, includes stable and non-stable emulsions.

The term "stable emulsion" means a oil in water mixture that does not separate for at least one day after preparation, preferably does not separate for at least one week, particularly does not separate after at least one month and especially remains in an emulsion indefinitely.

The term "stable microemulsion" means a oil in water mixture that does not separate for at least one day after preparation, preferably does not separate for at least one week, particularly does not separate after at least one month and especially remains in an emulsion indefinitely.

The term "relatively hydrophobic barriers" means any external, internal, cellular or sub-cellular barrier which has hydrophobic properties, which generally resists or reduces transport of hydrophilic reagents across the barrier. Such barriers include, without limitation, a mucosal gel layer, a plasma lemma (cellular membrane), the blood-brain barrier, or any other barrier of an animal including a human, which more easily transports hydrophobic materials therethrough than hydrophilic materials.

DETAILED DESCRIPTION OF THE INVENTION

The inventor has found that unique pharmaceutical formulations containing a non-aqueous, fluid bio-compatible carrier including a phospholipid and optionally a NSAID can be prepared to improve the repair of mucosal tissue ulceration and/or decrease pathogenic effects of NSAID administration. When the NSAID is present, a weight ratio of NSAID to carrier is generally from about 10:1 to about 1:10, which results in highly concentrated mixture of the NSAID in the carrier that have unexpected properties of low GI toxicity and enhanced therapeutic activity for the NSAID. Preferably, the weight ratio of NSAID to carrier is from about 5:1 to about 1:5, particular, from about 2:1 to 1:2, and especially from about 2:1 to 1:1.

For composition including an NSAID, this invention has been reduced to practice in rodent models of NSAID-induced ulcer disease, and acute inflammation of the hindpaw. The formulations can be in the form of a solution, a paste, a semi-solid, a dispersion, a suspension, a colloidal suspension or a mixture thereof.

For composition that do not include an NSAID, the phospholipid itself may impart a therapeutically beneficial effect in preventing and/or reducing ulcerations in tissues, especially tissue ulceration caused by radiotherapy and/or chemotherapy.

The non-aqueous, fluid bio-compatible carrier comprises a bio-compatible oil or mixture of bio-compatible oils or oil like substances. The bio-compatible oil or oil mixture can either naturally include a phospholipid or has had a phospholipid added thereto. The amount of phospholipid present naturally or via addition to the carrier is sufficient of prevent, reduce or treat ulceration of tissues or, when the formulation includes an NSAID, is sufficient to reduce the pathogenic effects of the NSAID, such as GI ulceration, bleeding, liver damage, kidney damage, and/or cardiovascular disease and/or side-effects such as; high blood pressure, atherosclerosis, thrombosis, angina pectoralis, strokes and myocardial infarction.

The inventor has also found that an aqueous emulsion or microemulsion of the above compositions can be formed to treat mouth, esophagus and GI ulceration resulting form or caused by radiotherapy and/or chemotherapy of various forms of cancer. The emulsion or microemulsion can either be administered after, during, prior to or can be administered in a mixed protocol including administration prior to, during and/or after radiotherapy and/or chemotherapy.

In previous publications and patents both by the inventor and others, compositions including a phospholipid and an NSAID were formed either by initially dissolving the components in an organic solvent, such as methanol, ethanol or chloroform, and removing the solvent by distillation or evaporation; or the NSAID was dissolved in an aqueous solution to which the phospholipid was added, followed by lyophilization. These processes allow the two components to chemically interact to form a complex. These processes most often used a phosphatidylcholine (PC) as the phospholipid either synthetically prepared such as dipalmitoylphosphatidylcholine (DPPC) or as a purified or semipurified compound.

The present invention relates broadly to a pharmaceutical formulation or composition including a non-aqueous, fluid carrier including a phospholipid and optionally an NSAID, where the phospholipid is in an amount sufficient to prevent, reduce or treat tissue ulceration and/or inflammation, and when an NSAID is present, and the phospholipid is present in the amount capable of reducing the pathogenic effects of the NSAID. The formulations are generally viscous solutions, pastes, semi-solids, dispersions, suspensions, colloidal suspension or mixtures thereof and are capable of being orally administered, directly administered, internally administered or topically administered.

The present invention relates broadly to a pharmaceutical formulation or composition including a non-aqueous, fluid carrier including a phospholipid and an NSAID, where the phospholipid is in an amount sufficient to prevent, reduce or treat tissue ulceration, and to reduce the GI toxicity of the NSAID. The use of a non-aqueous, fluid allows the formation of compositions having high concentrations of the NSAID to reduce a volume of an effective therapeutic amount of the NSAID. The formulations are generally viscous solutions, pastes, semi-solids, dispersions, suspensions, colloidal suspension or mixtures thereof and are capable of being orally administered, internally administered or topically administered.

The present invention also relate broadly to a method of preparing the pharmaceutical formulations including the step of combining a solid NSAID with a non-aqueous carrier, where the carrier includes a phospholipid-containing bio-compatible oil or a bio-compatible oil and a phospholipid, or mixtures thereof, to form a highly concentrated NSAID composition with reduced NSAID pathogenic effects.

The present invention also broadly relates to a method for treating inflammation, pain or other NSAID treatable pathologies by administering an effective amount of a pharmaceutical formulation including a non-aqueous, fluid carrier including an NSAID and a phospholipid, where the phospholipid is present in an amount sufficient to reduce NSAID pathology and the NSAID is present in a therapeutically effective amount, where the phospholipid-NSAID combination allows the amount of NSAID administered per dose to be less than an equivalent amount of NSAID in the absence of the phospholipid to illicit the same therapeutic effect.

The present invention also broadly relates to a method for preventing, reducing and/or treating ulcerated tissue and/or reducing inflammation, pain or other NSAID treatable pathologies associated with tissue inflammation and/or ulceration by administering an effective amount of a pharmaceutical formulation including a phospholipid and optionally an NSAID in a non-aqueous carrier, where the carrier is a bio-compatible oils or mixture thereof.

In particular, the inventor has found that unique pharmaceutical formulations containing a bio-compatible oil including a phospholipid such as non-purified lecithin oils which naturally includes a phospholipid and where the resulting formulation represent a solution, a paste, a semi-solid, a dispersion, a suspension, colloidal suspension or mixtures thereof or composition with unexpected properties of low GI toxicity and enhanced therapeutic activity.

Figure 2:
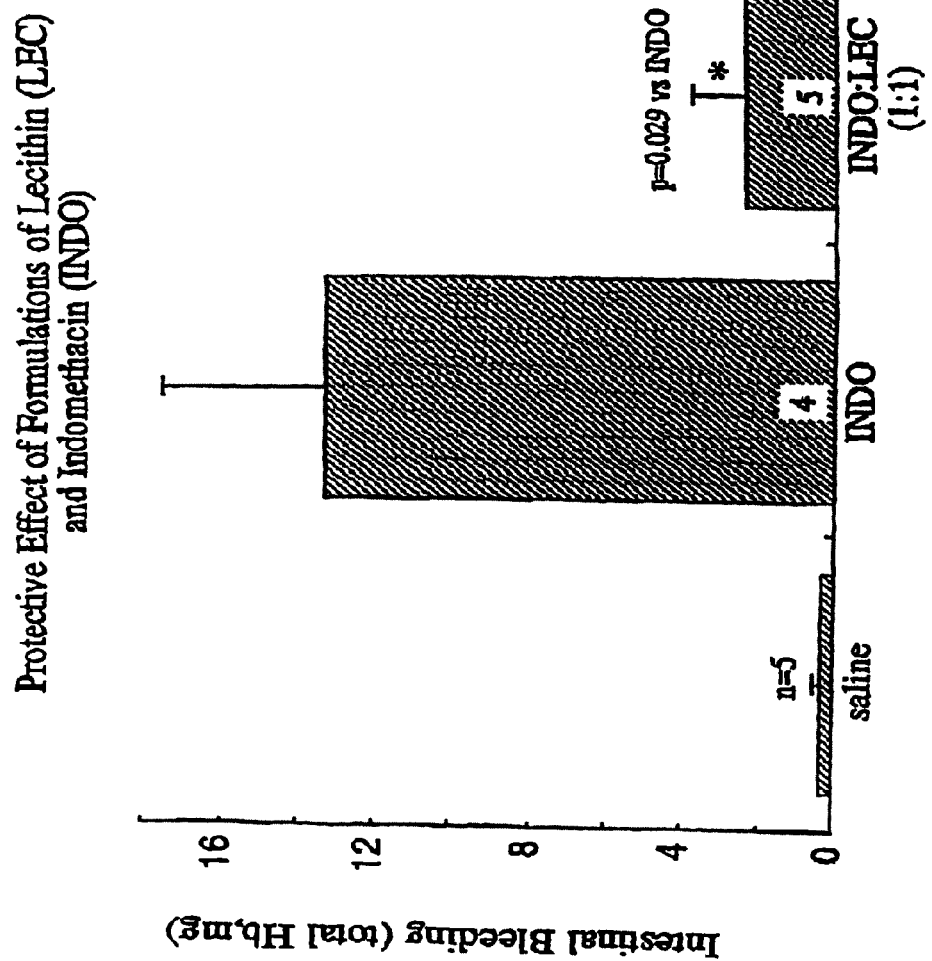
FIG. 2 demonstrates that indomethacin, at a dose of 10 mg/kg, induces a severe increase in GI bleeding that is markedly and significantly reduced in rats that were intragastrically administered an equivalent dose of indomethacin in combination with Phosal 35 SB, at a NSAID:lecithin weight ration of 1:1.
Figure 3:
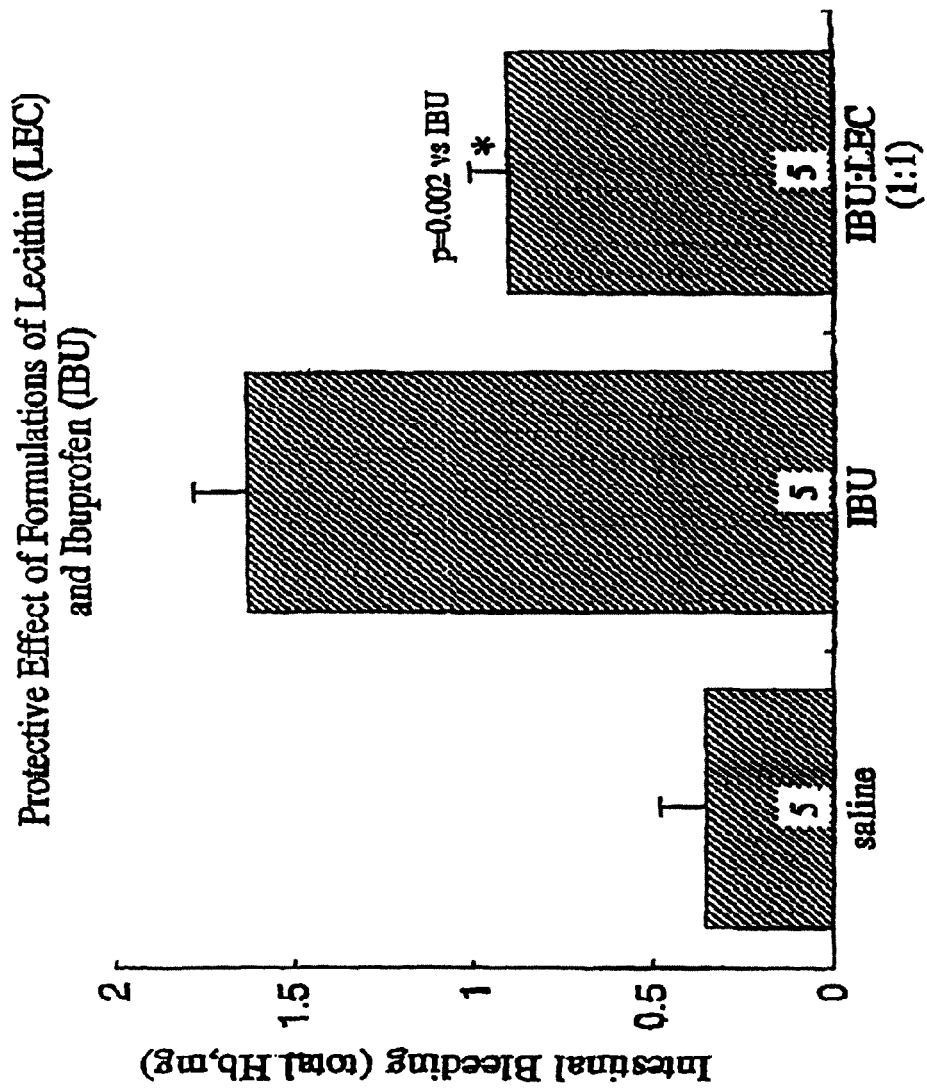
FIG. 3 demonstrates that ibuprofen (which is considered one of the least toxic of the conventional NSAIDs in rats), at a dose of 100 mg/kg induces a modest increase in GI bleeding that is significantly reduced in rats that were intragastrically administered an equivalent dose of ibuprofen in combination with Phosal 35 SB, at a NSAID:lecithin weight ratio of 1:1.
Figure 4:
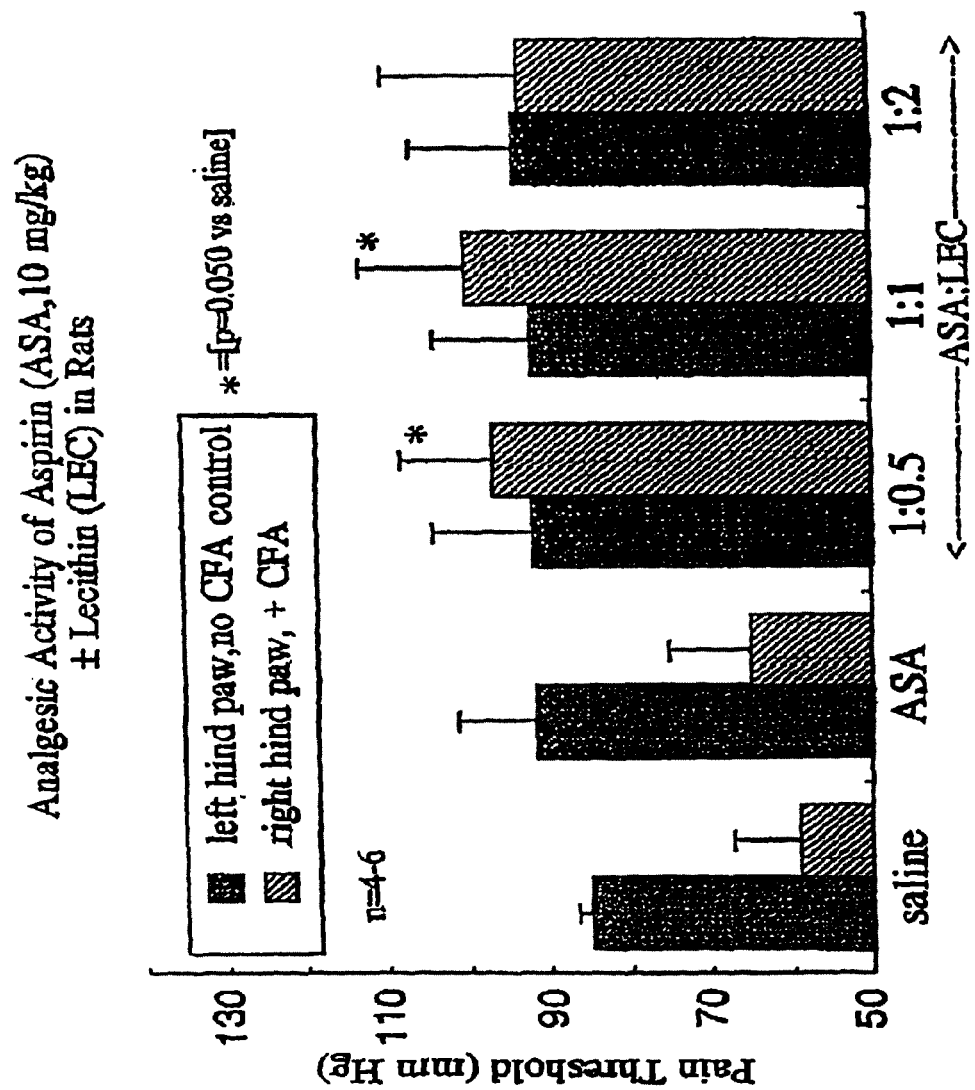
FIG. 4 demonstrates that aspirin, at a dose of 10 mg/kg, had a modest ability to increase the pain threshold of the rats' affected paw, whereas the analgesic activity of an equivalent dose of aspirin, when administered in combination with the lecithin oil, at all weight ratios tested, was significantly enhanced.
Figure 15:
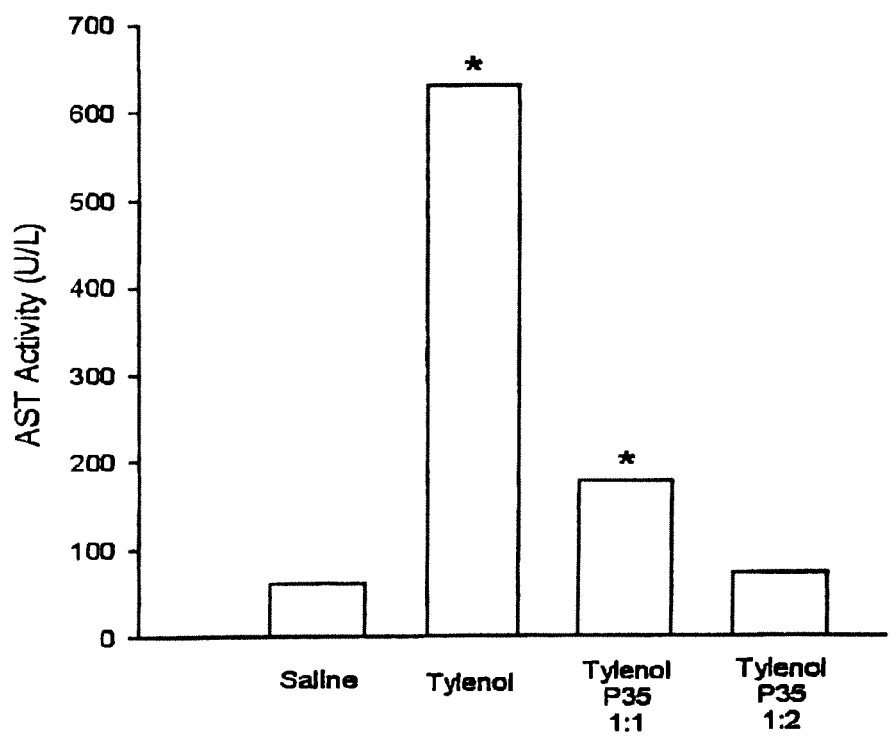
FIG. 15 graphically depicts data relating to liver injury in rats, as indicated by elevations in the plasma levels of the enzyme aspartate transaminase (AST), 24 hours after fasted rats are orally administered acetaminophen (800 mg/kg) alone or in combination with P35SB at wt. ratios of 1:1 and 1:2.

The compositions are easily prepared by combining a bio-compatible oil and a phospholipid and optionally an NSAID, where the NSAID is added as a powder directly into a crude or semi-crude lecithin oil to form a paste, semi-solid, dispersion or colloidal suspension or similar composition that can be added to soft or hard gelatin capsules or vegicaps available from VitaHerb Nutraceuticals of Placentia, Calif. for oral administration, injected for internal administration or applied to the skin for topical administration. An unexpected observation was that this simple formulations, similar to PC-NSAID products that are made by the conventional methods described above, have markedly low gastrointestinal (GI) toxicity in rodent models of NSAID-induced ulcer disease as shown in FIGS. 1, 2 & 15, and also have enhanced therapeutic activity to treat inflammation/pain in an acute model of paw inflammation as shown in FIGS. 3 & 4, and chronic models of spinal chord injuries as shown in FIGS. 7 & 8.

Generally, the weight ratio of NSAID to a phospholipid-containing oil ranges from about 10:1 to about 1:10, preferably, from about 4:1 to about 1:4, particularly, from about 2:1 and about 1:2, and especially, from about 2:1 to about 1:1. For oils useful in the practice of this invention that naturally contain a phospholipid, the oils generally include from about 10 to about 15 wt. % of a phospholipid, preferably, from about 10 wt. % to about 20 wt. % of a phospholipid, and particularly, from about 10 wt. % to about 40 wt. % of a phospholipid. However, greater and lesser amounts of a phospholipid can be used as well. However, at wt. % much below about 10 wt. %, an effective therapeutic amount or sufficient amount to associate with any added NSAID becomes a concern, while at wt. % higher than about 40 wt. %, a purified phospholipid may have to be added to bio-compatible oils that naturally include a phospholipid such as lecithin oil. For bio-compatible oils that contain either low amount of a phospholipid (less than about 10 wt. %), a phospholipid is added to the oil. Such oil-phospholipid combination can be prepared with phospholipid concentrations as high as about 90 wt. %. However, preferred combination include phospholipid amounts of between about 10 wt. % and about 90 wt. %, particularly between about 20 wt. % and about 80 wt. %, more particularly, between about 20 wt. % and about 60 wt. % and especially, between about 20 wt. % and about 40 wt. %.

Generally, the dose of NSAID containing compositions of this invention for general use ranges from 5 mg per dose to 500 mg per dose. Of course, smaller and higher dose formulations can be prepared; however, this does range encompasses the ranges typically encountered for NSAIDs commercially available. Preferably, the NSAID dose range is from about 10 mg to about 325 mg per dose, particularly, from about 25 mg to about 200 mg per dose and especially from about 50 mg to about 100 mg per dose. It should be recognized that each NSAID has a different dose range per tablet or the like, and these ranges are meant to encompasses all ranges that a patient would generally encounter when taking formulations containing an NSAID as that term is used herein. It should also be recognized that the composition of this invention do not just include an NSAID, but include an NSAID in a non-aqueous, fluid carrier including a phospholipid, where the amount of phospholipid is sufficient, when an NSAID is present, to enhance the therapeutic efficacy of the NSAID, while reducing NSAID pathogenic effects. These NSAID pathogenic effects are, of course, NSAID specific, but include, without limitation, GI damage such as ulceration, bleeding or the like (most, if not all NSAIDs), liver damage (e.g., acetaminophen), kidney damage (e.g., ibuprofen, acetaminophen, COX-2 inhibitors), heart damage (e.g., COX-2 inhibitors), etc. Because NSAID-phospholipid associated complexes, the mg dose of NSAID needed to illicit a given therapeutic effect or response (fever reduction, reduction in inflammation, reduction in platelet aggregation, etc.) is reduced. The reduction can be range from a 1 fold reduction in mg dose to a 15 fold reduction in mg dose. Preferably, the range is from about a 1 fold reduction to about a 10 fold reduction in mg NSAID dose. The increased bio-activity afforded by a composition including phospholipid-NSAID combination does not result in an equivalent increase in toxicity of the NSAID, but surprisingly results in a decreased toxicity of the NSAID as evidenced by the data present herein.

For more severe condition such as arthritis, Alzheimer's disease, CNS and PNS trauma, or other more severe condition treatable with NSAIDs and/or phospholipids, the NSAID daily dose requirements are generally much higher. Typically, the daily dose ranges from about 100 mg to about 5000 mg per day, preferably, from about 500 mg to about 3000 mg per day, particularly, from about 750 mg to about 3000 mg per day and especially from about 1000 mg to about 3000 mg per day. Again, the enhanced efficacy of phospholipid-NSAID combinations allow the dose to illicit a greater therapeutic effect, without concurrent increase in pathogenic or toxicity of the NSAID. Of course, this enhancement in bio-activity of the NSAIDs allows lower doses of the NSAIDs to be administered.

As a general rule of thumb, when administering an NSAID in a formulation of this invention, where the NSAID is dissolved, dispersed, suspended or otherwise mixed into a non-aqueous carrier, a bio-compatible oil, including a sufficient amount of a phospholipid to enhance NSAID activity, while reducing NSAID toxicity, the dosage requirements can from as low as 5% of the recommended dose needed to treat a specific condition to 100% of that dose depending on the patient, the condition and other factors. Preferably, the dosage is from about 10% to about 90% of the recommended dose needed to treat a specific condition and particularly from about 10% to about 50% of the recommended dose needed to treat a specific condition. The recommended dosage requirements for a given NSAID for a given condition can be found in such publication as the Physicians Desk Reference (PDR), AMA publication, FDA publication or the like, and are well established criteria.

The compositions of this invention can also include: (1) a pharmaceutically acceptable amount of antioxidant selected from the group consisting of Vitamin A, Vitamin C, Vitamin E or other antioxidants approved for human and animal consumption by the FDA and mixtures or combinations thereof; (2) a pharmaceutically acceptable amount of a polyvalent cation selected from the group consisting of copper, zinc, gold, aluminum and calcium and mixtures or combinations thereof; (3) a pharmaceutically acceptable amount of an agent to promote fluidity, spreadability or permeability selected from the group consisting of dimethylsulfoxide/DMSO, propylene glycol/PPG, and medium chain triglyceride/MCT and mixtures or combination thereof; (4) a pharmaceutically acceptable amount of a food coloration or non-toxic dye; (5) a pharmaceutically acceptable amount of a flavor enhancer; (6) an excipient; and/or (7) an adjuvant.

General Compositions

The present invention relates to a composition including a relatively high concentration of a non-steroidal anti-inflammatory drugs (NSAID) in a non-aqueous, fluid carrier. Preferably, the carrier comprises a bio-compatible oil and a phospholipid or a phospholipid rich bio-compatible oil. The carrier either naturally and/or via addition includes a sufficient amount phospholipid to reduce pathogenic affects of the NSAID, to increase a bioavailability of the NSAID and to increase NSAID availability across relatively hydrophobic barriers in an animal's body including a human's body. Preferably, the resulting composition includes a relatively high concentration of a phospholipid-NSAID association complex. Particularly, the resulting composition includes a relatively high concentration of a phosphatidylcholine-NSAID associated complex.

The present invention relates to a composition including a relatively high concentration of an NSAID in a non-aqueous, fluid carrier comprising a phospholipid and a bio-compatible oil, where the phospholipid is present in an amount sufficient to reduce pathogenic affects of the NSAID, to increase the bioavailability of the NSAID and to increase NSAID availability across relatively hydrophobic barriers in an animal's body including a human body, where the composition dose is sufficient to result in the delivery of a therapeutical effective amount of the NSAID and/or the phospholipid, where the amount of NSAID is 1-10 fold less than an amount of NSAID needed to illicit the same therapeutic effect in the absence of the phospholipid. Preferably, the resulting composition includes a relatively high concentration of a phospholipid-NSAID association complex. Particularly, the resulting composition includes a relatively high concentration of a phosphatidylcholine-NSAID associated complex.

The presence of the phospholipid in the composition of this invention also reduces general and specific pathogenic and/or toxicity of NSAIDs. Thus, the phospholipids reduce and/or prevent liver damage due to the administration of acetaminophen and/or kidney and/or heart damage due to the administration of other NSAIDs such as ibuprofen or COX2 inhibitors.

General Methods for Making the General Compositions

The present invention also relates to a method of preparing a composition comprising an NSAID in a non-aqueous, fluid carrier comprising the step of combining the NSAID with the carrier to form a solution, a paste, a semi-solid, a dispersion, a suspension, a colloidal suspension or a mixture thereof; having a relatively high concentration of the NSAID. Preferably, the carrier comprises a phospholipid-containing bio-compatible oil or a bio-compatible oil and a phospholipid. Preferably, the resulting composition includes a relatively high concentration of a phospholipid-NSAID association complex. Particularly, the resulting composition includes a relatively high concentration of a phosphatidylcholine-NSAID associated complex.

Emulsified Compositions

The present invention also relates to an aqueous emulsion of a composition including a non-aqueous carrier, where the carrier includes a bio-compatible oil, a phospholipid in an amount sufficient to produce a therapeutically beneficial effect and zero to a therapeutically effective amount of an NSAID and when the NSAID is present, the amount of phospholipid is also sufficient to reduce the pathogenic effects of the NSAID. The aqueous emulsion can also include bio-compatible emulsifying agents to maintain the composition in a state of emulsion for extended periods of time. Preferably, the carrier comprises a phospholipid-containing bio-compatible oil or a bio-compatible oil and a phospholipid. Preferably, the resulting emulsion includes the composition having a relatively high concentration of a phospholipid-NSAID association complex. Particularly, the resulting composition includes a relatively high concentration of a phosphatidylcholine-NSAID associated complex.

The present invention also relates to an aqueous microemulsion of a composition including an non-aqueous carrier, where the carrier includes a bio-compatible oil, a phospholipid in an amount sufficient to produce a therapeutically beneficial effect and zero to a therapeutically effective amount of a NSAID and when the NSAID is present, the amount of phospholipid is also sufficient to reduce the pathogenic effects of the NSAID. The aqueous emulsion can also include bio-compatible emulsifying agents to maintain the composition in a state of emulsion for extended periods of time. The aqueous microemulsion can also include bio-compatible emulsifying agents to maintain the composition in a state of microemulsion for extended periods of time. Preferably, the carrier comprises a phospholipid-containing bio-compatible oil or a bio-compatible oil and a phospholipid. Preferably, the resulting emulsion includes the composition having a relatively high concentration of a phospholipid-NSAID association complex. Particularly, the resulting composition includes a relatively high concentration of a phosphatidylcholine-NSAID associated complex.

Method for Making Emulsified Compositions

The present invention also relates to a method for preparing an aqueous emulsion of this invention including the step of adding a given amount of a desired non-aqueous composition of this invention to an aqueous solution in the absence or presence of an emulsifying agent and mixing the composition and the solution for a time sufficient to form an emulsion, where the emulsifying agent, when present, is present in an amount sufficient to form a stable emulsion.

The present invention also relates to a method for preparing an aqueous microemulsion of this invention including the step of adding a given amount of a desired non-aqueous composition of this invention to an aqueous solution in the absence or presence of an emulsifying agent, mixing the composition and solution for a time sufficient to form an emulsion, and shearing the emulsion under microemulsifying conditions to form a microemulsion, where the emulsifying agent, when present, is present in an amount sufficient to form a stable microemulsion.

The reason the emulsifying agent is optional is because the phospholipid themselves have some emulsifying properties.

Compositions for Treating Inflammation

The present invention also relates to a composition for reducing tissue inflammation including a non-aqueous carrier including a therapeutically effective amount of an NSAID and a sufficient amount of a phospholipid to reduce the pathogenic effects of the NSAID, where the composition reduces tissue inflammation at an NSAID dose below a dose typically required to illicit the same therapeutic response in the absence of the phospholipid with decreased mucosal toxicity and/or irritation.

Composition for Treating Platelet Aggregation

The present invention also relates to a composition for reducing platelet aggregation including a non-aqueous carrier including a therapeutically effective amount of an NSAID and a sufficient amount of a phospholipid to reduce the pathogenic effects of the NSAID, where the composition reduces platelet aggregation at an NSAID dose below a dose typically required to illicit the same therapeutic response in the absence of the phospholipid with decreased mucosal toxicity and/or irritation.

Composition for Treating Pyretic Conditions

The present invention also relates to a composition for anti-pyretic activity including a non-aqueous carrier including a therapeutically effective amount of an NSAID and a sufficient amount of a phospholipid to reduce the pathogenic effects of the NSAID, where the composition has anti-pyretic activity at an NSAID dose below a dose typically required to illicit the same therapeutic response in the absence of the phospholipid with decreased mucosal toxicity and/or irritation.

Composition for Treating Ulcerated and/or Inflammed Tissues

The present invention relates to a composition for treating ulcerated tissues including an aqueous emulsion or microemulsion comprising a phospholipid, a bio-compatible oil and zero to a therapeutically effective amount of an NSAID, where the phospholipid is present in a sufficient amount to reduce tissue inflammation and/or ulceration and the NSAID, when present, reduces inflammation of the affected regions of the tissue.

Compositions for Treating Oral Ulcerations and/or Inflammations

The present invention also relates to a mouth wash including an aqueous emulsion or microemulsion comprising a phospholipid, a bio-compatible oil and zero to a therapeutically effective amount of an NSAID, where the phospholipid is present in a sufficient amount to reduce mouth ulceration and/or inflammation and the NSAID, when present, reduces inflammation of the affected regions of the mouth.

Compositions for Treating Oral, Esophagus and GI Tract Ulcerations

The present invention also relates to a drinkable medication including an aqueous emulsion or microemulsion comprising a phospholipid, a bio-compatible oil and zero to a therapeutically effective amount of an NSAID, where the phospholipid is present in a sufficient amount to reduce mouth, esophagus, and/or GI tract inflammation and/or ulceration and the NSAID, when present, reduces inflammation of the affected regions of the mouth, esophagus and/or GI track.

Composition for Treating Eye Inflammation

The present invention also relates to eye drops including an aqueous emulsion or microemulsion comprising a phospholipid, a bio-compatible oil and zero to a therapeutically effective amount of an NSAID in an aqueous solution, where the phospholipid is present in a sufficient amount to reduce eye inflammation or irritation and the NSAID, when present, reduces inflammation of the eye associated with uveitis or related eye disorders.

Methods for Treating Ulcerated and/or Inflamed Tissues

The present invention also relates to methods for treating inflammatory and/or ulcerative disorders of the mouth, esophagus, GI tract, eye, and/or other inflamed and/or ulcerated tissue sites via the administration of an emulsion or microemulsion of this invention.

Composition for Treating Central and/or Peripheral Nerve System Traumas

The present invention also relates to a composition for orally or internally treating spinal cord, stroke and/or traumatic brain injuries, where the composition includes a non-aqueous carrier including a phospholipid and a therapeutically effective amount of an NSAID or an aqueous solution into which a non-aqueous carrier including a phospholipid and a therapeutically effective amount of an NSAID has been dispersed (e.g., emulsion or microemulsion), where the phospholipid increases transport of the NSAID across the blood-brain barrier allowing more NSAID to get to the trauma site and reduce inflammation, where NSAID reduces inflammation, platelet aggregation, anti-pyretic activity and cell death due to inflammation.

Methods for Treating Central and/or Peripheral Nerve System Traumas

The present invention also relates to methods for treating spinal cord, stroke and/or traumatic brain injuries by injecting a composition of this invention either into a vein (i.v. administration), an artery (La. administration) or directly into the trauma site (direct administration), where the phospholipid increases transport of the NSAID across the blood-brain barrier or other neurogenic barriers allowing more NSAID to get to the trauma site and reduce inflammation for i.v. and La. administration and the phospholipid reduces the pathogenic effects of the NSAID in all administration formats.

The present invention also relates to a medication for ameliorating symptoms of spinal chord, stroke and/or traumatic brain injury, where the medication includes a relatively high concentration of an NSAID in an oil based or water based carrier including a phospholipid, where the NSAID and the phospholipid form an association complex in the medication, where the composition include a sufficient concentration of the NSAID to reduce swelling of the traumatized tissue and a sufficient concentration of the phospholipid to reduce the pathogenic effects of the NSAID on the traumatized tissue.

Composition for Treating Alzheimer's Disease

The present invention also relates to a composition for preventing, treating or ameliorating the symptoms associated with Alzheimer's disease including a bio-compatible oil, a phospholipid and a therapeutically effective amount of an NSAID, where the NSAID and the phospholipid act to prevent the onset of the symptoms of Alzheimer's disease or ameliorate the symptoms of Alzheimer's disease.

Methods for Treating Alzheimer's Disease

The present invention also relates to a method for preventing, treating or ameliorating the symptoms associated with Alzheimer's disease including the step of orally or internally administering a composition of this invention orally and/or internally according to a treatment protocol.

Composition for Treating Incisions

The present invention also relates to a composition for treating incision to reduce resulting surgically induced local inflammation and promote healing, including a bio-compatible oil, a phospholipid and a therapeutically effective amount of an NSAID, where the NSAID and the phospholipid act to reduce inflammation and associated symptoms and promote healing.

Methods for Treating Incisions

The present invention also relates to a method for treating incision to reduce resulting surgically induced local inflammation and promote healing, including applying a composition including a bio-compatible oil, a phospholipid and a therapeutically effective amount of an NSAID to a surgical site during and after. surgery, but prior to closing, where the NSAID and the phospholipid act to reduce inflammation and associated symptoms and promote healing. Preferred treating formulation of this invention include spray applications of emulsions or microemulsions or similar formulation of the compositions of this invention.

Composition for Ameliorating Ulceration and/or Inflammation Caused by Radio- and/or Chemotherapy The present invention also relates to compositions for ameliorating tissue ulceration induced by radiotherapy and/or chemotherapy of certain cancers such as mucositis or related condition, where the composition includes a bio-compatible oil, a phospholipid and optionally a therapeutically effective amount of an NSAID, where the phospholipid is present in an amount sufficient to prevent and/or reduce ulceration or inflammation associated with mucositis and, when an NSAID is present, the phospholipid is present in an amount sufficient not only to prevent and/or reduce ulceration or inflammation, but also to ensure that the NSAID does not further exacerbate the condition. Preferably, for chemotherapy, the chemotherapeutic agent is administered with an appropriately formulated composition of this invention. Thus, if the chemotherapeutic agent is administered orally, the agent can be mixed with an appropriately formulated composition of this invention, provided no adverse interactions occur between the agent and the component of the compositions of this invention and administered to the patient. If adverse interactions between the chemotherapeutic agent and the components of the compositions of this invention occur or if the agent is administered by injection, then the composition of this invention is administered orally with the chemotherapeutic agent and for a sufficient time after to prevent or reduce the duration of the mucositis episode.

Methods of Ameliorating Ulceration and/or Inflammation Caused by Radio- and/or Chemotherapy The present invention also relates to methods for preventing and/or treating mucositis or other ulcerating condition induced by medical treatments such as radiotherapy and/or chemotherapy, where the method includes the steps of administering an effective amount of a composition of this invention including a bio-compatible oil, a phospholipid and optionally a therapeutically effective amount of an NSAID, where the phospholipid is present in an amount sufficient to prevent and/or reduce ulceration and/or inflammation associated with mucositis and, when an NSAID is present, the phospholipid is present in an amount sufficient not only to prevent and/or reduce ulceration, but also to ensure that the NSAID does not further exacerbate the condition, to the affected area of the body prior to, concurrent with and/or after radiotherapy or chemotherapy. Preferably, the composition is designed for oral administration and is given prior to and current with the radio- and/or chemotherapy to prevent and/or treat and/or reduce the duration of a mucositis episode.

For oral administration of the compositions of this invention, the compositions are preferably dispersed in an aqueous solution as small droplets in the form of an emulsion, microemulsion or the like. The small droplets can include emulsifying agents, suspending agents and other ingredients commonly found in mouth wash or the like. The composition of the present invention can be used in conjunction with any mouth wash or oral hygiene formulation including those formulation described in U.S. Pat. Nos. 5,407,663, 5,236,699, 5,130,146, 5,085,850, incorporated herein by reference. The composition of this invention can also be orally administered in the form of a paste, a lozenge, or any other format commonly used for oral administration. Of course, the composition can also be included in capsules, gel capsules or the like.

For topical administration, the compositions of the present invention can be in the form of an ointment, a paste, an oil, an emulsion, a microemulsion, or mixture or combination thereof. Moreover, the compositions can be mixed with other ingredients commonly used in ointments and in the cosmetic industry.

Emulsions

The compositions of the present invention may be prepared and formulated as emulsions. Emulsions are typically heterogenous systems of one liquid dispersed in another in the form of droplets usually exceeding 0.1 μm in diameter. (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called an water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and *acacia*. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

Microemulsions

In one embodiment of the present invention, the compositions of this invention are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (S0750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. Microemulsions have also been effective in the transdermal delivery of active components in both cosmetic and pharmaceutical applications. It is expected that the microemulsion compositions and formulations of the present invention will facilitate an increased therapeutic response from the phospholipids and/or the NSAID-phospholipid combinations in oral administration via the gastrointestinal tract, as well as improved local cellular therapeutic responses and uptake of the phospholipids and/or the NSAID-phospholipid combinations through hydrophobic barrier such as barriers within the gastrointestinal tract, CNS, PNS, vagina, mouth, esophagus, buccal cavity, nasal cavity, sinus cavities and other areas of administration.

Microemulsions of the present invention may also contain additional components and additives such as sorbitan monostearate (Grill 3), Labrasol, and penetration enhancers to improve the properties of the formulation and to enhance the absorption of the phospholipids and/or the NSAID-phospholipid combinations containing formulations of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Suitable phospholipids for use in this invention include, without limitation, dimyristoyl phosphatidylcholine, distearoyl phosphatidylcholine, dilinoleoyl-phosphatidylcholine (DLL-PC), dipalmitoyl-phosphatidylcholine (DPPC), soy phosphatidylchloine (Soy-PC or $PC_S$) and egg phosphatidycholine (Egg-PC or $PC_E$). In DPPC, a saturated phospholipid, the saturated aliphatic substitution $R_1$ and $R_2$ are $CH_3$—$(CH_2)_{14}$, $R_3$ is $CH_3$ and X is H. In DLL-PC, an unsaturated phospholipid, $R_1$ and $R_2$ are $CH_3$—$(CH_2)_4$—CH=CH—$CH_2$—CH=CH—$(CH_2)_7$, $R_3$ is $CH_3$ and X is H. In Egg PC, which is a mixture of unsaturated phospholipids, $R_1$ primarily contains a saturated aliphatic substitution (e.g., palmitic or stearic acid), and $R_2$ is primarily an unsaturated aliphatic substitution (e.g., oleic or arachidonic acid). In Soy-PC, which in addition to the saturated phospholipids (palmitic acid and stearic acid) is a mixture of unsaturated phospholipids, [oleic acid, linoleic acid and linolenic acid]. The preferred zwitterionic phospholipid include, without limitation, dipalmitoyl phosphatidylcholine, phosphatidyl choline, or a mixture thereof.

Suitable NSAIDS include, without limitation, Propionic acid drugs such as Fenoprofen calcium (Nalfon®), Flurbiprofen (Ansaid®), Suprofen. Benoxaprofen, Ibuprofen (prescription Motrin®), Ibuprofen (200 mg. over the counter Nuprin, Motrin 1B®), Ketoprofen (Orduis, Oruvall®), Naproxen (Naprosyn®), Naproxen sodium (Aleve, Anaprox, Aflaxen®), Oxaprozin (Daypro®), or the like; Acetic acid drug such as Diclofenac sodium (Voltaren®), Diclofenac potassium (Cataflam®), Etodolac (Lodine®), Indomethacin (Indocin®), Ketorolac tromethamine (Acular, Toradol® intramuscular), Ketorolac (oral Toradol®), or the like; Ketone drugs such as Nabumetone (Relafen®), Sulindac (Clinoril®), Tolmetin sodium (Tolectin®). or the like; Fenamate drugs such as Meclofenamate sodium (Meclomen®), Mefenamic acid (Ponstel®), or the like; Oxicam drugs such as Piroxicam (Dolibid®), or the like; Salicylic acid drugs such as Diflunisal (Feldene®), Aspirin, or the like; Pyrazolin acid drugs such as Oxyphenbutazone (Tandearil®), Phenylbutazone (Butazolidin®), or the like; acetaminophen (Tylenol®), or the like; COX-2 inhibitors such as Celebrex, Vioxx, or the like, or mixtures or combinations thereof Suitable bio-compatible emulsifying agent include, without limitation, any ionic or non-ionic emulsifying agent or surfactants approved for human or animal consumption or internal use. Exemplary examples include acetylated monoglycerides, aluminum salts of fatty acids, Arabinogalactan, Bakers Yeast Glycan, Calcium carbonate, Calcium salts of fatty acids, Carob bean gum (locust bean gum), Curdlan, Diacetyl tartaric acid esters of mono- and diglycerides of edible fats or oils, or edible fat-forming fatty acids, Dioctyl sodium sulfosuccinate, Disodium phosphate (X-ref Sodium phosphate, mono-, di-, & tri-), Ethoxylated mono- and diglycerides, *Eucheuma cottonii* extract, *Eucheuma spinosum* extract, Fatty acids, salts of (aluminum, calcium, magnesium, potassium, and sodium), Food starch esterified with n-octenyl succinic anhydride treated with beta-amylase, Furazolidone, Furcelleran, Furcelleran, salts of ammonium, calcium, potassium, or sodium, Ghatti gum, Gigartina extracts, Glyceryllacto esters of fatty acids, Hexitol oleate, Hydroxylated lecithin, Hydroxypropyl cellulose, Hydroxypropyl methylcellulose, Lactylated fatty acid esters of glycerol and propylene glycol, Lactylic esters of fatty acids, Lecithin, hydroxylated lecithin, Methyl ethyl cellulose, Mono- & diglycerides of edible fats or oils, or edible fat forming acids, Monoisopropyl citrate, Monosodium phosphate derivatives of mono- & diglycerides of edible fats or oils, or edible fat-forming fatty acids, Myrj 45 (polyoxyethylene 8-stearate), Ox bile extract, Pectins (including pectin modified), Polyethylene glycol (400) dioleate, Polyglycerol esters of fatty acids, Polyoxyethylene glycol (400) mono- & di-oleates, Polysorbate 60 (Polyoxyethylene (20) sorbitan monostearate), Polysorbate 65 (Polyoxyethylene (20) sorbitan tristearate), Polysorbate 80 (Polyoxyethylene (20) sorbitan monooleate), Potassium salts of fatty acids, Propylene glycol alginate (Propylene glycol ester of alginic acid), Propylene glycol mono- & di-esters of fats & fatty acids, Rapeseed oil, fully hydrogenated, superglycerinated, Sodium acid pyrophosphate, Sodium aluminum phosphate, Sodium hypophosphite, Sodium lauryl sulfate, Sodium metaphosphate, Sodium methyl sulfate, Sodium pectinate, Sodium salts of fatty acids, Sodium stearoyl lactylate, Sodium sulfo-acetate derivatives (mono- & di-glycerides), Sorbitan monooleate, Sorbitan monostearate, Succinylated monoglycerides, Succistearin (stearoyl propylene glycol hydrogen succinate), Sucrose acetate isobutyrate (SAM), Sucrose fatty acid esters, Sulfated butyl oleate, Trisodium phosphate, Xanthan gum, or the like or mixtures or combinations thereof.

Suitable neutral lipid include, without limitation, any neutral lipid such as the triglyceride. For a partial listing of representative neutral lipids, such as the triglycerides, reference is specifically made to U.S. Pat. Nos. 4,950,656 and 5,043,329. Both saturated and unsaturated triglycerides may be employed in the present compositions, and include such triglycerides as tripalmitin (saturated), triolein and trilinolein (unsaturated). However, these particular triglycerides are listed here for convenience only, and are merely representative of a variety of useful triglycerides, and is further not intended to be inclusive.

Non-limiting examples of suitable biocompatible, biodegradable polymers, include polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or higher poly-monomer polymers thereof or combinations or mixtures thereof. The preferred biodegradable polymers are all degraded by hydrolysis.

Typically, the polymers will either be surface erodible polymers such as polyanhydrides or bulk erodible polymers such as polyorthoesters. Poly(l-lactic acid) (PILA), poly(dl-lactic acid) (PLA), poly(glycolic acid) (PGA), polycaprolactones, copolymers, terpolymer, higher poly-monomer polymers thereof; or combinations or mixtures thereof are preferred biocompatible, biodegradable polymers. The preferred biodegradable copolymers are lactic acid and glycolic acid copolymers sometimes referred to as poly(dl-lactic-co-glycolic acid) (PLG). The co-monomer (lactide:glycolide) ratios of the poly(DL-lactic-co-glycolic acid) are preferably between about 100:0 to about 50:50 lactic acid to glycolic acid. Most preferably, the co-monomer ratios are between about 85:15 and about 50:50 lactic acid to glycolic acid. Blends of PLA with PLG, preferably about 85:15 to about 50:50 PLG to PLA, are also used to prepare polymer materials.

PLA, PILA, PGA, PLG and combinations or mixtures or blends thereof are among the synthetic polymers approved for human clinical use. They are presently utilized as surgical suture materials and in controlled release devices, as well as in other medical and pharmaceutical applications. They are biocompatible and their degradation products are low molecular weight compounds, such as lactic acid and glycolic acid, which enter into normal metabolic pathways. Furthermore, copolymers of poly(lactic-co-glycolic acid) offer the advantage of a large spectrum of degradation rates from a few days to years by simply varying the copolymer ratio of lactic acid to glycolic acid.

To enhance bio-degradation of the polymers used in biological application, the compositions of the present invention can also include the addition of enzymes that can facilitate the biodegradation of the polymers used in the composition. Preferred enzymes or similar reagents are proteases or hydrolases with ester-hydrolyzing capabilities. Such enzymes include, without limitation, proteinase K, bromelaine, pronase E, cellulase, dextranase, elastase, plasmin streptokinase, trypsin, chymotrypsin, papain, chymopapain, collagenase, subtilisn, chlostridopeptidase A, ficin, carboxypeptidase A, pectinase, pectinesterase, an oxidoreductase, an oxidase or the like. The inclusion of an appropriate amount of such a degradation enhancing agent can be used to regulate implant duration.

Suitable chemo and/or radiotherapeutic agents (trade names) include, without limitation, platinum complexed, gold (III) complexed, palladium complexes, alitretinoin (Panretin), allopurinol (Zyloprim), altretamine (Hexalen), amifostine (Ethyol), amifostine (Ethyol), amifostine (Ethyol), anastrozole (Arimidex), anastrozole (Arimidex), arsenic trioxide (Trisenox), bexarotene (Targretin), bexarotene (Targretin), bleomycin (Blenoxane), busulfan intravenous (Busulfex), busulfan oral (Myleran), capecitabine (Xeloda), capecitabine (Xeloda), capecitabine (Xeloda), carboplatin (Paraplatin), carboplatin (Paraplatin), carmustine with Polifeprosan 20 Implant (Gliadel Wafer), celecoxib (Celebrex), chlorambucil (Leukeran), cisplatin (Platinol), cisplatin (Platinol), cisplatin (Platinol), cladribine (Leustatin(2-CdA), cyclophosphamide (Cytoxan), cytarabine liposomal (DepoCyt), daunorubicin liposomal (DanuoXome), daunorubicin daunomycin (Daunorubicin), daunorubicin (daunomycin (Cerubidine), dexrazoxane (Zinecard), docetaxel (Taxotere), docetaxel (Taxotere), docetaxel (Taxotere), docetaxel (Taxotere), doxorubicin (Adriamycin PFS Injection), doxorubicin liposomal (Doxil), doxorubicin liposomal (Doxil), Elliott's B Solution (Elliott's B Solution), epirubicin (Ellence), estramustine (Emcyt), etoposide phosphate (Etopophos), etoposide phosphate (Etopophos), etoposide phosphate (Etopophos), etoposide (VP-16 (Vepesid), etoposide (VP-16 (Vepesid), exemestane (Aromasin), fludarabine (Fludara), fluorouracil (5-FU (Adrucil), gemcitabine (Gemzar), gemcitabine (Gemzar), gemtuzumab-ozogamicin (Mylotarg), goserelin acetate (Zoladex Implant), hydroxyurea (Hydrea Capsules), idarubicin (Idamycin), idarubicin (Idamycin), ifosfamide (IFEX), imatinib mesylate (Gleevec), irinotecan (Camptosar), Irinotecan (Camptosar), irinotecan (Camptosar), letrozole (Femara), letrozole (Femara), leucovorin (Leucovorin), levamisole (Ergamisol), melphalan L-PAM (Alkeran), mesna (Mesnex), methotrexate (Methotrexate), methoxsalen (Uvadex), mitoxantrone (Novantrone), mitoxantrone (Novantrone), paclitaxel (Paxene), paclitaxel (Taxol), paclitaxel (Taxol), paclitaxel (Taxol), paclitaxel (Taxol), paclitaxel (Taxol), paclitaxel (Taxol), paclitaxel (Taxol), paclitaxel (Taxol), pamidronate (Aredia), Pegademase (Adagen (Pegademase Bovine)), pentostatin (Nipent), pentostatin (Nipent), porfimer sodium (Photofrin), porfimer sodium (Photofrin), porfimer sodium (Photofrin), streptozocin (Zanosar), talc (Sclerosol), tamoxifen (Nolvadex), tamoxifen (Nolvadex), tamoxifen (Nolvadex), tamoxifen (Nolvadex), tamoxifen (Nolvadex), tamoxifen (Nolvadex), tamoxifen (Nolvadex), tamoxifen (Nolvadex), temozolamide (Temodar), teniposide VM-26 (Vumon), topotecan (Hycamtin), topotecan (Hycamtin), toremifene (Fareston), tretinoin ATRA (Vesanoid), valrubicin (Valstar), vinorelbine (Navelbine), or mixtures or combinations thereof. Of course, radiotherapy can also include traditional radiation treatments.

Although the present invention preferably relates to the use of unpurified lecithin oils, the present invention can use any bio-compatible oil which contains phospholipids including, without limitation, any human consumable oil containing a phospholipid.

Suitable bio-compatible oils include, without limitation, any oil approved for human or animal consumption by the FDA including natural oils such as plant or animal oils or their derivatives or synthetic oils and especially natural oil that are rich in phospholipids such as lecithin oils from soy beans. Exemplary examples of such oils include, essential oils, vegetable oils an hydrogenated vegetable oils, animal oils such as peanut oil, canola oil, avocado oil, safflower oil, olive oil, corn oil, soy bean oil, sesame oil, vitamin A, vitamin D, vitamin E, fish oils, or the like.

The formulation or compositions of this invention can also include other chemicals, such as anti-oxidants (e.g., Vitamin A, C, D, E, etc.), trace metals and/or polyvalent cations (aluminum, gold, copper, zinc, calcium, etc.), surface-active agents and/or solvents (e.g., propylene glycol/PPG, dimethy sulfoxide/DMSO, medium chain triglycerides/MCT, etc.), non-toxic dyes and flavor enhancers may be added to the formulation as they are being prepared to improve stability, fluidity/spreadability, permeability, effectiveness and consumer acceptance.

The formulations of the present invention which include a phospholipid preferably a PC and an NSAID can be used to fill soft gelatin capsules or hard gelatine or vegicaps for oral administration or used as is, as a solution, a paste, a semisolid, a dispersion, a suspension, a colloidal suspension or mixture thereof to be applied topically to inflamed, ulcerated and/or irritated tissue or skin.

One preferred embodiment of this formulation is a lecithin oil based PC-NSAID composition, which has been tested for GI toxicity. The three formulations that were tested include lecithin oils combined with aspirin, indomethacin and ibuprofen. In this study, aspirin was combined with Phosal® 35 SB, a lecithin oil, marketed by Phospholipid GmbH (Cologne, Germany), that is constituted of soy lecithin-derived components in sunflower oil. More particularly, Phosal® 35 SB lecithin oil contains about 33-40 wt. % phosphatidylcholine (PC, not including lyso-phosphatidylcholine), about 26-31 wt. % triglycerides, about 8-13 wt. % free fatty acids, and about 5-9 wt. % glycolipids. The aspirin/lecithin oil (Phosal® 35 SB) composition was intragastrically administered to fasted rats at an aspirin dose of 18 mg/kg, where the NSAID:lecithin oil weight ratio was systematically varied from 1:0.5, to 1:1, to 1:2. In addition, other groups of rats received an equivalent dose of aspirin in the absence of the lecithin oil, or an equivalent volume of saline. Forty five minutes later all animals were intragastrically challenged with 1 ml of 0.6 N HCl, and 15 min later, the animals were euthanized and their stomachs opened and the gastric lesions scored by an established method.[50-52]

As shown in FIG. 1, the data demonstrated that in contrast to the high number of gastric lesions observed in rats administered aspirin alone, rats treated with all three aspirin: lecithin formulations had significantly fewer gastric lesions.

In order to evaluate the gastric toxicity of the non-aspirin NSAIDs, indomethacin and ibuprofen, another ulcer model was employed—GI bleeding was the endpoint, that as previously described.[52] In this model, the NSAIDs were intragastrically administered to fasted rats either alone or in combination with the lecithin oil Phosal 35 SB, at a NSAID:lecithin weight ratio of 1:1. Control rats received an equivalent volume of saline. To make the rats more sensitive to the GI damaging effects of the NSAID all rats also were injected with the nitric oxide (NO) synthase inhibitor, L-NAME (20 mg/kg), three times over the 18-20 hr study period, after which the animals were euthanized and the distal 20 cm of the GI tract was flushed with 2 ml of saline, and the effusate collected for hemoglobin analysis—as an index of GI bleeding. The results of these experiments are shown in FIGS. 2 and 3, below.

Referring now to FIG. 2, data demonstrated that indomethacin, at a dose of 10 mg/kg, induces a severe increase in GI bleeding that is markedly and significantly reduced in rats that were intragastrically administered an equivalent dose if indomethacin in combination with Phosal 35 SB, at a NSAID:lecithin weight ration of 1:1.

Referring now to FIG. 3, data demonstrated that ibuprofen (which is considered one of the least toxic of the conventional NSAIDs in rodent model systems), at a dose of 100 mg/kg induces a modest increase in GI bleeding that is significantly reduced in rats that were intragastrically administered an equivalent dose of ibuprofen in combination with Phosal 35 SB, at a NSAID:lecithin weight ratio of 1:1.

A previously described method was then used to evaluate the anti-inflammatory/analgesic activity of the NSAID-lecithin formulations (in comparison to the NSAIDs alone). This was accomplished be injecting 0.1 ml of Complete Freund's Adjuvant (CFA) into the left hindpaw of rats to induce an acute inflammatory response. Four day later, the rats (which were fasted overnight were intragastrically administered the NSAIDs (either aspirin, indomethacin or ibuprofen) alone on in combination with Phosal 35 SB at a NSAID:lecithin ratio of 1:1 (except in the case of aspirin where other ratios were also evaluated). Two hours later, the rats' pain-sensitivity to pressure was measured, employing the Randall-Sellito technique (55). This was accomplished by incrementally increasing the pressure applied to either the inflamed paw, or the contralateral uninflamed paw, until the animal showed the first sign of pain sensation (either vocalization or extension of the digits on the hindpaw being studied), which was noted as the rat's pain threshold. Thus, a low pain threshold indicates that the inflamed paw is very sensitive to pressure, whereas an increased pain threshold represents low pain sensitivity or analgesia. The results are depicted in FIGS. 4-6.

Referring now to FIG. 4, data demonstrated that aspirin, at a dose of 10 mg/kg, had a modest ability to increase the pain threshold of the rats' affected paw, whereas the analgesic activity of an equivalent dose of aspirin, when administered in combination with lecithin, at all weight ratios tested, was significantly enhanced.

Figure 5:
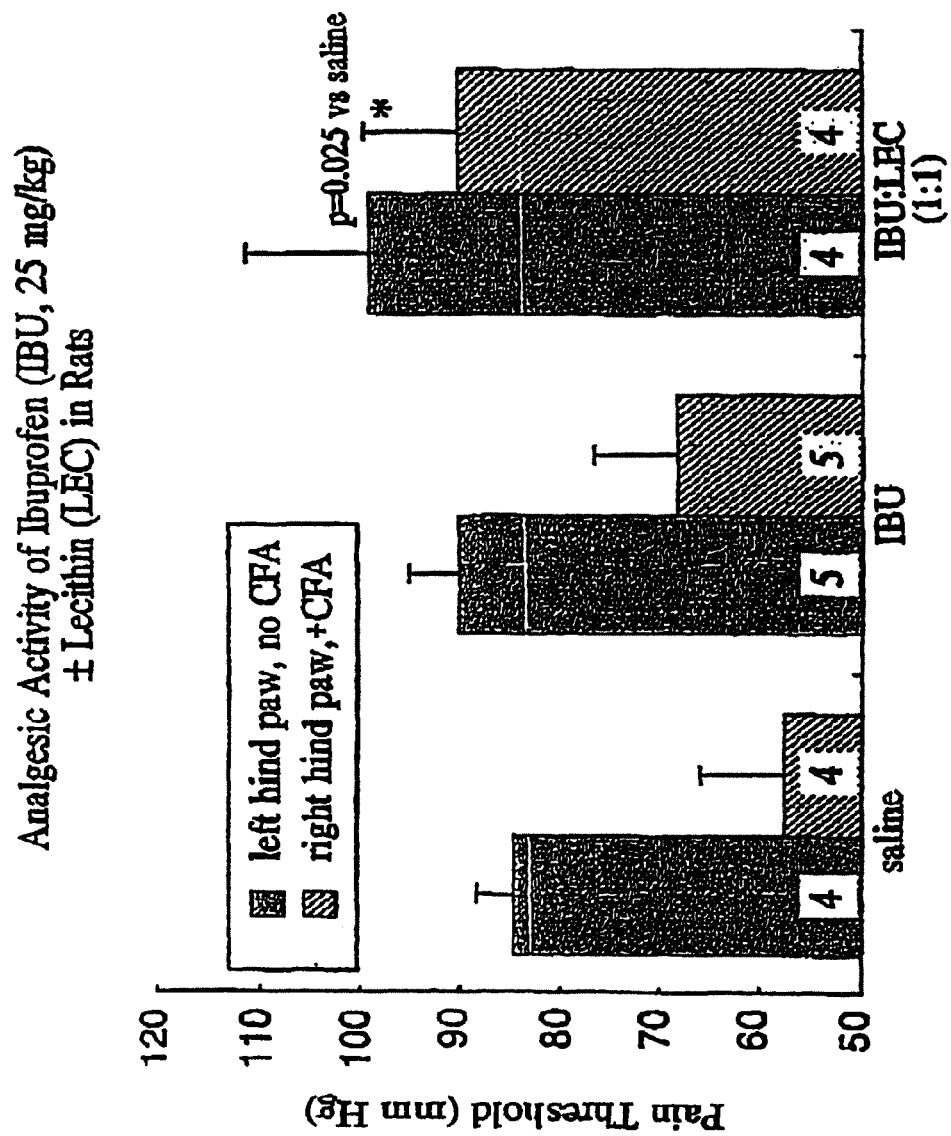
FIG. 5 demonstrates that ibuprofen, at a dose of 25 mg/kg, has a modest though non-significant, ability to increase the pain pressure threshold of the rats' inflamed paw, whereas the analgesic activity of an equivalent dose of ibuprofen, when administered in combination with the lecithin oil at a weight ratio of 1:1, was significantly enhanced.

Referring now to FIG. 5, data demonstrated that ibuprofen, at a dose of 25 mg/kg, has a modest though non-significant, ability to increase the pain pressure threshold of the rats' inflamed paw, whereas the analgesic activity of an equivalent dose of ibuprofen, when administered in combination with the lecithin oil at a weight ratio of 1:1, was significantly enhanced.

Figure 6:
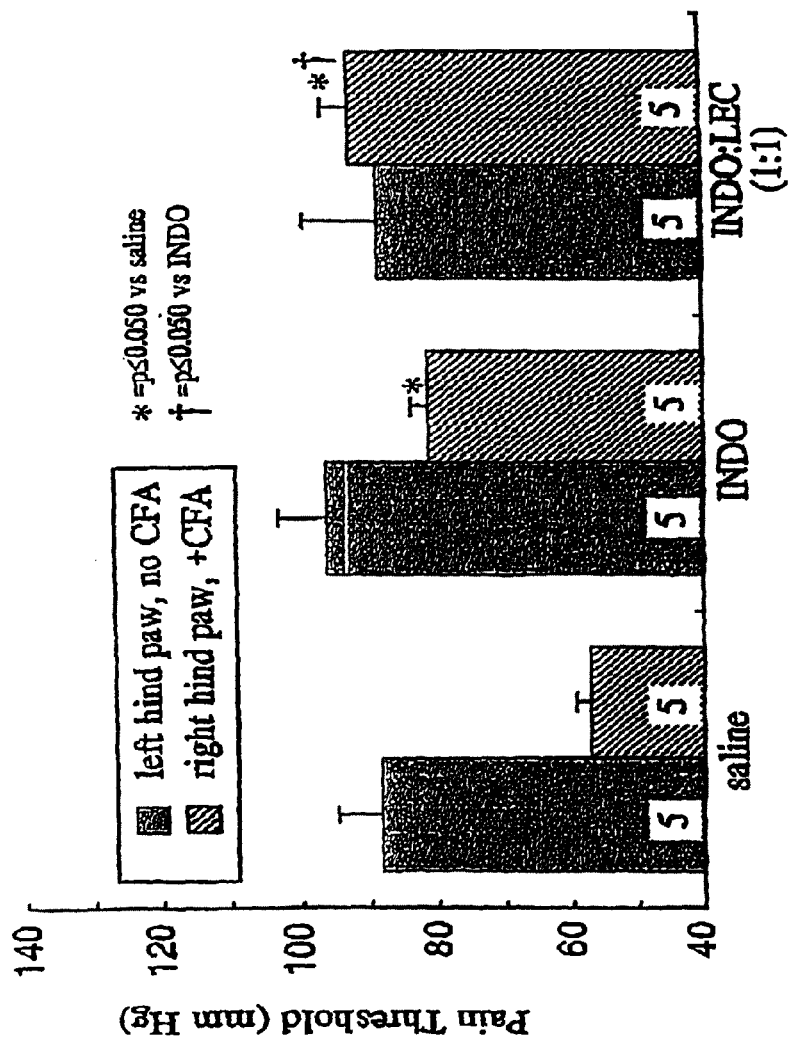
FIG. 6 demonstrates that indomethacin, at a dose of 4 mg/kg, has a modest though non-significant, ability to increase the pain pressure threshold of the rats' inflamed paw, whereas the analgesic activity of an equivalent dose of indomethacin, when administered in combination with the lecithin oil at a weight ratio of 1:1, was significantly enhanced.

Referring now to FIG. 6, data demonstrated that indomethacin, at a dose of 4 mg/kg. The data shows that the paste-like composition provide improved pain handling activity as compared to unmodified INDO and very much improved pain handling activity as compared to the control saline.

NSAIDs and Central and Peripheral Nerves System Trauma and Injury

The process of inflammation is a key component in the progressive pathophysiology associated with both acute, traumatic injuries to the CNS such as spinal cord injury (SCI) [A1] as well as delayed, neurodegenerative diseases such as Alzheimers Disease (AD) [A2]. The process of inflammation is thought to either directly cause, or contribute to, a progressive deterioration in motor function and development of chronic pain as commonly observed in SCI and to the loss of memory and cognitive function observed in AD. Recently, the use of anti-inflammatory drugs has shown efficacy in attenuating tissue loss and functional deficits in a rodent model of traumatic SCI [A3].

Of even greater note, several recent epidemiology studies suggest that chronic consumption of non-steroidal, anti-inflammatory drugs (NSAIDs) may reduce by up to 50% the risk of AD [A4]. As it is conceivable that either acute or chronic NSAID treatment strategies may be utilized, depending on the nature of the inflammatory condition, it is crucial that the NSAIDs are both effective at low doses and well-tolerated with minimal side effects. It is well-established that ~40% of our populace develop gastrointestinal (GI) symptoms in response to chronic NSAID consumption which can range from dyspepsia to the induction of life-threatening episodes of peptic ulceration and bleeding [A5].

In 1995, the PI's laboratory reported that in addition to inhibiting cyclooxygenase (COX) activity, NSAIDs have the capacity to attenuate the surface hydrophobic barrier of the upper GI tract, most probably by chemically associating with a surface lining of phospholipids [A6]. Furthermore, we demonstrated in both laboratory animals and humans that the injurious effect of NSAIDs could be prevented if the drugs were chemically associated with the most prominent phospholipid, phosphatidylcholine (PC) as present as either a synthetic species or a purified extract (e.g. from soy lecithin)

[A6,A7]. Interestingly, it was also demonstrated that in addition to their low GI toxicity, PC-NSAIDs also possess enhanced therapeutic activity to inhibit fever, inflammation and pain, perhaps attributable to their increased membrane permeability and COX inhibitory activity [A6,A8,A9].

Thus, the composition of this invention attenuate neural inflammation and reduce the pathophysiology associated with several neurological conditions including SCI and AD.

Orally-Administered PC-Ibuprofen Reduces the Development of Inflammation-Dependent Hyperalgesia Associated with Peripheral Nerve Ligation It has been reported that placement of four loose ligatures of chromic gut sutures around the sciatic nerve will induce severe peripheral neural inflammation of the affected nerve and the induction of neuropathic pain 2-4 days post surgery, as indicated by a hyperalgesic response to pressure or heat applied to the ipsilateral hindpaw [A10,A11]. The effect of PC-NSAID treatment of peripheral neural inflammation and the reduction of hyperalgesic response using this induction technique in rats. This rodent model was used to induce neural inflammation of either the right or left sciatic nerve using. Sham operations were performed on the contralateral side. Two days post-surgery, the rats were randomly distributed into the following experimental groups (12 rats/group); saline control; ibuprofen (15 mg/kg); and PC-ibuprofen (equivalent dose of the NSAID). The rats were administered the test NSAID formulation b.i.d. for the next two days and several behavioral indices of pain sensation were assessed on both hindpaws before and after the two day dosing period. The behavioral analyses used to assess efficacy were: guarding behavior of the affected hindpaw; paw withdrawal latencies to heat; paw withdrawal response to von Frey hair stimulation; and pain response to the application of pressure to the hindpaw [A8]. At euthanasia, ligated- and control nerves were dissected for both macroscopic and histological examination for indices of inflammation. The results of these studies indicate that the analgesic activity PC-ibuprofen is significantly greater than ibuprofen alone in a model of hindpaw inflammation (induced with Freund's adjuvant), PC-ibuprofen was also more effective in alleviating pain sensitivity due to sciatic nerve ligation, as assessed by measuring the paw withdrawal response to both von Frey hair stimulation and heat.

Orally-Administered PC-Ibuprofen Decreases Tissue Loss, Locomotor Function, and Attenuate the Development of Chronic Pain Syndrome in a Rat Model of Contusive SCI Recently, the delivery of a single dose of an anti-inflammatory drug was shown to reduce the size of a spinal cord lesion in adult rats [A3]. These NSAID-treated rats exhibited greater locomotor activity and decreased symptoms of hyperalgesia and mechanical-allodynia (touch-induced pain), characteristics of neuropathic pain, compared to non-treated rats. The development of chronic, neuropathic pain is an all-too frequent occurrence following spinal cord injury and can become a permanent patient burden. The development of a well-tolerated, effective therapy to prevent or attenuate the development of chronic central pain is desperately needed. Orally administered PC-NSAIDs reduces tissue damage, improves locomotor outcome, and prevents chronic pain syndrome associated with SCI.

PC-Ibuprofen is More Effective than Ibuprofen at Reducing the Development of Alzheimer's-Like Pathophysiology in a Transgenic Mouse Model of AD Recent clinical evidence suggests that NSAIDs may significantly reduce the risk of onset of AD. A major problem is designing treatment strategies for AD has been a lack of adequate animal models. The recently established human β-amyloid-over-expressing Tg2576 mouse provides a convenient rodent model that demonstrates age-dependent memory, cognitive, and histopathological deficits including amyloid plaque-formation, microglial-activation, astrocytic reactivity and dystrophic neurites [A19-A21]. Ibuprofen has recently been shown to reduce numbers of amyloid-plaques, dystrophic neurites and activated microglia in the Tg2576 mouse AD model [A21].

Optimization of the Shelf-Life of PC-NSAIDs

The successful commercialization of a PC-NSAID requires a formulation that remains stable for long periods of time under room temperature conditions. Although this is not a problem for most NSAIDs like ibuprofen, it remains so for aspirin, that rapidly undergoes hydrolysis to salicylic acid if exposed to water. The formulations of this invention based on an NSAID dissolved and/or dispersed in a non-aqueous carrier such as a lecithin oil or any other bio-compatible oil including a phospholipid. Because such environments are hydrophobic, they may result in enhance aspirin stability in aspirin based formulations.

Experimental Results for Central and Peripheral Nerve System Trauma and Injuries These experiments demonstrate PC-ibuprofen is a useful treatment of spinal cord injury (SCI). The results evidence the effects of treating rats with 25 mg of NSAID/kg body weight, two times a day for 6 weeks after spinal cord injury (SCI), comparing PC-ibuprofen, ibuprofen and saline.

Figure 7A:
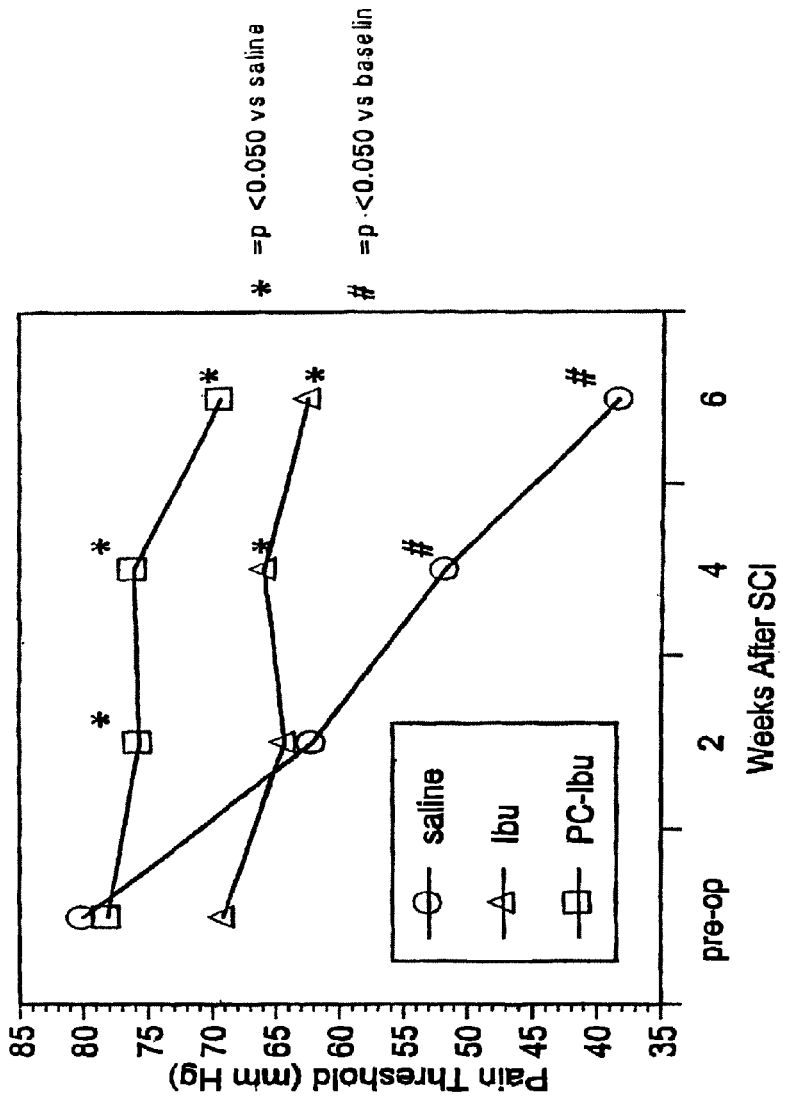
FIG. 7A graphically depicts data relating to hyper-algesia induced by Spinal Cord Injury (SCI) is reversed by treatment with PC-Ibuprofen and Ibuprofen.
Figure 7B:
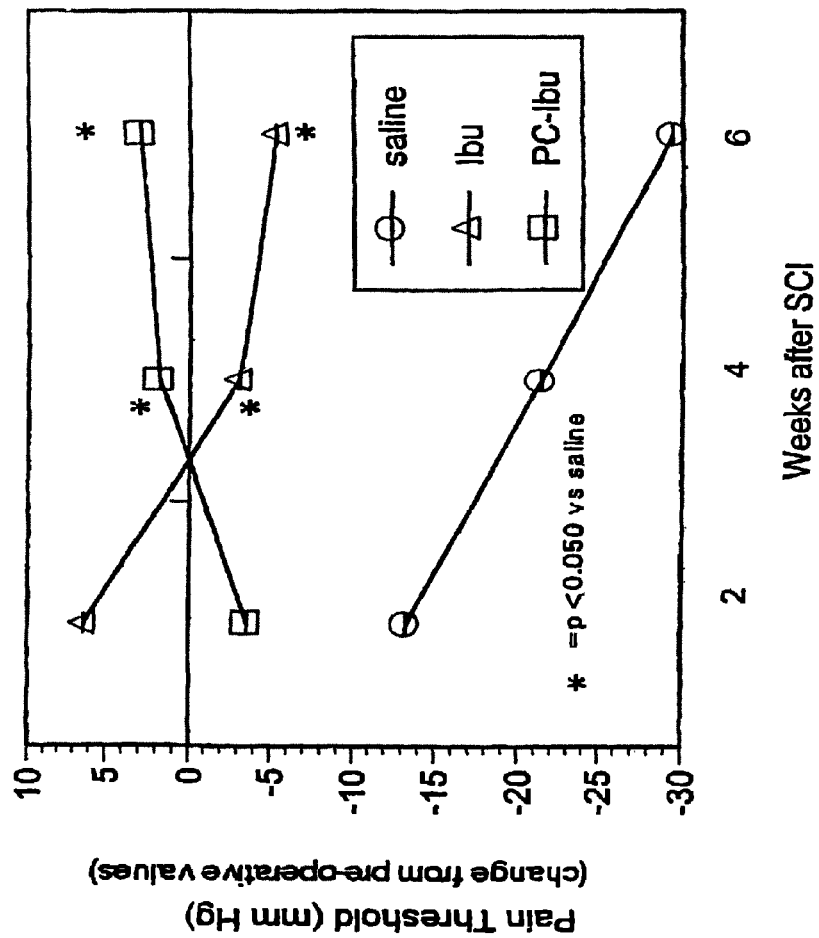
FIG. 7B graphically depicts data relating to hyper-algesia induced by Spinal Cord Injury (SCI) is reversed by treatment with PC-Ibuprofen and Ibuprofen.
Figure 8:
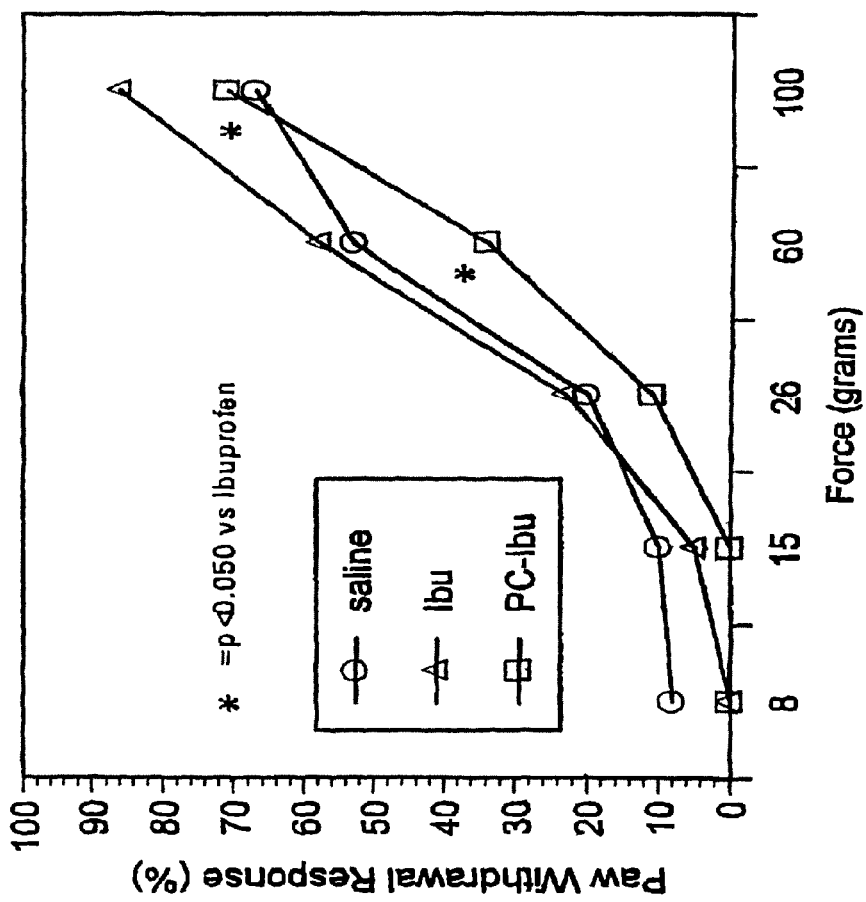
FIG. 8 graphically depicts data relating to analgesic activity of PC-Ibuprofen and Ibuprofen in rats 5 week after spinal cord injury.

Referring to FIGS. 7A and 7B, the graphed data demonstrate that SCI made rats hyperalgesic, as evidenced by a decrease in the pain pressure threshold of saline-treated SCI rats, using the Randall Sellito technique. In contrast, hyperalgesia due to SCI was not seen in SCI rats that were treated with either ibuprofen or PC-ibuprofen, with PC-ibuprofen appearing superior to unmodified ibuprofen. This data is presented in two ways. In FIG. 7A, the data was plotted directly as recorded (without normalization), while in FIG. 7B, the data values for each animal are compared to its own baseline preoperative values. This graphical presentation of the data perhaps is most convincing of the beneficial effects of NSAID administration following SCI.

Referring now to FIG. 8, the superior analgesic activity of PC-ibuprofen in rats with SCI, is also demonstrated in a second behavioral test, where one measures the % of hindpaw responses to stimulation of the hindpaw to fibers (von Frey) hairs having increasing diameters (which is equated to force). Please note that in this case, a lower number is indicative of analgesic, whereas with the Randall Sellito test higher pain pressure threshold values are indicative of analgesia.

Figure 9:
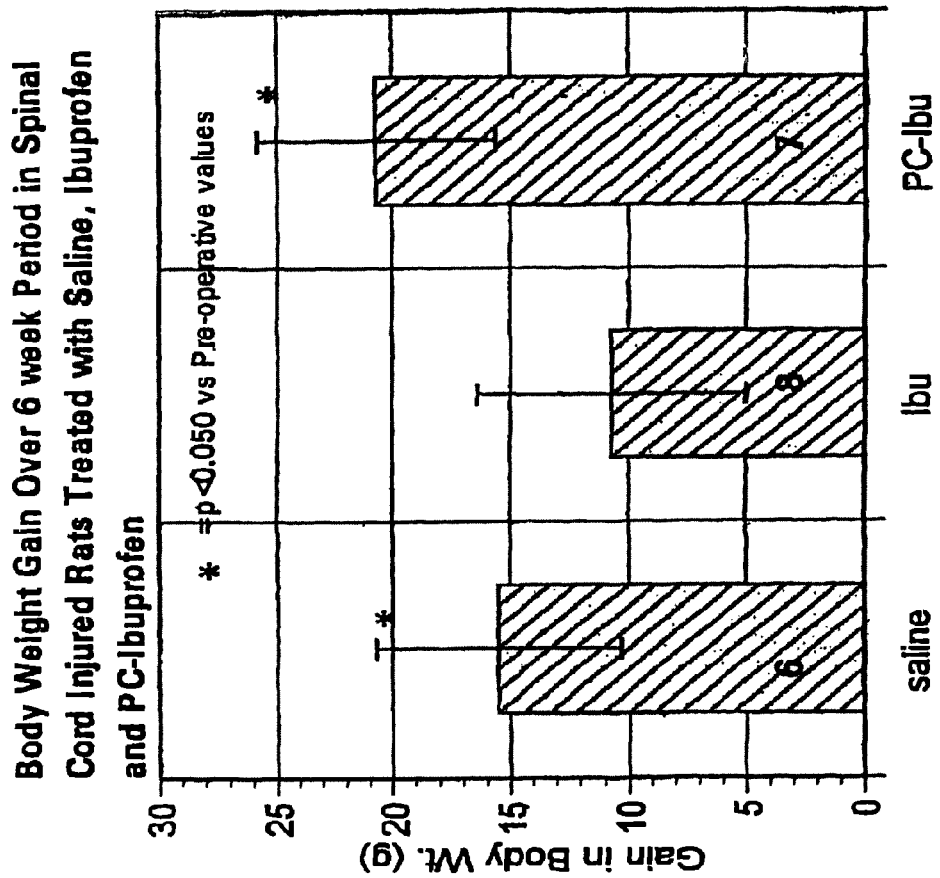
FIG. 9 graphically depicts data relating to body weight gain over 6 week period in Spinal Cord Injured rats treated with PC-Ibuprofen and Ibuprofen.

Referring now to FIG. 9, evidence that SCI rats treated with ibuprofen do not gain weight over the 6 week study period, in contrast to rats treated with saline or PC-ibuprofen. This suggestion that rats with SCI may have a mild-toxic reaction to the ibuprofen alone is also indicated by slight elevations of blood urea nitrogen (evidence of renal toxicity) and lactic dehydrogenase (LDH, evidence of liver toxicity).

Figure 10:
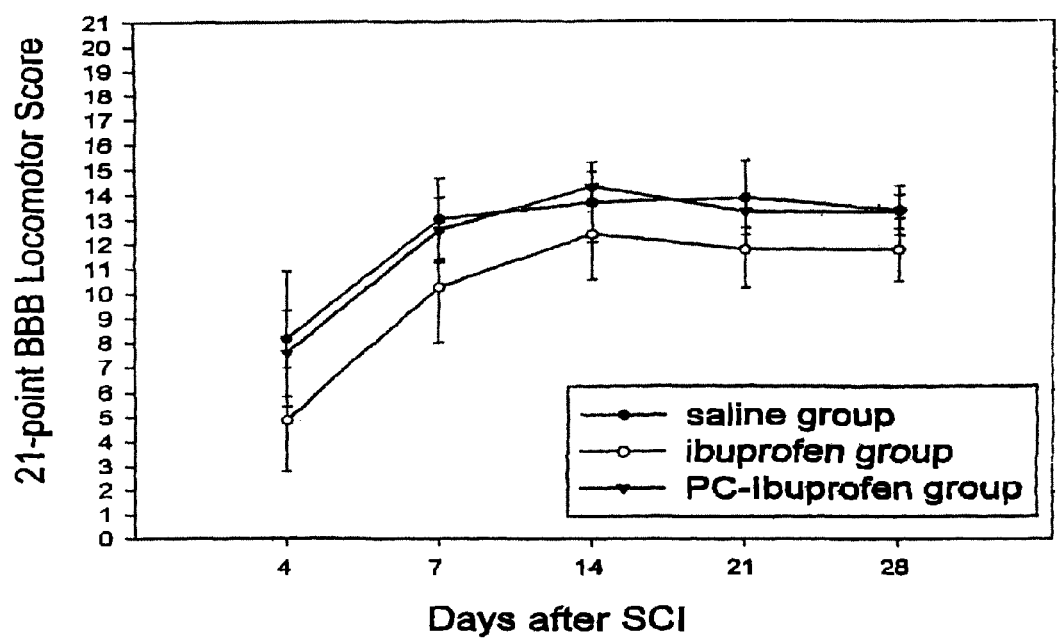
FIG. 10 graphically depicts data relating to recovered motor function after Spinal Cord Injury (SCI) treated with PC-Ibuprofen and Ibuprofen.

Referring now to FIG. 10, evidence that the recovery of motor function after SCI, as assessed by the established BBB test, is attenuated in rats treated with unmodified ibuprofen, whereas there was no difference between saline and PC-ibuprofen groups in this indice of the recovery of motor function.

PC-NSAIDs as Effective Formulation for Treatment of Thrombotic Disorders

The formulations of this invention including a phospholipid such as phosphatidylcholine (PC) and an NSAID, especially aspirin in a bio-compatible oil are effective formulation for the treatment of thrombotic disorders including thrombosis, stroke and myocardial infarction. In addition to its improved GI safety, PC-aspirin is a more potent inhibitor of platelet aggregation and thrombogenesis than regular aspirin. Aspirin (ASA) chemically associates with zwitterionic phospholipids forming an association complex that possess the same or enhanced fever, pain, and inflammation reduction activity as compared to native aspirin, but without aspirin's serious gastrointestinal side-effects of ulceration and bleeding. It is intriguing that phospholipid-complexed aspirin is more potent than aspirin alone in preventing thrombus formation in an in vivo model of arterial thrombosis. Therefore, PC-aspirin formulations of this invention inhibit platelet aggregation and thrombogenesis, reducing the symptoms of thrombotic disorders.

Thrombotic arterial occlusive diseases such as myocardial infarction (MI) and stroke are the leading cause of death in the U.S. and western societies. According to the American Heart Association, over one million Americans will suffer an acute myocardial infarction in the coming year. Drugs that can effectively reduce the incidence of arterial thrombosis are of great clinical importance. As thrombosis is a crucial process in the initiation and propagation of arterial occlusive disease, there is a compelling reason to develop novel, specific antithrombotic drugs. Arterial thrombosis is a complex process involving a series of cellular and biochemical interactions between blood cells, vascular wall and plasma proteins (B1). The blood platelet plays a central role in these interactions (B2). It adheres to the damaged vessel wall, undergoes cellular activation, secretion and aggregation. The activated platelet accelerates blood coagulation, and its secreted molecules promote vascular smooth muscle cell proliferation. In view of the central role that platelets play in arterial thrombosis, major efforts have been made over the years to develop antithrombotic drugs based on inhibition of platelet function (B3). However, few compounds have been clinically useful. In fact, aspirin remains the major drug and the prototype of anti-platelet agents used clinically due to its efficacy and cost considerations. It is effective in primary and secondary prevention of MI and stroke (B4-B7). However, uncertainties remain about aspirin's optimal therapeutic dose, and more than 40% of patients are unable to use aspirin or even enteric-coated aspirin due to gastrointestinal toxicity. Of particular relevance is the recent report that even very low doses of aspirin (10-80 mg) induced gastric erosive injury and bleeding in a significant number of human subjects. This may explain why at present the largest group of hospital admissions for GI bleeding currently are individuals chronically taking low dose aspirin for cardiovascular risk reduction (B8).

The principal mode of action of aspirin and other non-steroidal anti-inflammatory drugs (NSAIDs) has long been known to be through their ability to inhibit prostaglandin synthesis. Two isozymes of cyclooxygenase, COX-1 and COX-2 have been described and NSAIDs block the activities of both COX isoforms (B9-B12). Aspirin exerts its anti-platelet effect by blocking thromboxane $A_2$ ($TXA_2$) production by inhibiting COX-1 activity in platelets. However, aspirin also inhibits the same enzyme in vascular endothelial cells and thus prevents production of prostacyclin ($PGI_2$) (B13,B14). This inhibition of endothelial COX, which may enhance the progression of thrombosis or atherosclerosis, is called the "aspirin dilemma", and is a drawback in its clinical utility. This dilemma has led to the use of low-dose aspirin, suggesting that inhibiting the production of $TXA_2$ while sparing $PGI_2$ can provide the optimal anti-thrombotic conditions to reduce platelet aggregation while maintaining vasodilation. Therefore, a favorable $PGI_2$ to $TXA_2$ ratio may have profound implications for the treatment and prevention of unstable angina, myocardial infarction, transient ischemic attacks, and strokes. With a suitable dose regimen, formulation, and delivery rate, aspirin can possibly prevent platelet $TXA_2$ generation with a minimal interference with vascular $PGI_2$ production (B15-B17).

NSAID Usage in Treating and/or Preventing Thrombosis

NSAIDs, including aspirin are the most heavily consumed drugs among our populace and their use has increased at an exponential rate over the past decade, due to the great efficacy of this family of drugs in the treatment of fever, pain and inflammation (B18). Recent evidence that individuals chronically taking aspirin have a lower incidence than the general population in developing cardiovascular diseases (angina, myocardial infarction, thrombosis, and stroke), have resulted in an ever increasing number of people self-medicating with this drug, accounting for 35-40% of the total annual sales of aspirin (B19). As a consequence, it has been estimated that ~1% of our population are taking an aspirin on a daily basis. As a consequence the FDA has now approved the use of aspirin to reduce the risk of stroke, angina and heart attack. However, uncertainties remain about aspirin's optimal therapeutic dose. One disturbing aspect of the exponential increase in the usage of NSAIDs, which is expected to continue as the average age of our population increases, is that this family of compounds induce serious side-effects in a significant percentage of users, with the most prevalent being gastrointestinal bleeding and ulceration (B20). Of particular relevance is the recent report that even very low doses of aspirin (10-75 mg) induced significant gastric erosive injury and bleeding in human subjects (B8).

Aspirin dosage can be considerably reduced upon association with a zwitterionic phospholipid such as a PC, resulting in a marked improvement in the drug's benefit:risk ratio. Phospholipid-complexed aspirin selectively inhibited platelet $TXA_2$ production relative to vascular $PGI_2$, it is conceivable that these differential effects on platelet and endothelial COX activities of the phospholipid/aspirin complex in comparison to the actions of uncomplexed aspirin are important for its enhanced anti-thrombotic activity. This observation is further supported by the fact that low doses of phospholipid-complexed aspirin in an in vivo model of arterial thrombosis, prevented thrombus formation and vascular occlusion throughout the duration of the experiment, whereas at this sub-threshold dose aspirin alone failed to prevent thrombus formation and the vessel occluded within an hour. It also should be emphasized that an additional benefit of PC-aspirin is that it produces significantly less gastric mucosal injury than regular aspirin and therefore the development of PC-aspirin complex as an effective anti-thrombotic agent without gastrointestinal side effects will have broad, cost effective clinical applications.

Figure 11:
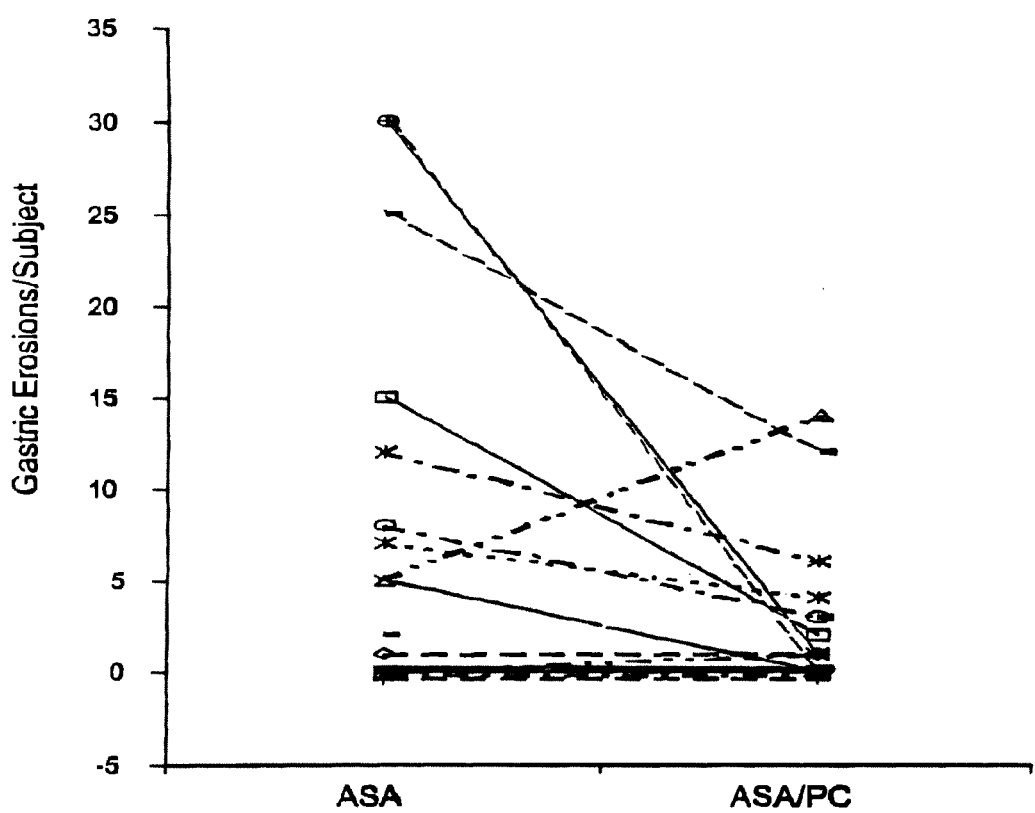
FIG. 11 graphically depicts the PC-aspirin complex significantly reduced the number of gastric erosions by 70% in susceptible individuals in comparison to an equivalent dose of unmodified aspirin and this reduction in gastric toxicity did not relate to an alteration in the COX inhibitory activity of the drug.
Figure 12:
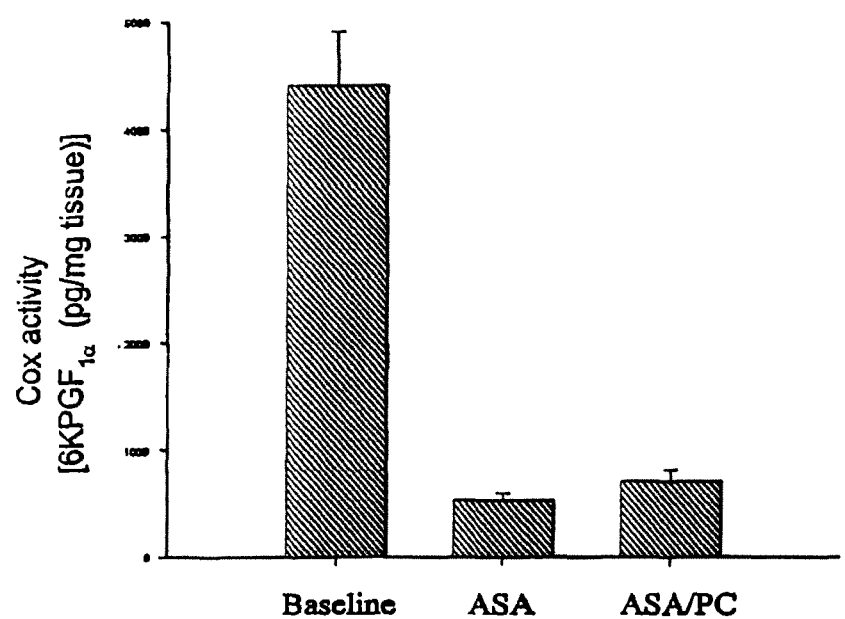
FIG. 12 graphically depicts that both aspirin and PC-aspirin had an equivalent ability to inhibit antral COX activity by >85%.

Results of Principal Investigator:

In 1995, Lichtenberger and his associates (B21) reported in rats that the acute GI injurious actions of orally administered aspirin and a number of other NSAIDs (including diclofenac, indomethacin, and naproxen) could be markedly reduced if the drug was pre-associated with dipalmitoyl phosphatidyl-choline (DPPC), a synthetic PC, or a purified extract of soy lecithin. Recently, the inventor reported (B22) the results of a pilot double blind crossover clinical study, in which sixteen healthy volunteers were orally administered either aspirin or aspirin complexed to PC (650 mg t.i.d.) over a 4-day study period, and mucosal injury was assessed by video-endoscopy. As shown in FIG. 11, the PC-aspirin complex significantly reduced the number of gastric erosions by 70% in susceptible individuals in comparison to an equivalent dose of unmodified aspirin. This reduction in gastric toxicity did not relate to an alteration in the COX inhibitory activity of the drug, as both aspirin and PC-aspirin had an equivalent ability to inhibit antral COX activity by >85% as shown in FIG. 12.

The inventor's laboratory also reported (B23) that the therapeutic activity of aspirin to inhibit fever, inflammation, and pain in rats is consistently enhanced when the NSAID is administered in chemical association with a PC, with its therapeutic potency increasing 5-10 fold over the unmodified NSAID. Additional studies using rodent models of arthritis have also produced confirmatory evidence that a NSAID's potency to inhibit joint inflammation and pain is enhanced if the drug was intragastrically administered in chemical association with a PC.

Figure 13A:
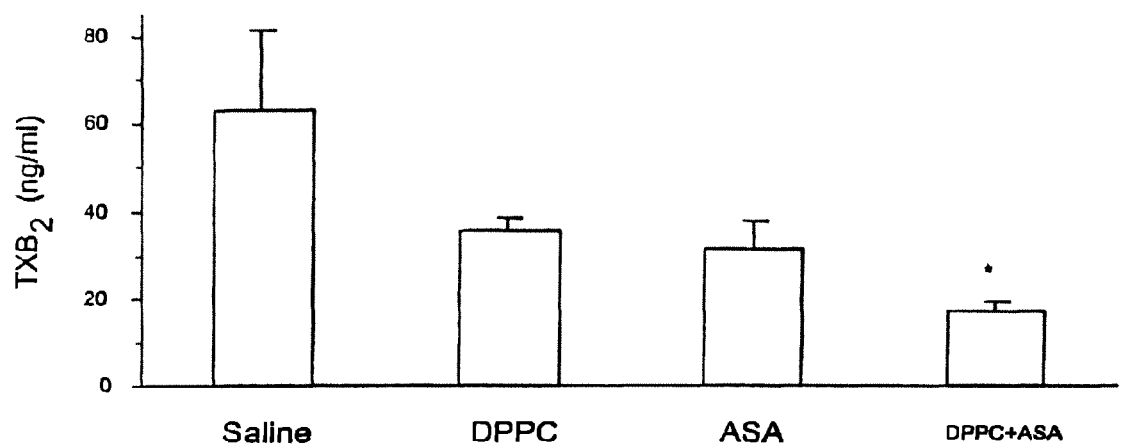
FIGS. 13A&B graphically depicts Concentration of $TXB_2$ in rat platelets, 30 min after oral administration of saline, DPPC, ASA (20 mg/kg), or ASA complexed with DPPC. PRP was prepared and aggregation induced by AA (2 mM). $TXB_2$ was measured by RIA. The results expressed as mean±SEM; n=3. *=p<0.050 vs ASA—Abbreviations: DPPC=dipalmitoylphosphatidylcholine; AA=arachidonic acid; pRP=platelet rich plasma; TXB=thromboxane.

Ex vivo animal studies of the effects of phospholipid-aspirin complex (containing equimolar concentration of the two agents) on the ability to produce $TXA_2$ and $PGI_2$ in platelets and vascular tissue respectively were investigated. Rats were intragastrically administered either unmodified or DPPC-associated aspirin (20 mg/kg dose), and after 30 minutes, blood was drawn, platelet-rich plasma was prepared, and aggregation was induced by arachidonic acid. There was a reduction in $TXB_2$ (a stable metabolite of $TXA_2$) production in the platelets of rats individually treated with unmodified aspirin or DPPC-aspirin as compared to saline control. PC-aspirin, further suppressed the production of $TXB_2$ as shown in FIG. 13A.

Figure 13B:
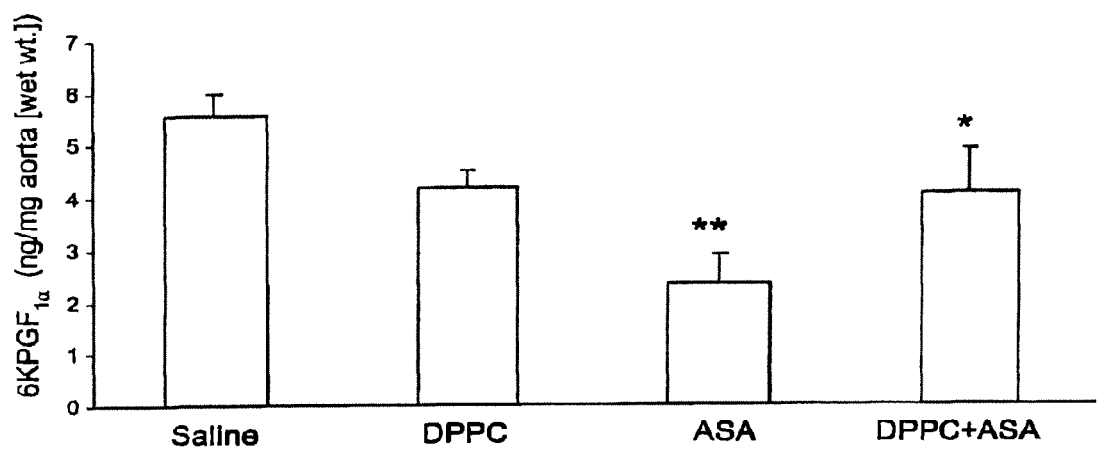
FIG. 13B graphically depicts the effect of intragastric administration to rats of 20 mg/kg ASA alone or complexed with DPPC on 6KPGF1a production by abdominal aorta. After 1 hr the aorta was removed and each aorta ring was incubated at 370 C for 10 min in Tris-HCl buffer containing 25 mM AA. 6KPGF1a was measured by RIA. *=p<0.050 vs ASA; **=p<0.001 vs saline; n=4.

This ex vivo approach was then used to measure vascular (endothelial) $PGI_2$. Abdominal aorta excised one hour after drug administration was evaluated for its ability to produce 6-keto $PGF_{1\alpha}$ (a stable metabolite of $PGI_2$) by incubating it with arachidonic acid (AA, 25 mM). As shown in FIG. 13B, aspirin significantly inhibited the production of 6-keto $PGF_{1\alpha}$, whereas the DPPC alone and DPPC complexed with ASA had no effect, as compared to control. It is, therefore, possible to achieve selective inhibition of platelet cyclooxygenase and preserve vascular prostacyclin biosynthesis by the administration of PC-aspirin.

Figure 14A:
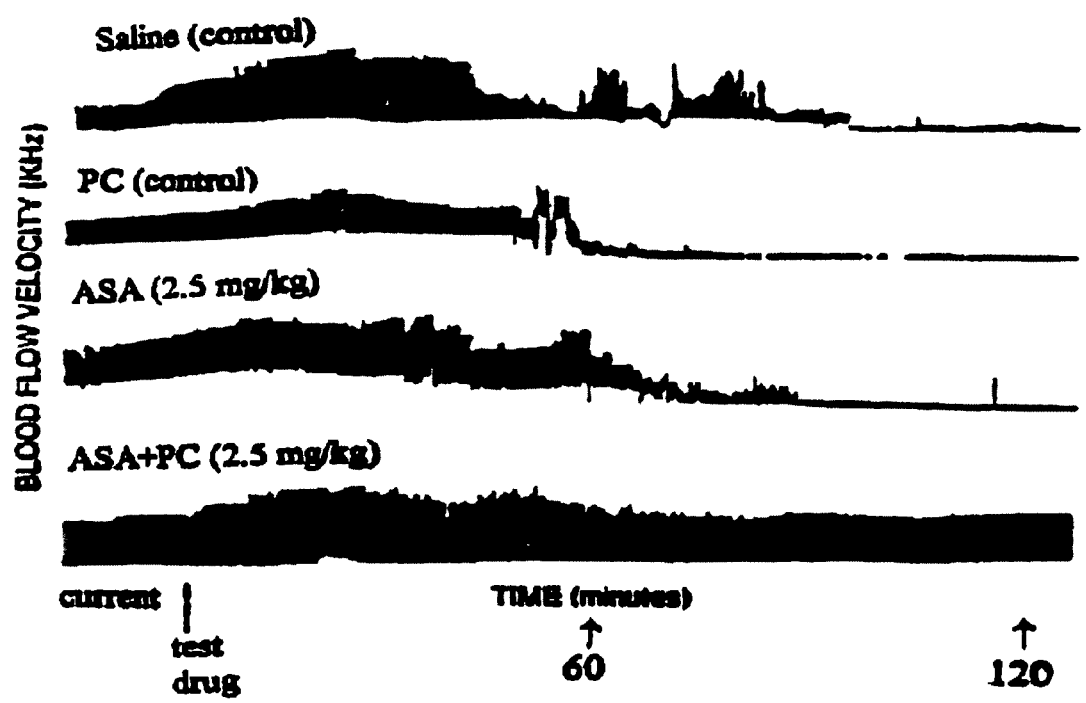
FIG. 14A graphically depicts the representative recording of the blood flow velocities (kHz) from a rabbit during thrombus formation given with 2.5 mg/kg of unmodified aspirin or aspirin complexed to DPPC along with saline or PC controls.
Figure 14B:
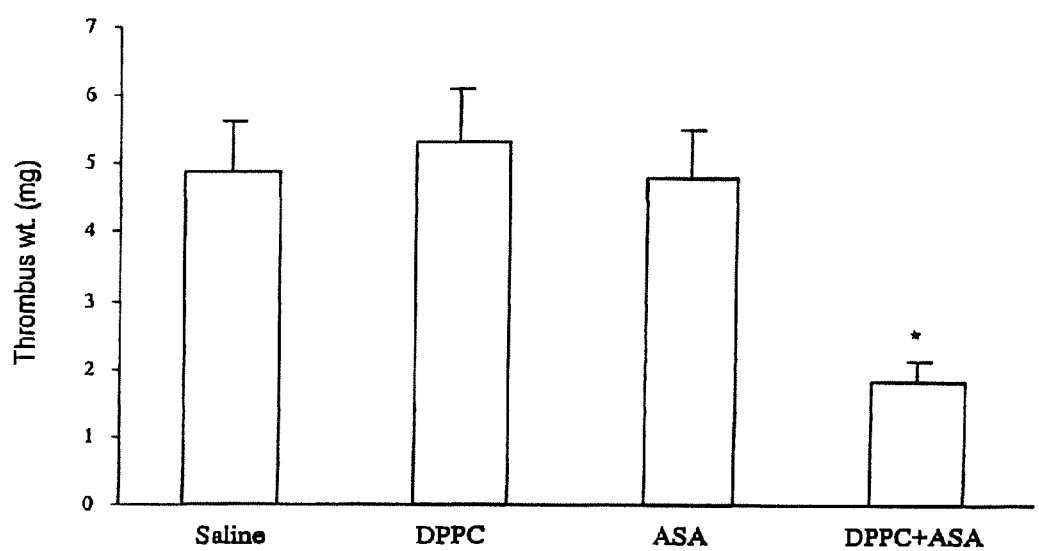
FIG. 14B graphically depicts the effect of 2.5 mg/kg aspirin with or without DPPC on the thrombus wt. in a rabbit arterial thrombosis model. *=p<0.001 vs ASA.

The anti-thrombotic effect of aspirin with or without PC was then evaluated in an in vivo model of arterial thrombogenesis. According to the protocol (B24), the left carotid artery of an anesthetized rabbit was subjected to anodal current to the point where mean carotid blood flow velocity was increased by 50% above control values, which corresponds to 50% occlusion of the vessel by the formed thrombus. At this point the current was discontinued and the test drugs intravenously administered as blood flow was monitored over the next 2-3 hours. It can be appreciated from FIG. 14A that carotid artery blood flow velocity dropped to zero (indicative of complete thrombus occlusion of the vessel) in <60 min in control rabbits treated with either saline or phospholipid alone (mean time until closing=40±17). In contrast, rabbits administered unmodified aspirin, within a 5-20 mg/kg dose range, had no vessel occlusion throughout the duration of the 2-3 hr experiment (data not shown). Interestingly, when the dose of aspirin was reduced to 2.5 mg/kg, it was observed that aspirin complexed with phospholipid was still effective in preventing thrombus formation (>180 min after administration of the complex) whereas aspirin alone (at this sub-threshold dose) failed to prevent thrombus formation and the vessel occluded within 61±15 minutes (n=4) as shown in FIG. 14A. Moreover, the weight of the thrombus formed in rabbits given the aspirin-phospholipid complex at the 2.5 mg/kg dose was significantly smaller than those treated with either native aspirin, saline or phospholipid alone as shown in FIG. 14B.

Figure 14C:
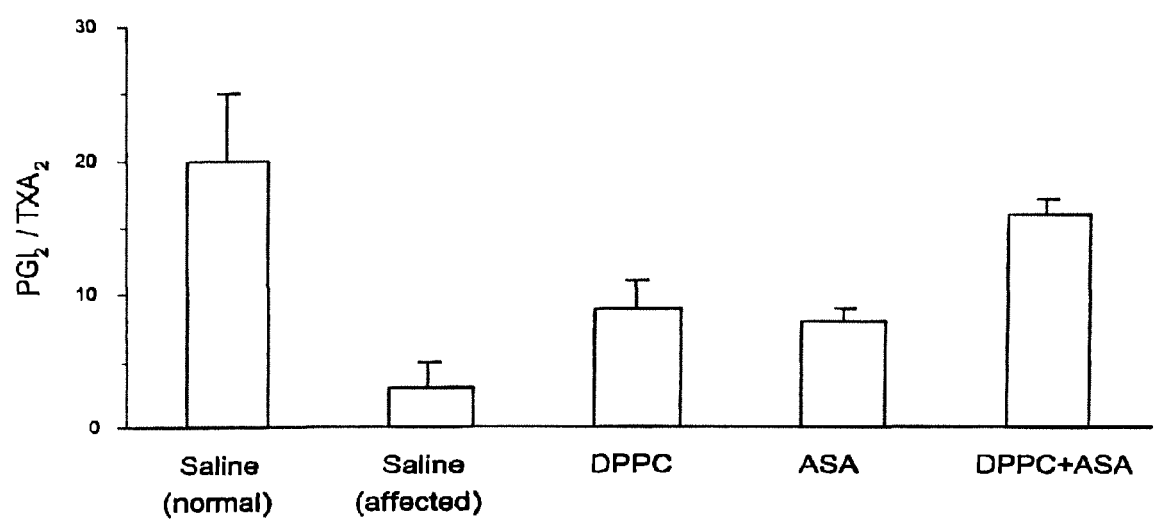
FIG. 14C graphically depicts the effect of 2.5 mg/kg aspirin with or without DPPC on the PGI2 to TXA2 ratio of carotid artery of rabbit arterial thrombosis model.

6-keto $PGF_{1\alpha}$ (a metabolite of $PGI_2$) and $TXA_2$ concentrations was also measured in the affected carotid arteries. In saline control rabbits, the ratio of $PGI_2$ to $TXA_2$ in affected arteries—where the thrombus had formed, was significantly lower (because of increased $TXB_2$ production) than the unaffected (normal) carotid arteries—where no thrombus was generated. This $PGI_2$ to $TXA_2$ ratio improved slightly when the rabbits were treated with aspirin (2.5 mg/kg) or phospholipid alone, but not enough to block the thrombus formation. In contrast the $PGI_2/TXA_2$ ratio in rabbits, which received the same dosage of PC-aspirin, improved significantly and was not significantly different from the ratio determined in the normal arteries (not exposed to anodal current) of saline-treated rabbits as shown in FIG. 14C.

PC-Acetaminophen Formulations

FIG. 15 graphically depicts data indicating that a 1:2 ratio of acetaminophen (Tylenol):P35 SB provides rats with protection from liver injury as indicated by elevations of the liver enzyme aspartate transaminase (AST), 24 hrs after fasted Sprague Dawley rats are orally challenged with either Tylenol alone or the above Tylenol:P35 SB combinations. The data shows that by using several statistical tests it appears that AST levels are significantly elevated in the Tylenol treated rats vs saline control values, but not in the rats administered the Tylenol:P35 SB combination at a 1:2 wt ratio.

REFERENCES

1. Furst D E, Paulus H E. Aspirin and other nonsteroidal anti-inflammatory drugs. In: *Arthritis and Allied Conditions* (McCarty D J, Koopman W J, Eds) Lea & Febiger, Philadelphia, 1993, pg 567-602.
2. Pelletier J-P. Pathological pathways of osteoarthritis. In: *Non-steroidal Anti-inflammatory Drugs: A Research and Clinical Perspective*. Royal Society of Medicine Press, London, 1994, 1-14.
3. Jiang Y, Zhao J, Genant H K, Dequeker J, Geusens P. Bone mineral density and biomechanical properties of spine and femur of ovariectomized rats treated with naproxen. *Bone* 22: 509-514, 1996.
4. Walt R., Katschinski B, Logan R, Ashley J, Langman M. Rising frequency of ulcer perforation in elderly people in the United Kingdom. *Lancet* 489-492, 1986.
5. Allison M C, Howatson A G, Torrance C J, Lee F D, Russel R I: Gastrointestinal damage associated with the use of nonsteroidal anti-inflammatory drugs. N. Engl J. Med. 327:749-754, 1992.
6. Kurata J H, Abbey D E. The effect of chronic aspirin use on duodenal and gastric ulcer hospitalizations. *J Clin. Gastroenterol.* 12(3):260-266, 1990.
7. Symmons D P M. Mortality in rheumatoid arthritis. *Br. J. Rheum.* 27 (Suppl 1): 44-54, 1988.
8. Henry D A, Johnston A, Dobson A, Duggan J. Fatal peptic ulcer complications and the use of non-steroidal anti-inflammatory drugs, aspirin and corticosteroids. *Br. Med. J* 295:1227-1229, 1987.
9. Vane J R. Inhibition of prostaglandin synthesis as a mechanism of action of aspirin-like drugs. *Nature* 231:232-251, 1971.
10. Ferreira S H Vane J R. New aspects of the mode of action of NSAIDs. *Ann Rev Pharmacol* 14: 57-.70, 1974
11. Whittle B J R, Higgs G A, Eakin K E, Moncada S, Vane J R. Selective inhibition of prostaglandin production in inflammatory exudates and gastric mucosa. *Nature* 284: 271-273, 1980.
12. Bergstrom S, Duner H, von Euler U S, Pernow B, Sjovall J. Observations on the effects of infusions of prostaglandin E in man. *Acta Physiol Scand.* 45: 145-152, 1959.

13. Robert A. Nezamis J E, Lancaster C, Hanchar A J: Cytoprotection by prostaglandins in rats: prevention of gastric necrosis produced by alcohol, HCL, NaOH, hypertonic NaCl and thermal injury. *Gastroenterology* 70: 359-370, 1979.
14. Mitchell J A, Akarasreenont P, Thiemermann C, Flower R J, Vane J R. Selectivity of NSAIDs as inhibitors of constitutive and inducible cyclo-oxygenase. *P.N.A.S.* 90:11693-11697, 1993.
15. Masferrer J L, Zioeifel B S, Manning P T, Hauser S D, Leahy K M, Smith W G, Isakson P C, Seibert K. Selective inhibition of inducible cyclo-oxygenase-2 in vivo is anti-inflammatory and non-ulcerogenic. *P.N.A.S.* 91:3228-3232, 1994.
16. Xie W, Chipman J G, Robertson D L, Erikson R L, Simmons D L. Expression of a mitogen responsive gene encoding prostaglandin synthesis is regulated by mRNA splicing. *P.N.A.S.* 88: 2692-2696, 1991.
17. O'Banion M K, Sardowski H B, Winn V, Young D A. A serum and glucocorticoid regulated 4-kilobase RNA encodes a cyclooxygenase-related protein. *J Biol Chem* 266:23261-7, 1991.
18. Meade E A, Smith W L, Dewitt D L. Differential inhibition of prostaglandin endoperoxide synthase (cyclooxygenase) isozymes by aspirin and other nonsteroidal anti-inflammatory drugs. *J Biol Chem* 268: 6610-6614, 1993.
19. Masferrer J L, Zioeifel B S, Manning P T, Hauser S D, Leahy K M, Smith W G, Isakson P C, Seibert K. Selective inhibition of inducible cyclo-oxygenase-2 in vivo is anti-inflammatory and non-ulcerogenic. *P.N.A.S.* 91:3228-3232, 1994. mRNA encodes a cyclooxygenase-related protein. *J Biol Chem* 1991; 266: 23261-7.
20. Lipsky P E, Isakson P C. Outcome of specific COX-2 inhibition in rheumatoid arthritis. *J Rheumatol* 24(Suppl 49): 9-14, 1997.
21. Bjarnason 1, Macpherson A, Rotman H, Schupp, Hayllar J. A randomized double-blind, cross-over study on the gastroduodenal tolerability of a highly specific cyclo-oxygenase-2 inhibitor, flosulide and naproxen. *Scand J Gastroenterol* 32: 126-130, 1997.
22. Simon L S, Lanza F L, Lipsky P E et. al. Preliminary safety and efficacy of SC-58635, a novel COX-2 inhibitor. *Arthritis Rheum* 41: 1591-1602, 1998.
23. Laine L, Harper S, Simon T, Bath T, Johanson J, Schwartz H, Stern S, Quan H, Bolognese J. A randomized trial comparing the effect of Rofecoxib, a cyclooxygenase 2-specific inhibitor, with that of ibuprofen on the gastroduodenal mucosa of patients with osteoarthritis. *Gastroenterology* 117: 776-783, 1999.
24. Will super aspirin supersede aspirin *Modern Drug Discovery* May/June 54-59, 1999.
25. Ligumsky M, Grossman M I, Kauffman Jr G L. Endogenous gastric mucosal prostaglandins: their role in mucosal integrity. *Am. J. Physiol.* 242:G337-341, 1982.
26. Ligumsky M, Golanska E M, Hansen D G, Kauffman Jr G L. Aspirin can inhibit gastric mucosal cyclo-oxygenase without causing lesions in the rat. *Gastroenterology* 84; 756-761, 1983.
27. Ligumsky M, Sestieri M, karmeli F, Zimmerman J, Okon E, Rachmilewitz D. Rectal administration of nonsteroidal antiinflammatory drugs. *Gastroenterology* 98: 1245-1249, 1990.
28. Whittle B J R. Temporal relationship between cyclooxygenase inhibition, as measured by prostacyclin biosynthesis and the gastrointestinal damage induced by indomethacin in the rat. *Gastroenterology* 80:94-98, 1981.
29. Ivey K K, Paone D B, krause W J. Acute effect of systemic aspirin on gastric mucosa in man. Dig. Dis Sci. 25: 97-99, 1980.
30. Konturek J W, Dembinski A, Konturek S J, Stachura J, Domschke W. Infection of *Helicobacter pylori* in gastric adaptation to continued aspirin administration in human subjects. *Gastroenterology* 114: 245-255, 1998.
31. Langerbach R, Morham S G, Tiano H F, Loftin C D et. al. Prostaglandin synthase 1 gene disruption in mice reduces arachidonic acid-induced inflammation and indomethacin-induced gastric ulceration. *Cell* 83:483-492, 1995.
32. Morham S G, Langenbach R, Loftin C D et. al. Prostaglandin synthase 2 gene disruption causes severe renal pathology in the mouse. *Cell* 83: 473-482, 1995.
33. Mizuno H, Sakamoto C, Matsuda K et. al. Induction of COX-2 in gastric mucosal lesions and its inhibition by the specific antagonist delays healing in mice. *Gastroenterology* 112: 387-397, 1997.
34. Reuter B K, Asfaha S, Buret A, Sharkey K A, Wallace J L. Exacerbation of inflammation-associated colonic injury in rat through inhibition of cyclooxygenase-2. *J Clin Invest* 98: 2076-2085, 1996.
35. Wallace J L. Nonsteroidal anti-inflammatory drugs and gastroenteropathy: the second hundred years. *Gastroenterology* 112: 1000-1016, 1997.
36. Wallace J L, Keenan C M, Granger D N. Gastric ulceration induced by nonsteroidal anti-inflammatory drugs is a neutrophil-dependent process. *Am J. Physiol.* 259: G462-467, 1990.
37. McCafferty D-M, Granger D N, Wallace J L. Indomethacin-induced gastric injury and leukocyte adherence in arthritic vs healthy rats. *Gastroenterology* 109; 1173-1180, 1995.
38. Mahmud T, Rafi, S S, Scott, D L, Wrigglesworth J M, Bjarnason I. Nonsteroidal antiinflammatory drugs and uncoupling of mitochondrial oxidative phosphorylation. *Arthritis Rheum* 39: 1998-2003, 1996.
39. McCormack K, Brune K. Classical absorption theory and the development of gastric mucosal damage associated with non-steroidal anti-inflammatory drugs. Arch Toxicol 60: 261-269, 1987.
40. Lichtenberger, L M. The hydrophobic barrier properties of gastrointestinal mucus. *Ann. Rev. Physiol.* 57: 565-583, 1995.
41. Hills B A, Butler B D, Lichtenberger L M. Gastric Mucosal Barrier: The hydrophobic lining to the lumen of the stomach. *Am. J. Physiol.: Gastrointestinal and Liver Physiology* 7:G561-68, 1983.
42. Lichtenberger L M, Graziani L A, Dial E J, Butler B D, Hills B A. Role of surface-active phospholipids in gastric cytoprotection. *Science* 219:1327-29, 1983.
43. Spychal R T, Marrero J M, Saverymuttu S H, Northfield T C. Measurement of the surface hydrophobicity of human gastrointestinal mucosa. *Gastroenterology* 97: 104-11, 1989.
44. Go M F, Lew G M, Lichtenberger L M, Genta R M, Graham D Y. Gastric mucosal hydrophobicity and *Helicobacter pylori*: response to antimicrobial therapy. *Am J Gastroenterol* 88: 1362-65, 1993.
45. Butler B D, Lichtenberger L M, Hills B A. Distribution of surfactants in the canine GI tract and their ability to lubricate. *Am. J. Physiol: Gastrointestinal and Liver Physiology* 7:G 645-51, 1983.
46. Kao Y-C J, Lichtenberger L M. A method to preserve extracellular surfactant-like phospholipids on the luminal surface of the rodent gastric mucosa. *J. Histochem. Cytochem.* 38:427-31, 1990.

47. Kao Y-C J, Lichtenberger L M. Phospholipid- and neutral-lipid-containing organelles of rat gastroduodenal mucous cells. *Gastroenterology* 101:7-21, 1991.
48. Goddard P J, Lichtenberger L M. Does aspirin damage the canine gastric mucosa by reducing its surface hydrophobicity? *Am. J. Physiology: Gastrointestinal and Liver Physiology* 15:G421-30, 1987.
49. Goddard P J, Kao Y-C J, Lichtenberger L M. Luminal surface hydrophobicity of canine gastric mucosa is dependent on a surface mucous gel. *Gastroenterology* 98:361-70, 1990.
50. Dial E J, Lichtenberger L M. A role for milk phospholipids in protection against gastric acid. *Gastroenterology* 87: 379-385, 1984.
51. Lichtenberger L M, Romero J J, Kao Y-C, Dial E J. Gastric protective activity of mixtures of saturated polar and neutral lipids in rats. *Gastroenterology* 99; 311-326, 1990.
52. Lichtenberger L M, Wang Z-M, Romero J J, Ulloa C, Perez J C, Giraud M-N, Barreto J C. Non-steroidal anti-inflammatory drugs (NSAIDs) associate with zwitterionic phospholipids: Insight into the mechanism and reversal of NSAID-induced gastrointestinal injury. *Nature Medicine* 1: 154-158, 1995.
53. Anand B S, Romero J J, Sanduja S K, Lichtenberger L M. Phospholipid association reduces the gastric toxicity of aspirin in human subjects. *Am J Gastroenterol* 94: 1818-1822, 1999.
54. Lichtenberger L M, Ulloa C, Vanous A L, Romero J J, Dial E J, Illich P A, Walters E T. Zwitterionic phospholipids enhance aspirin's therapeutic activity, as demonstrated in rodent model systems. *JPET* 1996; 277: 1221-1227.
55. Randall L O, Selitto J J. A method for measurement of analgesic activity of inflamed tissue. *Arch. Int. Pharmacodyn.* 111: 409-411, 1957.0
A1. Faden, A. I., *Experimental neurobiology of central nervous system trauma*. Crit Rev Neurobiol, 1993. 7(3-4): p. 175-86.
A2. Rogers, J., et al., *Inflammation and Alzheimer's disease pathogenesis*. Neurobiol Aging, 1996. 17(5): p. 681-6.
A3. Hains, B. C., J. A. Yucra, and C. E. Hulsebosch, *Reduction of pathological and behavioral deficits following spinal cord contusion injury with the selective cyclooxygenase-2 inhibitor NS-398*. J Neurotrauma, 2001. 18(4): p. 409-23.
A4. Stewart, W. F., et al., *Risk of Alzheimer's disease and duration of NSAID use*. Neurology, 1997. 48(3): p. 626-32.
A5. Gabriel, S. E., L. Jaakkimainen, and C. Bombardier, *Risk for serious gastrointestinal complications related to use of nonsteroidal anti-inflammatory drugs. A meta-analysis*. Ann Intern Med, 1991. 115(10): p. 787-96.
A6. Lichtenberger, L. M., et al., *Non-steroidal anti-inflammatory drugs (NSAIDs) associate with zwitterionic phospholipids: insight into the mechanism and reversal of NSAID-induced gastrointestinal injury*. Nat Med, 1995. 1(2): p. 154-8.
A7. Anand, B. S., et al., *Phospholipid association reduces the gastric mucosal toxicity of aspirin in human subjects*. Am J Gastroenterol, 1999. 94(7): p. 1818-22.
A8. Lichtenberger, L. M., et al., *Zwitterionic phospholipids enhance aspirin's therapeutic activity, as demonstrated in rodent model systems*. J Pharmacol Exp Ther, 1996. 277(3): p. 1221-7.
A9. Lichtenberger, L. M., et al., *Phosphatidylcholine association increases the anti-inflammatory and analgesic activity of ibuprofen in acute and chronic rodent models of joint inflammation: relationship to alterations in bioavailability and cyclooxygenase-inhibitory potency*. J Pharmacol Exp Ther, 2001. 298(1): p. 279-87.
A10. Clatworthy, A. L., et al., *Role of peri-axonal inflammation in the development of thermal hyperalgesia and guarding behavior in a rat model of neuropathic pain*. Neurosci Lett, 1995. 184(1): p. 5-8.
A11. Coggeshall, R. E., et al., *Is large myelinated fiber loss associated with hyperalgesia in a model of experimental peripheral neuropathy in the rat?* Pain, 1993. 52(2): p. 233-42.
A12. Carlson, S. L., et al., *Acute inflammatory response in spinal cord following impact injury*. Exp Neurol, 1998. 151(1): p. 77-88.
A13. Hirst, W. D., et al., *Expression of COX-2 by normal and reactive astrocytes in the adult rat central nervous system*. Mol Cell Neurosci, 1999. 13(1): p. 57-68.
A14. Resnick, D. K., et al., *Role of cyclooxygenase 2 in acute spinal cord injury*. J Neurotrauma, 1998. 15(12): p. 1005-13.
A15. Plunkett, J. A., et al., *Effects of interleukin-10 (IL-10) on pain behavior and gene expression following excitotoxic spinal cord injury in the rat*. Exp Neurol, 2001. 168(1): p. 144-54.
A16. Basso, D. M., M. S. Beattie, and J. C. Bresnahan, *A sensitive and reliable locomotor rating scale for open field testing in rats*. J Neurotrauma, 1995. 12(1): p. 1-21.
A17. Grill, R., et al., *Cellular delivery of neurotrophin-3 promotes corticospinal axonal growth and partial functional recovery after spinal cord injury*. J Neurosci, 1997. 17(14): p. 5560-72.
A18. Rabchevsky, A. G., et al., *Cyclosporin A treatment following spinal cord injury to the rat: behavioral effects and stereological assessment of tissue sparing*. J Neurotrauma, 2001. 18(5): p. 513-22.
A19. Hsiao, K., et al., *Correlative memory deficits, Abeta elevation, and amyloid plaques in transgenic mice*. Science, 1996. 274(5284): p. 99-102.
A20. Hsiao, K., *Transgenic mice expressing Alzheimer amyloid precursor proteins*. Exp Gerontol, 1998. 33(7-8): p. 883-9.
A21. Lim, G. P., et al., *Ibuprofen suppresses plaque pathology and inflammation in a mouse model for Alzheimer's disease*. J Neurosci, 2000. 20(15): p. 5709-14.
A22. Morris, R., *Developments of a water-maze procedure for studying spatial learning in the rat*. J Neurosci Met, 1984. 11(1): p. 47-60.
A23. Lichtenberger, L. M., R. Darling, and J. J. Romero, *Effect of luminal damaging agents on the gastric mucosal barrier and prostaglandin metabolism in cyclooxygenase (COX) knockout mice*. Gastroenterology, 2001. 120: p. A-143.
B1. Wu K K. Thrombogenesis, Atherogenesis and Hypercoagulability in "Thromboembolic Disorders" edited by Wu K K. PSG Publisher, Littleton, Mass., 1984, pp 5-18.
B2. Schafer A I, Handin R I. The role of platelets in thrombotic and vascular disease. Progr Cardiovasc Dis 22:31, 1979.
B3. Fuster V, Chesbro J H. Platelet inhibitor drugs in management of arterial thromboembolic and atherosclerotic disease. Mayo Clinic Proc. 56:265, 1981.
B4. Fields W S, Lemak N A, Frankowsk R F, Hardy R J. Controlled trial of aspirin in cerebral ischemia. Stroke 8:301-314, 1977.
B5. Canadian Cooperative Study Group. A randomized trial of aspirin and sulfide pyrazone in threatened stroke. New Eng J Med 299:53-59, 1978.

B6. Lewis H D Jr, Davis J W, Arclirbald D G, et al. Protective effects of aspirin against acute myocardial infarction and death in man with unstable anginas. Results of a V A cooperative study. N Eng J Med 313: 396, 1983.

B7. The Steering Committee of the Physicians Health Study Research Group Preliminary Report: Findings from the aspirin component of the ongoing physicians health study. N Eng J Med 318:362, 1988.

B8. Cryer B, Feldman M. Effects of very low dose daily, long term aspirin therapy on gastric, duodenal, and rectal prostaglandin levels and on mucosal injury. Gastroenterology 117: 17-25, 1999.

B9. Vane J. Towards a better aspirin. Nature 367:215-216, 1994.

B10. Smith W L, DeWitt D L. Biochemistry of prostaglandin endoperoxide H synthase-1 and synthase-2 and their differential susceptibility to non-steroidal anti-inflammatory drugs. Seminars in Nephro. 15:179, 1995.

B11. Rome L H, Lands W E M. Structure requirements for time dependent inhibition of prostaglandin biosynthesis by anti-inflammatory drugs. Proc Natl Acad Sci USA 72:4863-4865, 1975.

B12. Laneuville O, Breuer D K, DeWitt D L et. al. Differential inhibition of human prostaglandin endoperoxide H synthase-1 and -2 by non steroidal anti-inflammatory drugs. J Pharm Exp Ther 271:927-934, 1994.

B13. Vane J R. Inhibition of prostaglandin synthesis as a mechanism of action of aspirin-like drugs. Nature 231:232, 1971.

B14. Roth G J, Majerus P W. The mechanism of the effect of aspirin on human platelets 1. Acetylation of a particular fraction protein. J Clin Invest 56:624-632, 1975.

B15. Hennekens C H, Buring J E. Aspirin and cardiovascular disease. Bull N Y Acad Med 65:57-68, 1989.

B16. Viinikka L. Acetylsalicylic acid and the balance between prostacyclin and thromboxane. Scand J Clin Lab Invest 50(supple 201): 103, 1990.

B17. Lekstrom J A, Bell W R. Aspirin in the prevention of thrombosis. Med 70:161, 1991.

B18. Gabriel S E, Fehring R A. Trends in the utilization of non-steroidal anti-inflammatory drugs in the United States, 1986-1990. J Clin Epidemiol 45: 1041-1044, 1992.

B19. Keifer D M; A century of pain relief. Todays Chemist at Work, Dec. 38-42, 1997.

B20. Gabriel S E, Jaakkimainen R, Bombardier C. Risk for serious gastrointestinal complications related to the use of nonsteroidal anti-inflammatory drugs. Ann Int Med 115: 787-796, 1991.

B21. Lichtenberger L M, Wang Z M, Romero J J, Ulloa C, Perez J, Giraud M-N, Barreto J C. NSAIDs associate with zwitterionic phospholipids: Insight into the mechanism and reversal of NSAID-induced G.I. injury. Nature Medicine 1:154-158, 1995.

B22. Anand B S, Romero J J, Sanduja S K, Lichtenberger L M. Evidence that phospholipid reduces the gastric toxicity of aspirin in human subjects. Am J Gastroenterol 94: 1818-1822, 1999.

B23. Lichtenberger L M, Ulloa C, Vanous A L, Romero J J, Dial E J, Illich P A, Walters E T. Zwitterionic phospholipids enhance aspirin's therapeutic activity, as demonstrated in rodent model systems. J Pharm Exp Therap 277:1221-1227, 1996.

B24. Benedict C R, Refino C J, Keyt B A, Pakala R, Paoni N F, Thomas R, Bennett W F. New variant of human tissue plasminigen activator (TPA) with enhanced efficacy and lower incidence of bleeding compared with recombinant human TPA. Circulation 92: 3032-3040, 1995.

B25. Blake P R, Summers M F. NOESY-1-1 Ech spectroscopy with eliminated radiation damping. J Magn Res 86: 622-625, 1990.

B26. Pinon J F. In vivo study of platelet aggregation in rats. J Pharmaco Methods 12:79, 1984.

B27. Triplett D A, Harms C S, Newhouse P, Clark C. Platelet Function: Laboratory evaluation and clinical application. Edited by Triplett D A. American Society of Clinical Pathologists, Chicago, 1978.

B28. Sanduja S K, Mehta K, Xu X-M, Sanduja R and Wu K K. Differentiation associated expression of prostaglandin H and thromboxane A synthases in monocytoid leukemia cell lines. Blood 78:3178-3185, 1991.

B29. Sanduja S K, Tsai A L, Aleksic N M, Wu, K. K. Kinetic of Prostacyclin Synthesis in PGHS-1 Overexpressed Endothelial cells. *Am. J. Physiol,* 267: C1459-1466, 1994.

B30. Gambino M C, Cerletti C, Marchi S, Garattini S, Gaetano G D. How intravenous administration of low dose aspirin inhibits both vascular and platelet cyclooxygenase activity: an experimental study in the rats. Expt Bio Med 182:287, 1986.

B31. Pierangeli S S, Barker J H, Stikovac D, Ackerman D, Anderson G, Barquinero J, Acland R, Harris E N. Effect of human IgG antiphospholipid antibodies on an in vivo thrombosis model in mice. Thromb Haemost 71: 670-674, 1994.

B32. Edwards M H, Pierangeli S, Liu X, Barker J H, Anderson G, Harris E N. Hydroxychloroquine reverses thrombogenic antibodies in mice. Circulation 96: 4380-4384, 1997.

B33. Pierangeli S S, Liu X, Antonov J T, Sparrow J T, Harris E N, Myones B L. Induction of pathogenic anticardiolipin antibodies in a murine model. Arthritis Rheum 41: 5135, 1998.

B34. Myones B L, Antonov I V, Fedorova L I, Volgin A Y, Liu X, Espinola R, Harris E N, Pierangeli S S. Complexes of protein and saturated cardiolipin are capable of binding antiphospholipid antibodies and inducing thrombogenic antiphospholipid antibodies in a murine model. Arthritis Rheum 42: 5369, 1999.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

I claim:

1. A method for producing a pharmaceutical composition comprising admixing an NSAID in powder form into an oil-based carrier to obtain an NSAID-in-oil suspension, wherein:
   (a) the oil-based carrier comprises a phospholipid and a bio-compatible oil;
   (b) the NSAID is present in a therapeutically effective amount; and
   (c) the NSAID-in-oil suspension has a gastrointestinal toxicity that is reduced relative to the NSAID alone.

2. The method of claim 1, wherein the oil based carrier comprises from about 20 wt. % to about 80 wt. % phospholipids.

3. The method of claim 1, wherein the NSAID is selected from the group consisting of propionic acid drugs, acetic acid drugs, ketone drugs, fenamate drugs, oxicam drugs, salicylic acid drugs, pyrazolin acid drugs, acetaminophen, and COX-2 inhibitors.

4. The method of claim 1, wherein the NSAID is selected from the group consisting of aspirin, fenoprofen, flurbiprofen, suprofen, benoxaprofen, ibuprofen, ketoprofen, naproxen, oxaprozin, diclofenac, etodolac, indomethacin, ketorolac tromethamine, ketorolac, nabumetone, sulindac, tolmetin, meclofenamate, mefenamic acid, piroxicam, diflunisal, oxyphenbutazone, phenylbutazone, acetaminophen, celecoxib, rofecoxib, and mixtures or combinations thereof.

5. The method of claim 1, wherein the bio-compatible oil is selected from the group consisting of vegetable oils, hydrogenated vegetable oils, and mixtures or combinations thereof.

6. The method of claim 5, wherein the oils are selected from the group consisting of peanut oil, canola oil, avocado oil, safflower oil, olive oil, corn oil, soy bean oil, sesame oil, vitamin A, vitamin D, vitamin E, and mixtures or combinations thereof.

7. The method of claim 1, wherein the weight ratio of NSAID to oil-based carrier present in the NSAID-in-oil suspension is from about 4:1 to about 1:4.

8. The method of claim 7, wherein the weight ratio of NSAID to oil-based carrier is about 1:1.

9. The method of claim 1, wherein the oil-based carrier comprises between about 20 wt. % and about 60 wt. % phospholipids.

10. The method of claim 1, wherein the oil-based carrier comprises between about 20 wt. % and about 40 wt. % phosphatidylcholine.

11. The method of claim 1, wherein the NSAID associates with the phospholipid.

12. A pharmaceutical composition that is a non-steroidal anti-inflammatory drug (NSAID)-in-oil suspension comprising an NSAID in powder form and a lecithin oil, wherein:
  (a) the NSAID-in-oil suspension comprises from about 20 wt. % to about 80 wt. % phospholipids;
  (b) the NSAID is present in a therapeutically effective amount; and
  (c) the composition has a gastrointestinal (GI) toxicity that is reduced relative to the NSAID alone.

13. The composition according to claim 12, wherein the NSAID-in-oil suspension comprises from about 20 wt. % to about 80 wt. % phospholipids.

14. The composition of claim 12, wherein the NSAID is selected from the group consisting of propionic acid drugs, acetic acid drugs, ketone drugs, fenamate drugs, oxicam drugs, salicylic acid drugs, pyrazolin acid drugs, acetaminophen, and COX-2 inhibitors.

15. The composition of claim 12, wherein the NSAID is selected from the group consisting of aspirin, fenoprofen, flurbiprofen, suprofen, benoxaprofen, ibuprofen, ketoprofen, naproxen, oxaprozin, diclofenac, etodolac, indomethacin, ketorolac tromethamine, ketorolac, nabumetone, sulindac, tolmetin, meclofenamate, mefenamic acid, piroxicam, diflunisal, oxyphenbutazone, phenylbutazone, acetaminophen, celecoxib, rofecoxib, and mixtures or combinations thereof.

16. The composition according to claim 12, wherein the weight ratio of NSAID to lecithin oil present in the NSAID-in-oil suspension is from about 4:1 to about 1:4.

17. The composition according to claim 16, wherein the weight ratio of NSAID to lecithin oil is about 1:1.

18. The composition of claim 11, wherein the NSAID is associated with the phospholipid.

19. A pharmaceutical composition that is an NSAID-in-oil suspension and that is the product of a process that comprises admixing an NSAID in powder form into an oil-based carrier, to obtain a NSAID-in-oil suspension, wherein the oil-based carrier comprises a lecithin oil and from about 20 wt. % to about 80 wt. % phospholipids, wherein:
  (a) the NSAID is present in a therapeutically effective amount; and
  (b) the composition has a GI toxicity that is reduced relative to that of the NSAID alone.

20. The composition of claim 19, wherein the NSAID-in-oil suspension comprises from about 20 wt. % to about 60 wt. % phospholipids.

21. The composition of claim 19, wherein the NSAID is selected from the group consisting of propionic acid drugs, acetic acid drugs, ketone drugs, fenamate drugs, oxicam drugs, salicylic acid drugs, pyrazolin acid drugs, acetaminophen, and COX-2 inhibitors.

22. The composition of claim 19, wherein the NSAID is selected from the group consisting of aspirin, fenoprofen, flurbiprofen, suprofen, benoxaprofen, ibuprofen, ketoprofen, naproxen, oxaprozin, diclofenac, etodolac, indomethacin, ketorolac tromethamine, ketorolac, nabumetone, sulindac, tolmetin, meclofenamate, mefenamic acid, piroxicam, diflunisal, oxyphenbutazone, phenylbutazone, acetaminophen, celecoxib, rofecoxib, and mixtures or combinations thereof.

23. The composition according to claim 19, wherein the bio-compatible oil is selected from the group consisting of vegetable oils, hydrogenated vegetable oils, and mixtures or combinations thereof.

24. The composition according to claim 19, wherein the weight ratio of NSAID to oil-based carrier present in the NSAID-in-oil suspension is from about 4:1 to about 1:4.

25. The composition according to claim 24, wherein the weight ratio of NSAID to oil-based carrier is about 1:1.

26. The composition of claim 19, wherein the NSAID is associated with the phospholipid.

* * * * *